(12) United States Patent
Sato

(10) Patent No.: US 6,867,161 B1
(45) Date of Patent: Mar. 15, 2005

(54) TITANIUM CATALYST AND ORGANOTITANIUM REACTING REAGENT, PRODUCTION THEREOF, AND REACTION THEREBY

(75) Inventor: Fumie Sato, 3-1-219, Kugenumahigashi, Fujisawa-shi, Kanagawa-ken 251 (JP)

(73) Assignees: Nissan Chemical Industries, Ltd., Tokyo (JP); Fumie Sato, Fujisawa (JP)

( * ) Notice: Subject to any disclaimer, the term of this patent is extended or adjusted under 35 U.S.C. 154(b) by 0 days.

(21) Appl. No.: 08/913,218

(22) PCT Filed: Mar. 8, 1996

(86) PCT No.: PCT/JP96/00578

§ 371 (c)(1),
(2), (4) Date: Sep. 8, 1997

(87) PCT Pub. No.: WO96/28250

PCT Pub. Date: Sep. 19, 1996

(30) Foreign Application Priority Data

Mar. 10, 1995 (JP) .............................................. 7-79685

(51) Int. Cl.$^7$ .............................. B01J 31/00; C07F 7/28
(52) U.S. Cl. ........................ 502/152; 502/150; 502/170; 502/103; 502/104; 556/51; 556/52; 556/54; 560/180
(58) Field of Search .............................. 556/51, 52, 54; 502/103, 104, 150, 152, 170; 560/180

(56) References Cited

U.S. PATENT DOCUMENTS 3,424,736 A 1/1969 Nudenberg et al.

FOREIGN PATENT DOCUMENTS

| EP | 0103120 A2 | 3/1984 |
|---|---|---|
| EP | 0458643 A2 | 11/1991 |
| FR | 2097571 | 3/1972 |
| GB | 801031 | 9/1958 |
| GB | 856434 | 12/1960 |
| GB | 948714 A | 2/1964 |
| GB | 948714 | 2/1964 |
| GB | 969467 A | 9/1964 |
| GB | 969467 | 9/1964 |
| GB | 1171597 | 9/1969 |
| JP | 50-30102 | 9/1975 |
| JP | 52-3064 | 1/1977 |
| JP | 5-339192 | 12/1993 |
| WO | WO9502567 A1 | 1/1995 |

OTHER PUBLICATIONS

Negishi, Comprehensive Organic Synthesis, vol. 5, pp. 1163–1184 (1991).
Negishi et al., Yuki Gosei Kagaku, vol. 47, pp. 2–10 (1989).
Sato, Yuki Gosei Kagaku, vol. 38, pp. 234–243 (1980).
McMurry, Acc. Chem. Res., vol. 7, No. 9, pp. 281–286 (1974).

"Organotitanium Reagents in Organic Synthesis", Springer, p. 1 (1986).
Corey et al., J. Am Chem. Soc., vol. 116, pp. 9345–9346 (1994).
Mikami et al., J. Am. Chem. Soc., vol. 112, pp. 3949–3954 (1990).
Mukaiyama, Angew. Chem. Int. Ed. Engl., vol. 16, pp. 817–826 (1977).
Sato et al. Tetrahedron Letters, vol. 22, pp. 243–246, 1981.
Berk et al. J. Am. Chem. Soc., vol. 116, pp. 8593–8601, 1994.
Weber et al. Tetrahedron, vol. 50, No. 25, pp. 7473–7484, 1994.
Reetz et al. Chem. Ber, vol. 118, No. 4, pp. 1421–1440, 1985.
Corey et al. J. Am. Chem. Soc., vol. 116, pp. 9345–9346, 1995.
Negishi. Comprehensiv Organic Synthesis, vol. 5, pp. 1163–1184, 1991.

(List continued on next page.)

Primary Examiner—Porfirio Nazario-Gonzalez
(74) Attorney, Agent, or Firm—Birch, Stewart, Kolasch & Birch, LLP

(57) ABSTRACT

A titanium catalyst for reaction between a compound having a carbon-carbon unsaturated bond and a compound having an electrophilic functional group or an electrophilic reagent, said titanium catalyst being composed of a titanium compound represented by the formula (1) below $$TiX^1X^2X^3X^4 \qquad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.) and a Grignard reagent represented by the formula (2) below in a molar amount 1.5–2.5 times as much as the titanium compound.

$$R^1MgX^5 \qquad (2)$$

(where $R^1$ denotes a $C_{2-10}$ alkyl group having a hydrogen atom at the β position and $X^5$ denotes a halogen atom.)

The titanium catalyst of the present invention activates the carbon-carbon unsaturated bond, which has a comparatively low reactivity, thereby catalyzing the reaction with an electrophilic functional group. It is inexpensive and industrially advantageous. When applied to reaction between a compound having a carbon-carbon unsaturated bond and an electrophilic functional group, it yields industrially a variety of adducts of a compound having a carbon-carbon unsaturated bond and a compound having an electrophilic functional group, and it also yields a variety of intramolecular adducts of a compound having a carbon-carbon unsaturated bond and an electrophilic functional group in the same molecule.

24 Claims, No Drawings

OTHER PUBLICATIONS

Martin et al. *J. of Organometallic Chmeistry*, vol. 12, pp. 149–161, 1968.

Martin et al. *J. of Organometallic Chemistry*, vol. 8, pp. 115–128, 1967.

Nakagawa et al. *Tetrahedron Letters*, vol. 36, No. 18, pp. 3207–3210, 1995.

Kasatkin et al. *Tetrahedron Letters* vol. 36, No. 34, pp. 6075–6078, Aug. 1, 1995.

Derwent Publications Ltd., London, GB, Class B05, An 1997–466209, JP 09 216849 (Aug. 19, 1997).

Kulinkovich et al., Mendeleev Commun., 1993 pp. 230–231.

Nakagawa, Takashi et al., Tetrahedron Letters, vol. 36, No. 18, 1995, pp. 3207–3210.

Kasatkin, A. et al., Tetrahedron Letters, vol. 36, No. 34, 1995, pp. 6075–6078.

TITANIUM CATALYST AND ORGANOTITANIUM REACTING REAGENT, PRODUCTION THEREOF, AND REACTION THEREBY

TECHNICAL FIELD

The present invention relates to a new titanium catalyst and organotitanium reacting reagent, a process for their production, and a useful reaction by them.

BACKGROUND ART

Titanium compounds have been widely used for organic syntheses mostly in the form of Lewis acid catalyst or nucleophilic reagent in which the ligand is replaced by a nucleophilic reagent. The former is used for aldol reaction and Michael reaction (Mukaiyama et al., Angew. Chem., Int. Ed. Engl., 16, 817 (1977)) or for asymmetric ene reaction (Mikami et al., J. Am. Chem. Soc., 112, 3949 (1990)), and the latter is used for reaction of an organotitanium to be obtained from a titanium compound and an organolithium or Grignard reagent (Reetz et al., "Organotitanium Reagents in Organic Synthesis", Springer (1986)) or for reaction between an ester compound and a complex obtained from a titanium compound and an alkyl Grignard reagent (Corey et al., J. Am. Chem. Soc., 116, 9345 (1994)).

The catalytic use of a titanium compound for the coupling reaction of less reactive molecules has been limited. (For example, the use of a low-valence titanium compound (obtained from a titanium compound and a reducing agent) for dimerization of a carbonyl compound ((McMurry et al., Acc. Chem. Res., 7, 281 (1974)) and the use for the reaction that employs a Ziegler type reacting reagent obtained by combination of a titanium compound with a typical metal compound (Sato et al., Yuki Gosei Kagaku, 38, 234 (1980)).

In contrast with titanium, zirconium (which also belongs to Group IVa) is an extremely useful metal catalyst for organic syntheses. For example, it functions as a divalent catalyst typified by zirconocene (biscyclo-pentadienyl zirconium) for the reaction of the carbon-carbon unsaturated bond, which has a comparatively low reactivity. (Negishi et al., Yuki Gosei Kagaku, 47, 2 (1989)). A few reactions by titanocene (as a titanium compound) are known; but they are seldom superior to those by zirconocene. (E. Negishi, Comprehensive Organic Synthesis, vol. 5, 1163–1184 (1991); B. M. Trost, I. Fleming, L. A. Paquette, Eds., Pergamon Press). Moreover, zirconocene and titanocene are too expensive for industrial use.

DISCLOSURE OF THE INVENTION

It is an object of the present invention to provide a new titanium catalyst and organotitanium reacting reagent to be used for reaction between a compound having a carbon-carbon unsaturated bond and a compound having an electrophilic functional group or an electrophilic reagent. It is another object of the present invention to provide a process for producing them. It is another object of the present invention to provide a process for addition reaction between a compound having a carbon-carbon unsaturated bond and a compound having an electrophilic functional group or an electrophilic reacting reagent, or for intramolecular addition reaction of a compound having both a carbon-carbon unsaturated bond and an electrophilic functional group in the same molecule, or for deallylating reaction to give a malonate ester derivative by deallylation of an allyl-substituted malonate ester, by the aid of said titanium catalyst or organotitanium reacting reagent.

In order to achieve the above-mentioned object, the present inventors carried out a series of researches which led to the finding that when a compound (such as olefin compound, acetylene compound, and allene compound) having a carbon-carbon aliphatic or alicyclic unsaturated bond is reacted with a compound having an electrophilic functional group (such as aldehyde group, ketone group, imino group, hydrazone group, aliphatic or alicyclic double or triple bond, acyl group, ester group, and carbonate group) or with an electrophilic reagent in the presence of a titanium compound represented by the formula (1) below and a Grignard reagent represented by the formula (2) below (in a molar amount about 1–10 times as much as said titanium compound), the carbon-carbon aliphatic or alicyclic unsaturated bond (having a comparatively low reactivity) is activated, with the result that addition reaction between a compound having a carbon-carbon unsaturated bond and a compound having an electrophilic functional groups or a nucleophilic compound is catalyzed, and there is obtained an addition product of a compound having a carbon-carbon unsaturated bond with a compound having an electrophilic functional group or an electrophilic reagent. It was also found that in the case where the reaction is applied to a compound having both a carbon-carbon aliphatic or alicyclic unsaturated bond and an electrophilic functional group in the same molecule, the intramolecular addition reaction advantageously proceeds. It was also found that the above-mentioned titanium catalyst permits the deallylation of an allyl-substituted malonate ester derivative represented by the formula (3) below, thereby giving a malonate ester derivative represented by the formula (4) below in high yields without side reactions.

Incidentally, in J. Am. Chem. Soc., 116, 9345 (1994) mentioned above, Corey et al. reported the reaction which employs a titanium compound and an alkyl Grignard reagent as the reaction reagent. This combination is similar to that in the present invention; however, they use the alkyl group originating from the Grignard reagent as the nucleophilic reagent in their reaction. By contrast, the present invention employs as a catalyst the reaction products formed from the titanium compound and the alkyl Grignard reagent, thereby performing reaction on unsaturated compounds and electrophilic reagents. In other words, the present invention differs essentially from Corey's reaction in that the alkyl group originating from Grignard reagent is not used for reaction. Thus the present invention will find use in a broad range of applications.

The present invention provides the following.

[i] A titanium catalyst for reaction between a compound having a carbon-carbon unsaturated bond and a compound having an electrophilic functional group or an electrophilic reagent, said titanium catalyst being composed of a titanium compound represented by the formula (1) below $$TiX^1X^2X^3X^4 \qquad (1)$$

(where $X^1$, $X^2$, $X^3$, and $X^4$ denote independently a halogen atom, $C_{1-20}$ alkoxyl group, aralkyloxy group, aryloxy group, or —$NR_xR_y$ group (where $R_x$ and $R_y$ denote independently a $C_{1-20}$ alkyl group or aralkyl group), and any two of $X^1$, $X^2$, $X^3$, and $X^4$ may form a ring.) and a Grignard reagent represented by the formula (2) below in a molar amount 1–10 times as much as the titanium compound.

$$R^1MgX^5 \quad (2)$$

(where $R^1$ denotes a $C_{2-10}$ alkyl group having a hydrogen atom at the a position and $X^5$ denotes a halogen atom.)

[ii] A process for producing a titanium catalyst for reaction between a carbon-carbon unsaturated bond and a compound having an electrophilic functional group or an electrophilic reagent, said process comprising reacting a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.) with a Grignard reagent represented by the formula (2) below in a molar amount 1–10 times as much as the titanium compound.

$$R^1MgX^5 \quad (2)$$

(where $R^1$ denotes a $C_{2-10}$ alkyl group having a hydrogen atom at the β position and $X^5$ denotes a halogen atom.)

[iii] An organotitanium reacting reagent which is composed of a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.), a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom.), and a compound having a carbon-carbon unsaturated bond.

[iv] A process for producing an organotitanium reacting reagent, said process comprising reacting together a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.), a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom.), and a compound having a carbon-carbon unsaturated bond.

[v] A process for addition reaction which comprises performing addition reaction on a compound having a carbon-carbon unsaturated bond and a compound having an electrophilic functional group or an electrophilic reagent, in the presence of a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.) and a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom.)

[vi] A process for addition reaction as defined in [v] above wherein the compound having a carbon-carbon unsaturated bond and the compound having an electrophilic functional group are replaced by a compound having both a carbon-carbon unsaturated bond and an electrophilic functional group in the same molecule for intramolecular addition reaction.

[vii] A process for addition reaction which comprises adding a compound having an electrophilic functional group or an electrophilic reagent to an organotitanium reacting reagent which is obtained from a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.), a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom.), and a compound having a carbon-carbon unsaturated bond, thereby performing addition reaction on said compound having a carbon-carbon unsaturated bond.

[viii] A process which comprises reacting a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.) with a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom.), thereby forming a titanium catalyst, and deallylating in the presence of the titanium catalyst an allyl-substituted malonate ester derivative represented by the formula (3) below $$R^2R^3C=CR^4CH_2C(Ra)(COORb)_2 \quad (3)$$

(where $R^2$, $R^3$, and $R^4$ denote independently a hydrogen atom or $C_{1-10}$ alkyl group, Ra denotes a $C_{1-20}$ substituted or unsubstituted alkyl group, alkenyl group, or aralkyl group, and Rb denotes a $C_{1-10}$ alkyl group or aralkyl group), thereby giving a malonate ester derivative represented by the formula (4) below $$RaCH(COORb)_2 \quad (4)$$

(where Ra and Rb are defined as above).

[ix] A process which comprises alkylating an allylmalonate ester represented by the formula (5) below $$R^2R^3C=CR^4CH_2CH(COORb)_2 \quad (5)$$

(where $R^2$, $R^3$, and $R^4$ denote independently a hydrogen atom or $C_{1-10}$ alkyl group, and Rb denotes a $C_{1-10}$ alkyl group or aralkyl group), thereby giving an allyl-substituted malonate ester derivative represented by the formula (3) below $$R^2R^3C=CR^4CH_2C(Ra)(COORb)_2 \quad (3)$$

(where $R^2$, $R^3$, $R^4$, and Rb are defined as above, and Ra denotes a $C_{1-20}$ substituted or unsubstituted alkyl group, alkenyl group, or aralkyl group), reacting this derivative with a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.) and a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom.), thereby forming a titanium catalyst, and performing deallylating reaction in the presence of the titanium catalyst, thereby giving a malonate ester derivative represented by the formula (4) below $$RaCH(COORb)_2 \quad (4)$$

(where Ra and Rb are defined as above).

BEST MODE FOR CARRYING OUT THE INVENTION

The first aspect of the present invention resides in a titanium catalyst for reaction between a compound having a carbon-carbon unsaturated bond and a compound having an electrophilic functional group or an electrophilic reagent, said titanium catalyst being composed of a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.) and a Grignard reagent represented by the formula (2) below in a molar amount 1–10 times as much as the titanium compound.

$$R^1MgX^5 \quad (2)$$

(where $R^1$ denotes a $C_{2-10}$ alkyl group having a hydrogen atom at the β position and $X^5$ denotes a halogen atom.)

The second aspect of the present invention resides in a process for producing a titanium catalyst by the reaction of a titanium compound represented by the formula (1) above with a Grignard reagent represented by the formula (2) above in a molar amount 1–10 times as much as the titanium compound.

In formula (1), $X^1$, $X^2$, $X^3$, and $X^4$ denote independently a halogen atom, $C_{1-20}$ alkoxyl group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring.

The halogen atom includes, for example, fluorine atom, chlorine atom, bromine atom, and iodine atom. The $C_{1-20}$ alkoxyl group, aralkyloxy group, or aryloxy group includes, for example, methoxy, ethoxy, propoxy, i-propoxy, butoxy, i-butoxy, sec-butoxy, t-butoxy, hexyloxy, heptyloxy, octyloxy, nonyloxy, menthyloxy, benzyloxy, phenethyloxy, phenoxy, naphthyloxy, biphenyloxy, and binaphthyloxy. Rx and Ry include, for example, methyl, ethyl, propyl, isopropyl, butyl, s-butyl, t-butyl, hexyl, cyclohexyl, heptyl, octyl, nonyl, benzyl, phenethyl, and naphthylethyl. The ring-forming group includes, for example, ethylenedioxy, propylenedioxy, 1,2-dimethylethylenedioxy, tartrate diester dioxy, biphenyl-1,1'-dioxy, binaphthyl-1,1'-dioxy, and ethylene-1-amino-2-oxy, which form 5- to 7-membered rings by connection to a titanium atom through an oxygen or nitrogen atom. Preferred examples of the titanium compound represented by the formula (1) include tetraisopropoxytitanium, chlorotriisopropoxytitanaium, and dichlorodipropoxytitanium.

If the titanium compound has an asymmetric ligand, it yields an optically active compound through the asymmetric reaction with a nucleophilic group as mentioned later. The asymmetric ligand includes, for example, α-phenethyloxy, α-phenethylamino, menthyloxy, tartrate diester dioxy, biphenyldioxy, binaphthyldioxy, and 2-phenyl-ethylene-1-amino-2-oxy.

In the formula (2), $R^1$ denotes a $C_{2-10}$ alkyl group having a hydrogen atom at the β-position and $X^5$ denotes a halogen atom. The $C_{2-10}$ alkyl group having a hydrogen atom at the β-position includes, for example, ethyl, propyl, i-propyl, butyl, i-butyl, sec-butyl, pentyl, i-pentyl, hexyl, i-hexyl, heptyl, i-heptyl, octyl, i-octyl, nonyl, i-nonyl, decyl, and i-decyl. The halogen atom includes, for example, chlorine atom, bromine atom, and iodine atom. Preferred examples of the Grignard reagent represented by the formula (2) include ethylmagnesium chloride, ethylmagnesium bromide, propylmagnesium chloride, propylmagnesium bromide, i-propylmagnesium chloride, and i-propylmagnesium bromide.

According to the second aspect of the present invention, the titanium catalyst is prepared simply by reacting in an inert solvent a titanium compound represented by the formula (1) with a Grignard reagent represented by the formula (2) in a molar amount of 1–10 times as much as the titanium compound. The inert solvent is not specifically restricted so long as it is not involved in the reaction. It includes, for example, saturated hydrocarbons (such as hexane and heptane), aromatic hydrocarbons (such as benzene and toluene), and ethers (such as diethyl ether, diisopropyl ether, t-butyl methyl ether, tetrahydrofuran, and dioxane). Preferred solvents include ethers, diethyl ether, diisopropyl ether, and t-butyl methyl ether. Reaction temperature should be −100 to 0° C., preferably −78 to −10° C. Reaction time should be 1 minute to 20 hours, preferably 1.0 minutes to 2 hours, depending on the reaction temperature. The equivalent amount of the Grignard reagent for the titanium compound should be 1–10, preferably 1.5–2.5, so that side reactions with the reaction substrate are avoided.

The above-mentioned titanium catalyst composed of a titanium compound and a Grignard reagent is used for reaction between a carbon-carbon unsaturated bond and an electrophilic functional group. It is possible to add to the reaction system the titanium compound and Grignard reagent in the form of their reaction product prepared beforehand or separately such that they react in the reaction system. The latter procedure is simpler. The reaction system to which the titanium compound and Grignard reagent are added need not to contain both a compound having a carbon-carbon unsaturated bond and a compound having an electrophilic functional group or an electrophilic reagent. The reaction system will be satisfactory if it contains either of them, preferably the former.

The third aspect of the present invention resides in an organotitanium reacting reagent which is composed of a titanium compound represented by the formula (1) above, a Grignard reagent represented by the formula (2) above in a molar amount 1–10 times as much as the titanium compound, and a compound having a carbon-carbon unsaturated bond.

The fourth aspect of the present invention resides in a process for producing an organotitanium reacting reagent by mixing together a titanium compound represented by the formula (1) above, a Grignard reagent represented by the formula (2) above in a molar amount 1–10 times as much as the titanium compound, and a compound having a carbon-carbon unsaturated bond.

The carbon-carbon unsaturated bond means an aliphatic or alicyclic double bond or triple bond, and the compound having such an unsaturated bond includes olefin compounds, acetylene compounds, and allene compounds.

The compound having a carbon-carbon unsaturated bond should be used in such an amount that the titanium catalyst (composed of the titanium compound and the Grignard reagent in a molar amount 1–10 times as much as the titanium compound) is 0.01–5 equivalent, preferably 0.5–1.2 equivalent, per equivalent of said compound.

The organotitanium reacting reagent permits the compound having a carbon-carbon unsaturated bond to be involved in the addition reaction with a compound having an electrophilic functional group or with an electrophilic reagent.

This organotitanium reacting reagent can be obtained from the above-mentioned titanium compound, Grignard reagent, and compound having a carbon-carbon unsaturated bond by mixing and reaction in an inert solvent. The inert solvent is not specifically restricted so long as it is not involved in the reaction. It includes, for example, saturated hydrocarbons (such as hexane and heptane), aromatic hydrocarbons (such as benzene and toluene), ethers (such as diethyl ether, diisopropyl ether, t-butyl methyl ether, tetrahydrofuran, and dioxane), and halogenated hydrocarbons (such as dichloromethane and dichloroethane), and mixtures thereof. Of these examples, ether solvents are preferable. The reaction temperature should be in the range of −100° C. to the reflux temperature of the solvent, preferably −78° C. to 0° C. The reaction time should be 1 minute to 20 hours, preferably 10 minutes to 4 hours, depending on the reaction temperature.

The above-mentioned titanium catalyst of the present invention activates the carbon-carbon unsaturated bond (aliphatic or alicyclic C—C double bond or C—C triple bond) and catalyzes the reaction of various electrophilic functional groups and electrophilic reagents.

Therefore, the fifth aspect of the present invention resides in a process for performing addition reaction between a compound having a carbon-carbon unsaturated bond and a compound having an electrophilic functional group or an electrophilic reagent in the presence of the titanium compound represented by the formula (1) above and the Grignard reagent represented by the formula (2) above in a molar amount 1–10 times as much as the titanium compound. The sixth aspect of the present invention resides in a process for performing intramolecular addition reaction on a compound having a carbon-carbon unsaturated bond and an electrophilic functional group in the same molecule (in place of the compound having a carbon-carbon unsaturated bond and the compound having an electrophilic functional group which are used in the above-mentioned addition reaction). The seventh aspect of the present invention resides in a process for performing addition reaction on a compound having a carbon-carbon unsaturated bond by adding to the above-mentioned titanium reacting reagent a compound having an electrophilic functional group or an electrophilic reagent.

Examples of the electrophilic functional group include aldehyde groups, ketone groups, imino groups, hydrazone groups, double bonds, triple bonds, acyl groups, ester groups, and carbonate groups. Examples of the compound include aldehyde compounds, ketone compounds, imine compounds, hydrazone compounds, olefin compounds, acetylene compounds, acyl compounds, ester compounds, $\alpha,\beta$-unsaturated carbonyl compounds, and carbonate ester compounds. These functional groups may be present within the above-mentioned molecule having a carbon-carbon unsaturated bond. Examples of the electrophilic reagent include water, heavy water, chlorine, bromine, iodine, N-bromosuccimide, oxygen, carbon dioxide gas, and carbon monoxide.

Presumably, the reaction forms as an intermediate the organotitanium reacting reagent from the titanium catalyst and the carbon-carbon unsaturated bond and the intermediate reacts with the electrophilic functional group or electrophilic reagent. In this case the reaction is carried out in an inert solvent. The inert solvent is not specifically restricted so long as it is not involved in the reaction. It includes, for example, saturated hydrocarbons (such as hexane and heptane), aromatic hydrocarbons (such as benzene and toluene), ethers (such as diethyl ether, diisopropyl ether, t-butyl methyl ether, tetrahydrofuran, and dioxane), and halogenated hydrocarbons (such as dichloro-methane and dichloroethane), and mixtures thereof. Ether solvents of the same type are desirable for the preparation of the titanium catalyst and the continuous operation. The reaction temperature should be in the range of −100° C. to the reflux temperature of the solvent, preferably −78° C. to 0° C. The reaction time should be 1 minute to 20 hours, preferably 10 minutes to 4 hours, depending on the reaction temperature. The amount of the electrophilic functional group compound should be 0.5–2 equivalents, preferably 0.7–1.3 equivalents, per equivalent of the carbon-carbon unsaturated bond compound, and the amount of the titanium catalyst should be 0.01–5 equivalents, preferably 0.5–1.2 equivalents, per equivalent of the carbon-carbon unsaturated bond compound.

The reactants may be added in the following order.

After catalyst preparation, the carbon-carbon unsaturated bond compound is added and then the electrophilic functional group compound or the electrophilic reagent is added.

The catalyst is prepared in the presence of the carbon-carbon unsaturated bond compound and then the electrophilic functional group compound or the electrophilic reagent is added.

The catalyst is added to a solution of the carbon-carbon unsaturated bond compound and the electrophilic functional group compound or the electrophilic reagent.

Mixing together simultaneously all the reactants—the titanium compound, the Grignard reagent, the carbon-carbon unsaturated bond compound, and the electrophilic functional group compound or the electrophilic reagent.

It is possible to add the reactants after catalyst preparation or to prepare the catalyst in the presence of the reactants also in the case where the carbon-carbon unsaturated bond and the electrophilic functional group are present in the same molecule. After the reaction with the electrophilic functional group compound, it is possible to suspend the reaction by adding an electrophilic reagent such as water.

Typical reactions are shown below to explain the usefulness of the present invention. In the formulas below, Ra—Rk independently represent organic substituent groups such as hydrogen atom, substituted or unsubstituted linear or branched $C_{1-20}$, especially $C_{1-10}$, alkyl group, aralkyl group, alkenyl group, or alkynyl group, substituted or unsubstituted aromatic group, heterocyclic group, cycloalkane group, alkyl- or aromatic-substituted silyl group, alkyl- or aromatic-substituted tin group, and ester group.

The $C_{1-20}$ alkyl group includes methyl, ethyl, n-propyl, i-propyl, n-butyl, sec-butyl, t-butyl, pentyl, octyl, decyl, dodecyl, octadecyl, and eicosanyl.

The $C_{7-17}$ aralkyl group includes benzyl, phenethyl, and α-methylbenzyl.

The $C_{2-20}$ alkenyl group include vinyl, allyl, crotyl, decenyl, dodecenyl, octadecenyl, and eicosenyl.

The $C_{2-20}$ alkynyl group includes ethynyl, hexynyl, decynyl, dodecynyl, octadecynyl, and eicosynyl.

The aromatic group includes phenyl, naphthyl, and anthranyl.

The heterocyclic group includes furyl, thiophenyl, and pyrazolyl.

The $C_{3-10}$ cycloalkyl group includes cyclopropyl, cyclopentyl, cyclohexyl, cycloheptyl, and cyclodecyl.

The substituted silyl group includes trimethyl silyl, triethyl silyl, tri-n-propylsilyl, tri-n-butylsilyl, t-butyldimethylsilyl, and tri-n-decylsiyl.

The alkyl- or aromatic-substituted tin group include trimethyltin, triethyltin, tributyltin, triphenyltin, and tribenzyltin.

The ester group includes $C_{2-11}$ ester groups such as methyl ester, ethyl ester, butyl ester, and decyl ester.

The above-mentioned $C_{1-20}$ alkyl group, $C_{7-17}$ aralkyl group, $C_{2-20}$ alkenyl group, $C_{2-20}$ alkynyl group, aromatic group, heterocyclic group, $C_{3-10}$ cycloalkyl group, substituted silyl group, alkyl- or aromatic-substituted tin group, and ester group may have a substituent group such as halogen atom, $C_{1-10}$ acyl group, $C_{1-10}$ carbamate group, $C_{1-10}$ ether group, $C_{1-10}$ sulfonate ester group, $C_{1-10}$ phosphate ester group, $C_{7-17}$ aralkyl group, and $C_{2-11}$ ester group.

Examples are given below.

The olefin compound includes (substituted) halogenated allyl and (substituted) allyl alcohol derivatives.

The (substituted) halogenated allyl includes $C_{1-20}$ alkyl-substituted halogenated allyl, phenyl-substituted halogenated allyl, o-halogenophenyl-substituted halogenated allyl, m-halogenophenyl-substituted halogenated allyl, and p-halogenophenyl-substituted halogenated allyl.

The (substituted) allyl alcohol derivative includes $C_{4-13}$ allyl alcohol alkyl ester, $C_{4-13}$ allyl alcohol alkyl carbamate, $C_{4-13}$ allyl alcohol alkyl ether, $C_{4-13}$ allyl alcohol alkylsulfonate ester, allyl alcohol-o-hydroxyphenylsulfonate ester, allyl alcohol-m-hydroxylphenylsulfonate ester, allyl alcohol-p-hydroxyphenylsulfonate ester, and $C_{4-13}$ allyl alcohol alkyl phosphate ester.

The above-mentioned allyl alcohol derivative may also have a substituent group such as $C_{1-20}$ alkyl group, phenyl group, o-halogenophenyl group, m-halogenophenyl group, and p-halogenophenyl group.

The acetylene compound includes (substituted) $C_{2-20}$ compounds having a triple bond, (substituted) halogenated propargyl, (substituted) trialkyl ($C_{3-12}$) silylhalogenated propargyl, and (substituted) propargyl alcohol derivative.

The substituent group of the (substituted) $C_{2-20}$ compound having a triple bond includes $C_{1-20}$ alkyl group, phenyl group, o-halogenophenyl group, m-halogenophenyl group, p-halogenophenyl group, and trialkyl ($C_{3-12}$) silyl group.

The (substituted) halogenated propargyl includes $C_{1-20}$ alkyl-substituted halogenated propargyl, phenyl-substituted halogenated propargyl, o-halogenophenyl-substituted halogenated propargyl, m-halogenophenyl-substituted halogenated propargyl, p-halogenophenyl-substituted halogenated propargyl.

The (substituted) trialkyl ($C_{3-12}$) silylhalogenated propargyl includes trimethylsilyl halogenated propargyl, triethylsilyl halogenated propargyl, tri-n-propylsilyl halogenated propargyl, tri-n-butylsilyl halogenated propargyl, t-butyldimethylsilyl halogenated propargyl, and tri-n-decylsilyl halogenated propargyl.

The (substituted) propargyl alcohol derivative includes $C_{4-13}$ propargyl alcohol alkyl ester, $C_{4-13}$ propargyl alcohol alkyl carbamate, $C_{4-13}$ propargyl alcohol alkyl ether, $C_{4-13}$ propargyl alcohol alkylsulfonate ester, propargyl alcohol-o-hydroxyphenylsulfonate ester, propargyl alcohol-m-hydroxyphenylsulfonate ester, propargyl alcohol-p-hydroxyphenylsulfonate ester, and $C_{4-13}$ propargyl alcohol alkyl phosphate ester.

The above-mentioned ($C_{3-12}$) silylhalogenated propargyl and propargyl alcohol derivative may be substituted further by any of $C_{1-20}$ alkyl group, phenyl group, o-halogenophenyl group, m-halogenophenyl group, p-halogenophenyl group, and trialkyl ($C_{3-12}$) silyl group.

The allene compound includes (substituted) halogenated allenyl and (substituted) allenyl alcohol derivatives.

The (substituted) halogenated allenyl includes $C_{1-20}$ alkyl-substituted halogenated allenyl, $C_{3-10}$ cycloalkyl-substituted halogenated allenyl, phenyl-substituted halogenated allenyl, o-halogenophenyl-substituted halogenated allenyl, m-halogenophenyl-substituted halogenated allenyl, and p-halogenophenyl-substituted halogenated allenyl.

The (substituted) allenyl alcohol derivative includes $C_{4-13}$ allenyl alcohol alkyl ester, $C_{4-13}$ allenyl alcohol alkyl carbamate, $C_{4-13}$ allenyl alcohol alkyl ether, $C_{4-13}$ allenyl alcohol alkylsulfonate ester, allenyl alcohol-o-hydroxyphenylsulfonate ester, allenyl alcohol-m-hydroxyphenylsulfonate ester, allenyl alcohol-p-hydroxyphenylsulfonate ester, and $C_{4-13}$ allenyl alcohol alkyl phosphate ester.

The above-mentioned allenyl alcohol derivative may be substituted further by any of $C_{1-20}$ alkyl group, phenyl group, o-halogenophenyl group, m-halogenophenyl group, and p-halogenophenyl group.

The above-mentioned halogen includes fluorine, chlorine, bromine, and iodine.

The aldehyde compound includes $C_{1-10}$ alkyl aldehyde, $C_{4-14}$ cycloalkyl aldehyde, $C_{2-14}$ cycloalkyl aldehyde, benzaldehyde, o-halogenobanzaldehyde, m-halogenobenzaldehyde, p-halogenobenzaldehyde, $C_{1-10}$ alkyl ester-substituted phenylaldehyde, o-halogenosuccinic aldehyde, m-halogenosuccinic aldehyde, p-halogenosuccinic aldehyde, p-halogenobenzaldehyde, furylaldehyde, and thiophene-aldehyde.

The ketone compound includes $C_{3-20}$ alkylketone, $C_{4-30}$ alkyl ester-substituted alkylketone, $C_{3-10}$ cycloalkylketone, acetophenone, tetralone, decalone, furylketone, and thiophenoketone.

The imine compound includes reaction products of the above-mentioned aldehyde compound and any of $C_{1-10}$ alkylamine, aniline, and benzylamine.

The hydrazone compound includes reaction products of the above-mentioned ketone compound and $C_{1-10}$ alkylhydrazine.

The olefin compound includes (substituted) allyl alcohol derivatives.

The (substituted) allyl alcohol derivative includes $C_{4-13}$ allyl alcohol alkyl ester and $C_{4-13}$ allyl alcohol alkyl carbamate.

The above-mentioned allyl alcohol derivative may be substituted further by any of $C_{1-20}$ alkyl group, phenyl group, o-halogenophenyl group, m-halogenophenyl group, and p-halogenophenyl group.

I. Reaction between an Acetylene Compound and a Compound Containing an Electrophilic Functional Group (1) Reaction between an acetylene compound and an aldehyde or ketone:

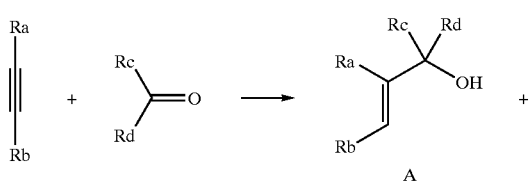

(where Ra, Rb, Rc, and Rd each denote an organic substituent group.)

The reaction product is allyl alcohol (A) and/or (B) as an adduct. The double bond is situated in two different positions depending on the substituent group. The double bond takes on the cis-form for Ra and Rb.

(2) Reaction between an acetylene compound and an imine:

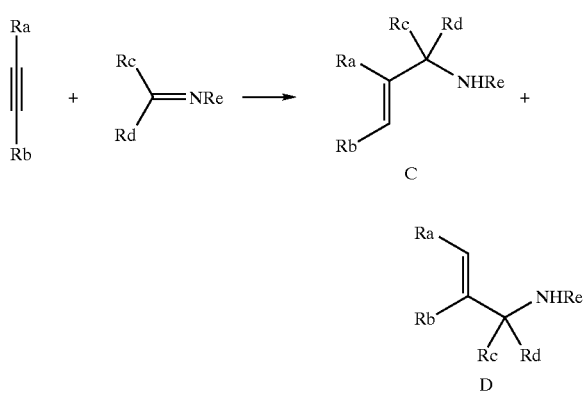

(where Ra, Rb, Rc, Rd, and Re each denote an organic substituent group; and Re may be metal such as lithium and magnesium.)

The reaction product is allylamine (C) and/or (D) as an adduct.

(3) Reaction between an acetylene compound and a hydrazone compound:

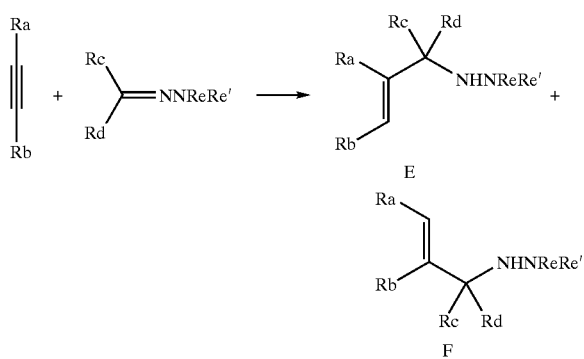

(where Ra, Rb, Rc, Rd, Re, and Re' each denote an organic substituent group.)

The reaction product is hydrazine (E) and/or (F) as an adduct.

(4) Reaction between an acetylene compound and an allyl compound:

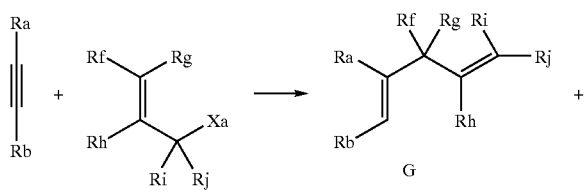

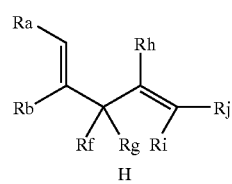

(where Ra, Rb, Rf, Rg, Rh, Ri, and Rj each denote an organic substituent group; and Xa denotes a halogen atom or a substituent hydroxyl group to be eliminated.)

The reaction product is diene (G) and/or (H) as an adduct with Xa eliminated.

(5) Reaction between an acetylene compound and a propargyl compound:

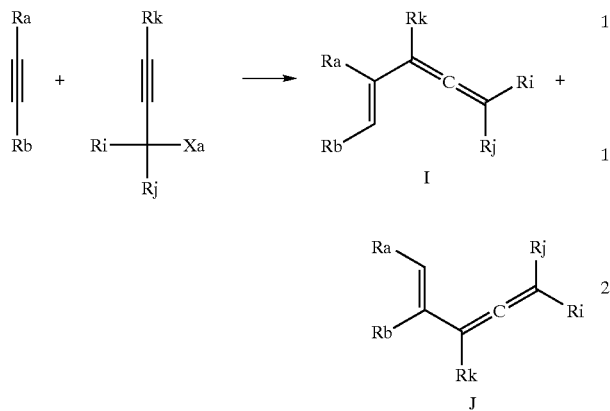

(where Ra, Rb, Rk, Ri, and Rj each denote an organic substituent group; and Xa denotes a halogen atom or a substituent hydroxyl group to be eliminated.)

The reaction product is allene (I) and/or (J) as an adduct with Xa eliminated.

(6) Reaction between a propargyl compound and an aldehyde or ketone:

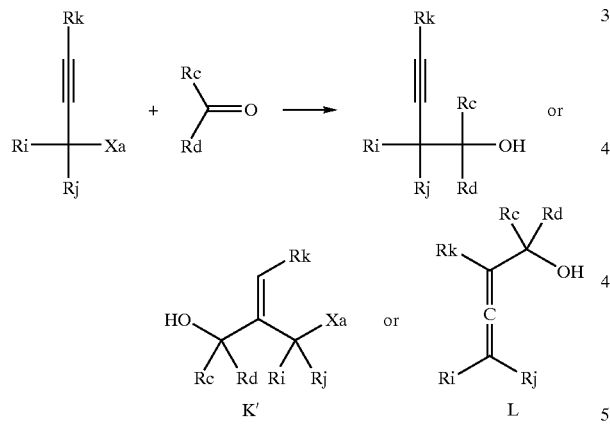

(where Rk, Ri, Rj, Rc, and Rd each denote an organic substituent group; and Xa denotes a halogen atom or a substituent hydroxyl group.)

In the case where Rk is a hydrogen atom at the terminal of the acetylene compound, the reaction product is acetylene (K). In the case where Rk is an organic substituent group other than hydrogen atom, or in the case where both Rc and Rd are hydrogen atoms, the reaction product is allene (L) with Xa eliminated. In the case where either of Rc and Rd is not a hydrogen atom, the reaction product is acetylene (K). In the case where Xa is a hydroxyl group which is protected by a protective group (and hence has a weak tendency to elimination), the main reaction product is (K') and the by-product is (L).

II. Reaction between an Olefin Compound and a Compound Having an Electrophilic Functional Group (1) Reaction between an allyl compound and an aldehyde or ketone:

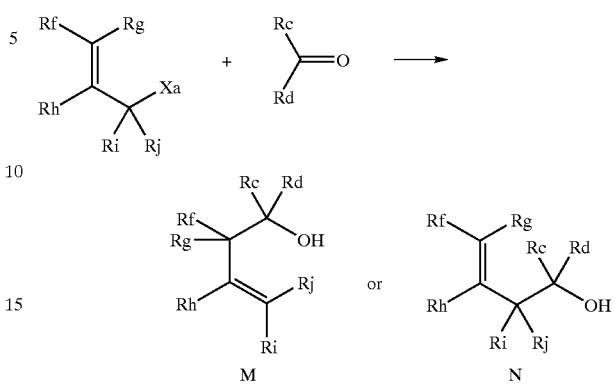

(where Rf, Rg, Rh, Ri, Rj, Rc, and Rd each denote an organic substituent group; and Xa denotes a halogen atom or a substituent hydroxyl group to be eliminated.)

The reaction product is alcohol (M) and/or (N) as an adduct with Xa eliminated.

(2) Reaction between an allyl compound and an imine compound:

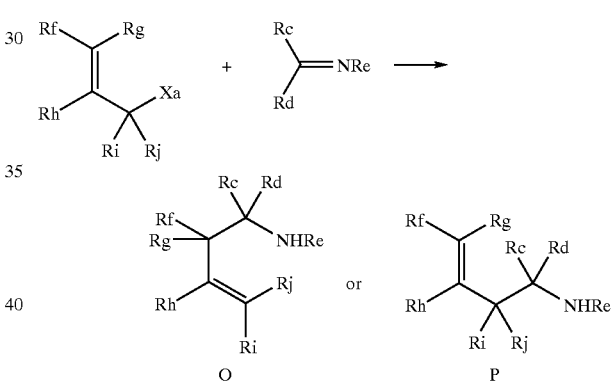

(where Rf, Rg, Rh, Ri, Rj, Rc, Rd, and Re each denote an organic substituent group; and Xa denotes a halogen atom or a substituent hydroxyl group to be eliminated.)

The reaction product is amine (O) and/or (P) as an adduct with Xa eliminated.

III. Reaction between an Allene Compound and a Compound Having an Electrophilic Functional Group (1) Reaction between an allene compound and an aldehyde or ketone:

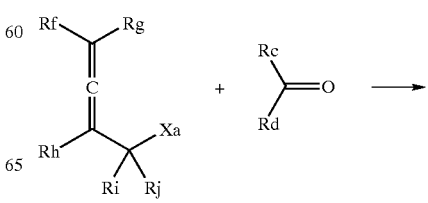

-continued

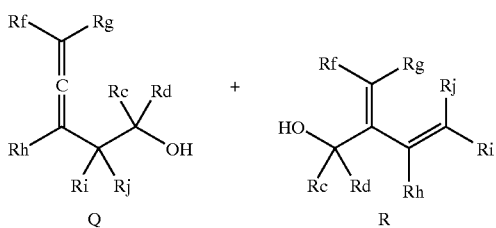

(where Rf, Rg, Rh, Ri, Rj, Rc, and Rd each denote an organic substituent group; and Xa denotes a halogen atom or a substituent hydroxyl group to be eliminated.)

The reaction product is allene (Q) and/or diene (R) as an adduct with Xa eliminated.

The above-mentioned reactions are followed by post-treatment which usually consists of adding water (as an electrophilic reagent) for replacement of the titanium group moiety by a hydrogen atom. If heavy water ($D_2O$) is added in place of water, there is obtained a compound having deuterium (D) in the molecule. If iodine is added, there is obtained a compound having iodine in the molecule. If water or heavy water (as an electrophilic reagent) is added in place of a compound having an electrophilic functional group, there is obtained a compound having a hydrogen atom or deuterium atom in the molecule through cyclization of the unsaturated bond. For example, an acetylene compound undergoes the following reactions.

IV. Reaction of a Compound Having in the Molecule Both an Unsaturated Bond and an Electrophilic Functional Group If in the above-mentioned reaction the titanium catalyst is acted on a compound having in the same molecule both an unsaturated bond and an electrophilic functional group, an intramolecular reaction takes place.

The compound having both an unsaturated bond and an electrophilic functional group may be one which has N, O, and S atoms in the carbon chain and also has a (substituted) $C_{1-5}$ alkylene group, (substituted) phenylene group, or heterocyclic group having an unsaturated bond at one end and an electrophilic functional group at the other end.

The above-mentioned alkylene group, phenylene group, and heterocyclic group may have a substituent group such as $C_{1-10}$ alkyl group, phenyl group, hydroxyl group, hydroxyl group for protection of substituted silyl group, $C_{8-15}$ aralkyloxyalkyl group, and $C_{3-17}$ ester group-substituted alkyl group. The heterocyclic group includes pyrrole and indole.

The unsaturated bond includes $C_{2-20}$ alkenyl group and $C_{2-20}$ alkynyl group.

The above-mentioned $C_{2-20}$ alkenyl group and $C_{2-20}$ alkynyl group may have a substituent group such as $C_{1-20}$ alkyl group, phenyl group, substituted silyl group, and alkyl or aromatic substituted tin group.

The functional group in the molecule includes double bond, triple bond, aldehyde group, ketone group, imino group, hydrazone group, $C_{1-10}$ carbamate group, $C_{1-10}$ acyl group, and $C_{2-11}$ ester group.

Typical reaction types are given below.

(1) In the case of a compound having two non-conjugated double bonds:

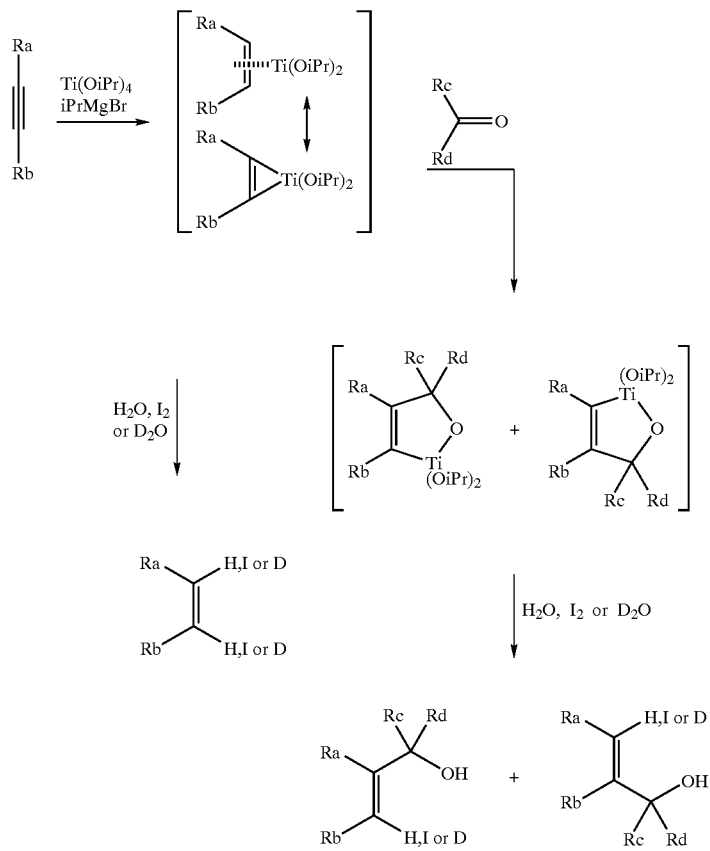

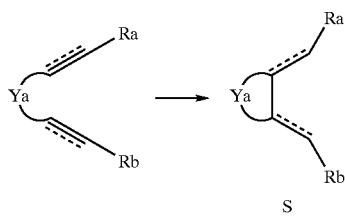

(where Ya denotes a substituted or unsubstituted alkylene group having 1–7 carbon atoms in the chain which may contain in the chain oxygen atoms, sulfur atoms, amino groups, phenylene groups, or heterocyclic groups; ≡ denotes a double bond or triple bond and = denotes a carbon-carbon single bond or double bond; and Ra and Rb are defined as above.)

The reaction gives rise to the cyclic compound (S) as the result of cyclization between the unsaturated bonds in the molecule. In the case where Rb is an ester group, there is obtained a cyclic ketone (T) or a cyclopropane (T') in which cyclization has proceeded further.

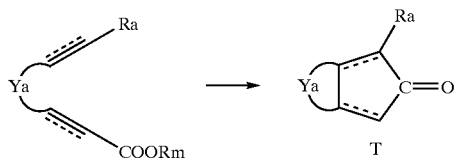

or

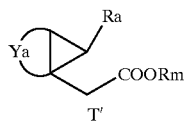

(where Ra, Ya, ≡, and = are defined as above; and Rm denotes a $C_{1-10}$ alkyl group, aralkyl group, Q alkenyl group, or allyl group.)

(2) In the case of a compound having an unsaturated bond and a carbonate group:

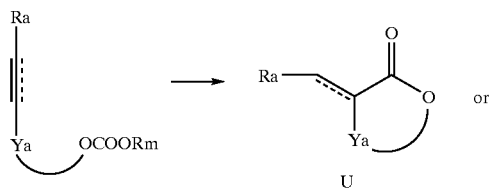

or

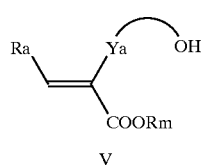

(where Ya, ≡, =, Ra, and Rm are defined as above.)

The reaction gives rise to a lactone compound (U) through cyclization in the molecule or an α,β-unsaturated ester (V). If the unsaturated bond is allene, the reaction product is a β,γ-unsaturated ester (V').

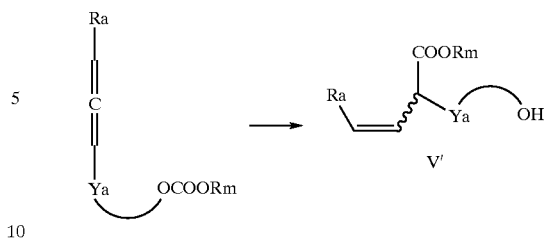

(where Ra, Rm, and Ya are defined as above.)

(3) In the case of a compound having both an unsaturated bond and an ester group:

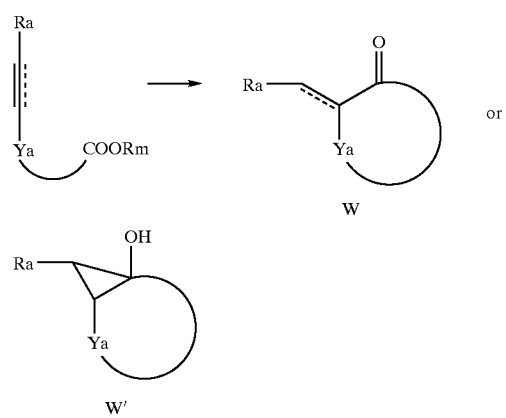

(where Ya, ≡, =, Ra, and Rm are defined as above.)

The reaction gives rise to a cyclic ketone compound (W) through cyclization in the molecule or a compound (W') through further cyclopropanization.

(4) In the case of a compound having both an unsaturated bond and an acyl group:
(a) In the case of a compound having both a triple bond and an acyl group:

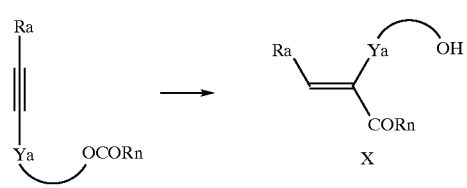

(where Ya is defined as above; Rn denotes a $C_{1-10}$ alkyl group, alkenyl group, or substituted or unsubstituted phenyl group; and Ra is defined as above.)

The reaction gives rise to an α,β-unsaturted ketone (X).
(b) In the case of a compound having both a double bond and an acyl group:

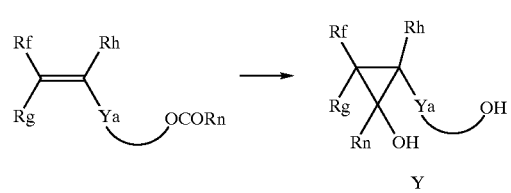

(where Rf, Rg, Rh, Ya, and Rn are defined as above.)

The reaction gives rise to a cyclopropane compound (Y).

(5) In the case of a compound having both a propargyl group or allyl group and an aldehyde group or ketone group:

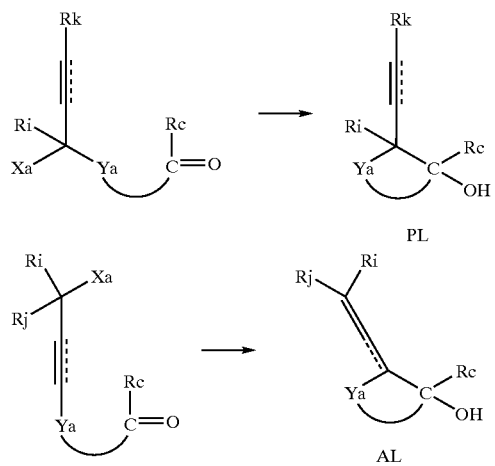

(where Rc, Ri, Rj, Rk, Xa, and Ya are defined as above.)

The reaction gives rise to an internally cyclized alcohol (PL) or (AL).

(6) In the case of a compound having both a propargyl group or allyl group and an imino group:

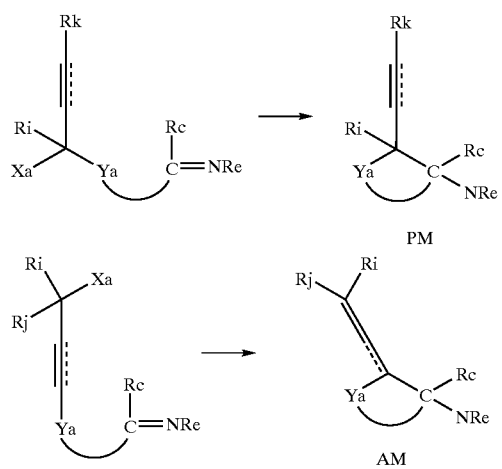

(where Rc, Re, Ri, Rj, Rk, Xa, and Ya are defined as above.)

The reaction gives rise to an internally cyclized amine (PM) or (AM).

V. Stepwise Reaction

The above-mentioned reaction by the titanium catalyst between a compound having an unsaturated bond and a compound having an electrophilic functional group or between an unsaturated bond and a compound having an electrophilic functional group may be followed by the adding of a compound having an electrophilic functional group in place of an electrophilic reagent (such as water). In this case there is obtained a compound resulting from the additional reaction of the compound having an electrophilic functional group on the titanium moiety. In other words, it is possible to carry out stepwise reactions. For example, in the case of IV-3, the additional reaction of aldehyde or ketone gives rise to a stepwise reaction product ($Z_B$) through an organic titanium intermediate ($Z_A$) as shown below.

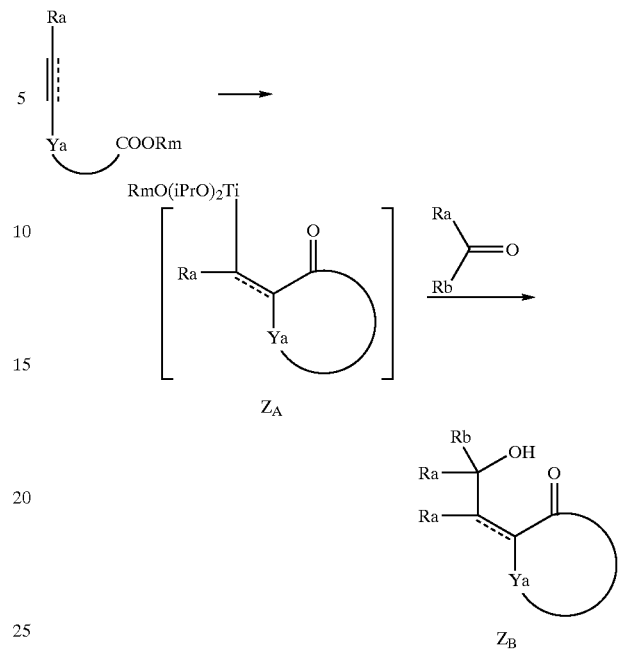

(where ≡, ═, Ra, Rb, Ya, and Rm are defined as above.)

VI. Other Reactions (1) Reaction between an imine compound and a compound having an electrophilic functional group:

The following formula represents the reaction in the case where the compound having an electrophilic functional group is aldehyde or ketone.

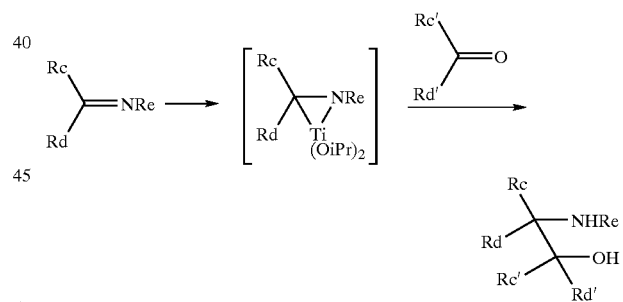

(where Rc, Rd, Rc', Rd', and Re each denote an organic substituent group; and Re may be a metal such as lithium and magnesium.)

This reaction gives rise to amino alcohol as an adduct through an adduct with the titanium catalyst.

Furthermore, if the titanium compound is one which has an asymmetric ligand as mentioned above, the reaction with the electrophilic functional group is the asymmetric reaction which gives rise to an optically active compound.

As a typical example, the reaction between an acetylene compound and an aldehyde or ketone that employs a catalyst of titanium compound having an asymmetric ligand gives rises to optically active allyl alcohols (A*) and (B*).

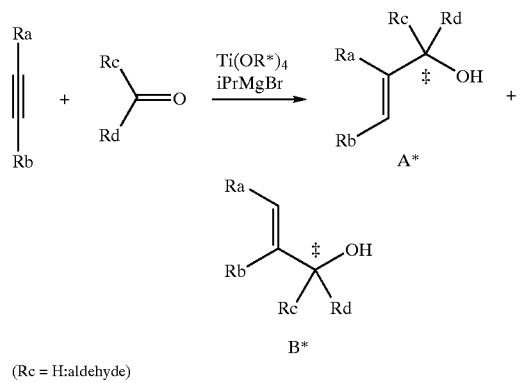

A*

B*

(Rc = H:aldehyde)

(where the asterisk (*) signifies the optical activity; Ra, Rb, Rc, and Rd are defined as above.)

In addition to the above-mentioned various reaction types, there are further another intramolecular and intermolecular reaction types depending on the combination of the unsaturated compound and the electrophilic functional group. Therefore, the present invention is of great use.

According to the present invention, the titanium catalyst and the organotitanium reacting reagent activate the carbon-carbon unsaturated bond whose activity is comparatively low, thereby catalyzing the reaction with the electrophilic functional group. They are inexpensive and industrially advantageous. The titanium catalyst and the organotitanium reacting reagent bring about the reaction between the carbon-carbon unsaturated bond and the electrophilic functional group, so that they give rise to a variety of addition reaction products from a compound having a carbon-carbon unsaturated bond and a compound having an electrophilic functional group in an industrially advantageous manner or they give rise to a variety of intramolecular addition reaction products of compounds having a carbon-carbon unsaturated bond and an electrophilic functional group in the same molecule.

Moreover, the titanium catalyst of the present invention eliminates the allyl group from the allyl-substituted maldnate ester derivative represented by the formula (3) below.

$$R^2R^3C{=}CR^4CH_2C(Ra)(COORb)_2 \quad (3)$$

(where $R^2$, $R^3$, and $R^4$ independently denote a hydrogen atom or a $C_{1\text{-}10}$ alkyl group; Ra denotes a $C_{1\text{-}20}$ substituted or unsubstituted alkyl group, alkenyl group, or aralkyl group; and Rb denotes a $C_{1\text{-}10}$ alkyl group or aralkyl group.)

This reaction can be used to produce in high yields the malonate ester derivative represented by the formula (4) below because the allyl group ($R^2R^3C{=}CR^4CH_2{-}$) functions as a protective group for the acid hydrogen atom of the malonate ester, thereby suppressing the side reactions.

$$RaCH(COORb)_2 \quad (4)$$

(where Ra denotes a $C_{1\text{-}20}$ substituted or unsubstituted alkyl group, alkenyl group, and aralkyl group; and Rb denotes a $C_{1\text{-}10}$ alkyl group or aralkyl group.)

Therefore, the eighth aspect of the present invention resides in a process for deallylating an allyl-substituted malonate ester represented by the formula (3) above in the presence of a titanium catalyst obtained from reaction between a titanium compound represented by the formula (1) above and a Grignard reagent represented by the formula (2) above (in a molar amount 1–10 times as much as the titanium compound), thereby giving a malonate ester derivative represented by the formula (4) above.

In this case, the allyl-substituted malonate ester represented by the formula (3) above can be obtained by monoallylating commercial malonate ester to give allylmalonate ester represented by the formula (5) below $$R^2R^3C{=}CR^4CH_2CH(COORb)_2 \quad (5)$$

(where $R^2$, $R^3$, and $R^4$ denote independently a hydrogen atom or a $C_{1\text{-}10}$ alkyl group; and Rb denotes a $C_{1\text{-}10}$ alkyl group or aralkyl group.) and further alkylating the ester.

In the above-mentioned formulas (3), (4), and (5), $R^2$, $R^3$, and $R^4$ denote independently a hydrogen atom or a $C_{1\text{-}10}$ alkyl group. It is desirable that all of them are hydrogen atoms. Examples of the alkyl group include methyl, ethyl, propyl, isopropyl, butyl, sec-butyl, t-butyl, hexyl, cyclohexyl, heptyl, octyl, nonyl, and decyl.

Ra denotes a $C_{1\text{-}20}$ substituted or unsubstituted alkyl group, alkenyl group, or aralkyl group. It includes, for example, methyl ethyl, propyl, isopropyl, butyl, sec-butyl, t-butyl, hexyl, cyclohexyl, heptyl, octyl, nonyl, benzyl, phenethyl, and naphthyl. They may have a double bond or a substituent group, such as halogen atom, ketone, ester, and ether. Rb denotes a $C_{1\text{-}10}$ alkyl group or aralkyl group. It includes, for example, methyl ethyl, propyl, isopropyl, butyl, sec-butyl, t-butyl, hexyl, cyclohexyl, heptyl, octyl, nonyl, benzyl, and phenethyl.

The alkylation of the acid hydrogen atom of the allylmalonate ester of formula (5) to give the allyl-substituted malonate ester of formula (3) may be accomplished by deprotonation with a common base and reaction with an alkylating reagent. Examples of the base include alkali metal hydride or alkaline earth metal hydride (such as sodium hydride and calcium hydride), alkali metal carbonate or alkaline earth metal carbonate (such as sodium carbonate and potassium carbonate), alkali metal hydroxide or alkaline earth metal hydroxide (such as sodium hydroxide and potassium hydroxide), alkyllithium (such as butyllithium), and organic base (such as pyridine, DBU, and triethylamine). On the other hand, the alkylating reagent is RaX, where Ra is defined as above; X is a group to be eliminated which includes halogen atoms (such as chlorine atom, bromine atom, and iodine atom) and substituted hydroxyl groups (such as tosyl, mesyl, and triflate). The reaction may be carried out in a homogeneous system (of ether, THF, or acetone) or in a two-phase system (of methylene chloride, toluene, basic aqueous solution, and phase transfer catalyst). The reaction temperature is usually −78° C. to 100° C. and the reaction time is usually 1 minute to 30 hours, depending on the conditions.

The allyl-substituted malonate ester derivative of the formula (3) synthesized as mentioned above is then deallylated by reaction with the titanium catalyst prepared as mentioned above. For the reaction of the allyl-substituted malonate ester of the formula (3) with the titanium catalyst, it is permissible to react the allyl-substituted malonate ester derivative with the previously prepared titanium catalyst, or to add the compounds of the formulas (1) and (2) to the allyl-substituted malonate ester derivative, thereby producing the titanium catalyst by reaction of the compounds of the formulas (1) and (2) in the deallylating reaction system.

The deallylating reaction may be carried out in the presence of a compound having an electrophilic functional group. Examples of the electrophilic functional group include aldehyde group, ketone group, imino group, hydrazone group, double bond, triple bond, acyl group, ester group, and carbonate group. Examples of the compound include aldehyde compound, ketone compound, imine compound, hydrazone compound, olefin compound, acetylene compound, acyl compound, ester compound, α,β-unsaturated carbonyl compound, and carbonate ester compound.

Examples of the aldehyde compound include $C_{1-10}$ alkyl aldehyde, $C_{4-14}$ cycloalkyl aldehyde, $C_{2-14}$ cycloalkenyl aldehyde, benzaldehyde, o-halogenobenzaldehyde, m-halogenobenzaldehyde, p-halogenobenzaldehyde, $C_{1-10}$ alkyl ester-substituted phenylaldehyde, o-halogenocinnamic aldehyde, m-halogenocinnamic aldehyde, p-halogenocinnamic aldehyde, p-halogenobenzaldehyde, furyl aldehyde, and thiophene aldehyde.

Examples of the ketone compound include $C_{3-20}$ alkyl ketone, $C_{4-30}$ alkyl ester-substituted alkyl ketone, $C_{3-10}$ cycloalkylketone, acetophenone, tetralone, decalone, furyl ketone, and thiophene ketone.

Examples of the imine compound include reaction products of the above-mentioned aldehyde compound with $C_{1-10}$ alkylamine, aniline, or benzylamine.

Examples of the hydrazone compound include reaction products of the above-mentioned ketone compound and $C_{1-10}$ alkylhydrazine.

Examples of the olefin compound include (substituted) allyl alcohol derivatives.

Examples of the (substituted) allyl alcohol derivative include $C_{4-13}$ allyl alcohol alkyl ester, and $C_{4-13}$ allyl alcohol alkyl carbamate.

The above-mentioned allyl alcohol derivative may be substituted further by a $C_{1-20}$ alkyl group, phenyl group, o-halogenophenyl group, m-halogenophenyl group, p-halogenophenyl group, etc.

The reaction should be carried out in an inert solvent, which is not specifically restricted so long as it is not involved in the reaction. Examples of the inert solvent include saturated hydrocarbons (such as hexane and heptane), aromatic hydrocarbons (such as benzene and toluene), ethers (such as diethyl ether, diisopropyl ether, t-butyl methyl ether, tetrahydrofuran, and dioxane), halogenated hydrocarbons (such as dichloromethane and dichloroethane), and mixtures thereof. For the reaction to be continuous with preparation of the titanium catalyst, it is desirable to use an ether solvent of the same kind. The reaction temperature ranges from −100° C. to the reflux temperature of the solvent, preferably from −78° C. to 0° C. The reaction time ranges from 1 minute to 20 hours, preferably from 10 minutes to 4 hours, depending on the reaction temperature. The amount of the titanium catalyst should be 0.01–5 equivalents, preferably 0.5–2.5 equivalents, per equivalent of the allyl-substituted malonate ester derivative. In the case where the deallylating reaction is carried out in the presence of a compound having an electrophilic functional group, the amount of the compound having an electrophilic functional group may be 0.5–2 equivalents, preferably 0.7–1.3 equivalents, per equivalent of the allyl-substituted malonate ester derivative. The reaction may be suspended by adding an electrophilic reagent, such as water, dilute hydrochloric acid, heavy water, chlorine, bromine, iodine, N-bromosuccimide, oxygen, carbon dioxide, and carbon monoxide.

The malonate ester derivative of the formula (5) obtained by the above-mentioned deallylating reaction may be used as such or may be further alkylated to give a disubstituted compound which, in turn, may be changed into a variety of monocarboxylic acid compounds by hydrolysis or decarbonation in the usual way.

The following formulas illustrate the process for producing the malonate ester derivative according to the present invention and the scheme for derivation.

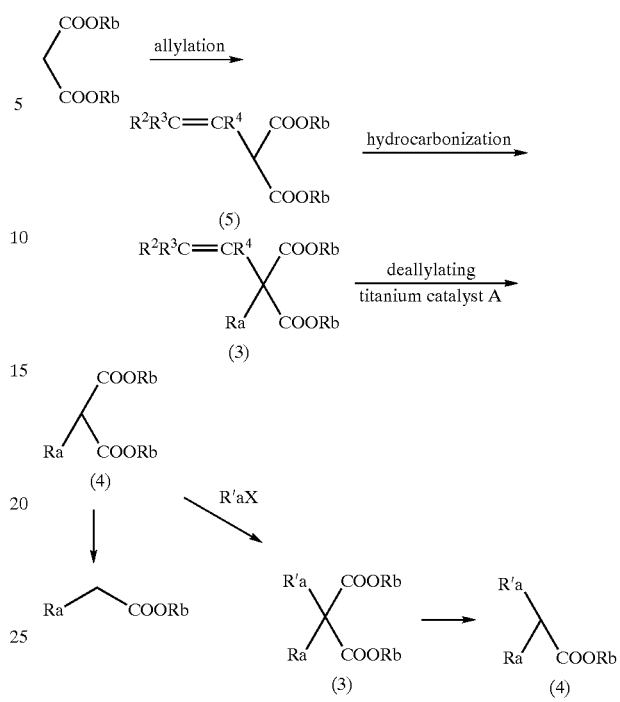

(where $R^2$, $R^3$, $R^4$, Ra, and Rb are defined as above; and R'a has the same meaning as Ra).

The present invention permits deallylation of the allyl-substituted malonate ester derivative of the formula (3) by the aid of a specific titanium catalyst. In this reaction it is possible to use the allyl group as a protective group for the acid hydrogen atom of the malonate ester. In this way it is possible to produce the desired malonate ester derivative of the formula (4) in high yields with less side reactions.

Since the malonate ester has its two acid hydrogen atoms easily deprotonated and alkylated, respectively, and also has its two carboxyl groups easily decarbonated, it can be made into a variety of derivatives as shown in the formulas below. Therefore, it is an important compound for organic synthesis. (A. C. Cope et al., Organic Reactions, John Wiley & Sons, New York, 1957, vol. 9, p. 107; H. O. House, Modern Synthetic Reactions, Benjamin, New York, 1972, p. 492; others)

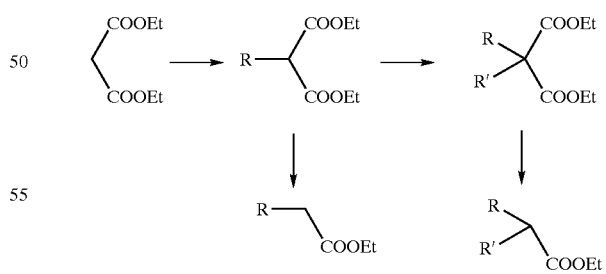

Since no adequate protective group for the acid hydrogen atom has been available (Protective Groups in Organic Chemistry, J. F. W. McOmie, Ed. Plenum Press, New York, 1973; T. W. Greene et al., Protective Groups in Organic Synthesis, John Wiley & Sons, New York, 1991; and others), there have been inevitable side reactions (such as dialkylation) in monoalkylation and limitations in reaction to change the monoalkyl compound into another compound.

(A. Brandstrom, Tetrahedron Lett., 1972, 473; G. Bram et al., J. Chem. Soc., Chem. Commun., 1979, 522; and others)

The titanium catalyst of the present invention solves the problems involved in the prior art technology, thereby permitting the industrial production of malonate ester derivatives through the above-mentioned deallylating reaction.

The invention will be described in more detail with reference to the following examples, which are not intended to restrict the scope of the invention. In the examples, Et denotes an ethyl group, i-Pr denotes an isopropyl group, Bu denotes a butyl group, 'Bu denotes a t-butyl group, Ph denotes a phenyl group, Ac denotes an acetyl group, Ts denotes a p-toluenesulfonyl group, TMS denotes a trimethylsilyl group, and OEE denotes an ethoxyethyloxy group. Unless otherwise stated, $^{1}$H-NMR means $^{1}$H-NMR (300 MHz, CDCl$_3$, δ (ppm)), $^{13}$C-NMR means $^{13}$C-NMR (75 MHz, CDCl$_3$, δ (ppm)), and IR means IR (NEAT).

EXAMPLE 1-1

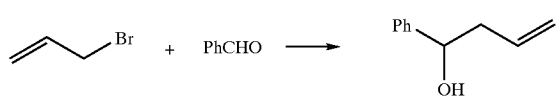

To 0.30 ml (1.0 mmol) of tetraisopropoxytitanium and 5 ml of ethyl ether solution containing allyl bromide (1.0 mmol) was added dropwise at −50° C. 1.67 ml of 1.2M ethyl ether solution containing isopropylmagnesium bromide (2.0 mmol). Upon stirring at −50° C. to −40° C. for 1 hour, the reaction liquid turned from yellow into brown. To the reaction liquid was added 0.071 ml (0.7 mmol) of benzaldehyde at −45° C. to −40° C. The temperature was raised to −10° C. to 0° C. over 30 minutes. With 5 ml of 1N hydrochloric acid added, the solution was heated to room temperature and separated into layers. The organic layer was washed with a saturated aqueous solution of sodium hydrogen carbonate. After drying with anhydrous magnesium sulfate, the solution was freed of solvent by vacuum distillation. The residues were purified by silica gel chromatography. Thus there was obtained 97 mg of 1-phenyl-3-buten-1-ol (94% yields based on benzaldehyde).

EXAMPLES 1-2 TO 1-14

The procedure of Example 1-1 was repeated except that the allyl bromide, tetraisopropoxytitanium, and isopropylmagnesium bromide were replaced by those compounds shown in Table 1. There was obtained 1-phenyl-3-buten-1-ol in different yields as shown in Table 1.

TABLE 1

| Example | Allyl compound | Titanium compound | Grignard reagent | Yields of 1-phenyl-3-buten-1-ol (%) |
| --- | --- | --- | --- | --- |
| 1-1 | X = Br | Ti(O-i-Pr)$_4$ | i-PrMgBr | 94 |
| 1-2 | Br | ClTi(O-i-Pr)$_3$ | i-PrMgBr | 92 |
| 1-3 | Br | Cl$_2$Ti(O-i-Pr)$_2$ | i-PrMgBr | 12 |
| 1-4 | Br | TiCl$_4$ | i-PrMgBr | 20 |

TABLE 1-continued

| Example | Allyl compound | Titanium compound | Grignard reagent | Yields of 1-phenyl-3-buten-1-ol (%) |
| --- | --- | --- | --- | --- |
| 1-5 | Br | Ti(O-i-Pr)$_4$ | i-PrMgCl | 93 |
| 1-6 | Br | Ti(O-i-Pr)$_4$ | EtMgBr | 72 |
| 1-7 | Br | Ti(O-i-Pr)$_4$ | n-PrMgBr | 93 |
| 1-8 | I | Ti(O-i-Pr)$_4$ | i-PrMgBr | 96 |
| 1-9 | Cl | Ti(O-i-Pr)$_4$ | i-PrMgBr | 92 |
| 1-10 | OAc | Ti(O-i-Pr)$_4$ | i-PrMgBr | 61 |
| 1-11 | OC(O)OEt | Ti(O-i-Pr)$_4$ | i-PrMgBr | 74 |
| 1-12 | OPh | Ti(O-i-Pr)$_4$ | i-PrMgBr | 89 |
| 1-13 | OTs | Ti(O-i-Pr)$_4$ | i-PrMgBr | 57 |
| 1-14 | OP(O)(OEt)$_2$ | Ti(O-i-Pr)$_4$ | i-PrMgBr | 83 |

EXAMPLE 1-15

To 0.90 ml (3.0 mmol) of tetraisopropoxytitanium and 5 ml of n-butyl ether solution containing allyl bromide (3.0 mmol) was added dropwise at −78° C. 6.2 ml of 0.97M n-butyl ether solution containing isopropylmagnesium bromide (6.0 mmol). After stirring at −50° C. to −40° C. for 1 hour, the reaction liquid was given 0.21 ml (2.1 mmol) of benzaldehyde and heated to 0° C. over 30 minutes. With 10 ml of 3N hydrochloric acid added, the solution was heated to room temperature and separated into layers. The organic layer was washed with a saturated aqueous solution of sodium hydrogen carbonate. After drying with anhydrous magnesium sulfate, the solution was freed of solvent by vacuum distillation. The residues were purified by silica gel chromatography. Thus there was obtained 252 mg of 1-phenyl-3-buten-1-ol (81% yields based on benzaldehyde).

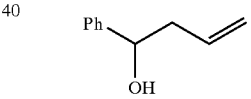

$^{1}$H-NMR, δ: 2.42–2.51 (m, 2H) 2.56 (br s, 1H) 4.63 (t, J=6.4 Hz, 1H) 5.04–5.19 (m, 2H) 5.67–5.84 (m, 1H) 7.18–7.39 (m, 5H)

$^{13}$C-NMR, δ: 43.7, 73.3, 118.2, 125.8, 127.4, 128.3, 134.4, 143.8

EXAMPLES 2-1 TO 2-21

The procedure of Example 1-1 was repeated except that the allyl bromide and benzaldehyde were replaced by those compounds shown in Tables 2 and 3. There were obtained corresponding allyl alcohols in yields as shown in Tables 2 and 3.

TABLE 2

| Example | Allyl compound | Aldehyde or ketone | Reaction product | Yields (%) (anti:syn) |
|---|---|---|---|---|
| 2-1 | allyl-Br | m-Br-PhCHO | m-Br-Ph-CH(OH)-CH2-CH=CH2 | 80 |
| 2-2 | allyl-Br | p-MeO2C-PhCHO | p-MeO2C-Ph-CH(OH)-CH2-CH=CH2 | 77 |
| 2-3 | allyl-Br | n-C5H11CHO | nC5H11-CH(OH)-CH2-CH=CH2 | 87 |
| 2-4 | allyl-Br | Ph-CH=CH-CHO | Ph-CH=CH-CH(OH)-CH2-CH=CH2 | 88 |
| 2-5 | allyl-Br | PhC(O)CH3 | Ph-C(CH3)(OH)-CH2-CH=CH2 | 85 |
| 2-6 | allyl-Br | n-butyl methyl ketone | tertiary alcohol with allyl | 82 |
| 2-7 | allyl-Br | 2-tetralone | 2-allyl-2-hydroxy-tetralin | 92 |
| 2-8 | allyl-Br | PhCHO + PhC(O)CH3 | Ph-CH(OH)-CH2-CH=CH2 (84) + Ph-C(CH3)(OH)-CH2-CH=CH2 (16) | 91 |
| 2-9 | CH3-CH=CH-CH2-OC(O)OEt | PhCHO | Ph-CH(OH)-CH(CH3)-CH=CH2 | 50 (75:25) |
| 2-10 | CH2=CH-CH(CH3)-OC(O)OEt | PhCHO | Ph-CH(OH)-CH(CH3)-CH=CH2 | 74 (75:25) |

TABLE 3

| Example | Allyl compound | Aldehyde or ketone | Reaction product | Yields (%), (anti:syn) |
|---|---|---|---|---|
| 2-11 | Ph-CH=CH-CH2-OC(O)OEt | PhCHO | Ph-CH(OH)-CH(Ph)-CH=CH2 | 23 (>97:3) |
| 2-12 | CH2=CH-CH(Ph)-OC(O)OEt | PhCHO | Ph-CH(OH)-CH(Ph)-CH=CH2 | 73 (>97:3) |

TABLE 3-continued

| Example | Allyl compound | Aldehyde or ketone | Reaction product | Yields (%), (anti:syn) |
|---|---|---|---|---|
| 2-13 | (3-methyl-2-butenyl OC(O)OEt) | PhCHO | Ph-CH(OH)-C(Me)2-CH=CH2 | 12 |
| 2-14 | (1,1-dimethyl-2-propenyl OC(O)OEt) | PhCHO | | 56 |
| 2-15 | (2-methylallyl OC(O)OEt) | PhCHO | Ph-CH(OH)-CH2-C(Me)=CH2 | 84 |
| 2-16 | (1-(p-Br-Ph)allyl OC(O)OEt) | PhCHO | p-Br-Ph-CH(Ph)-CH(OH)-CH=CH2 | 83 (>97:3) |
| 2-17 | (1-((CH2)6OAc)allyl OC(O)OEt) | PhCHO | Ph-CH(OH)-CH((CH2)6OAc)-CH=CH2 | 78 (77:23) |
| 2-18 | (3-bromocyclooctene) | EtCHO | cyclooctenyl-CH(OH)-Et | 84 |
| 2-19 | (3-OCO2Et-cyclooctene) | EtCHO | cyclooctenyl-CH(OH)-Et | 98 |
| 2-20 | Me-CH(N(CH2Ph)2)-CH(OCO2Et)-CH=CH2 | EtCHO | Me-CH(N(CH2Ph)2)-CH(-)-CH(OH)-Et | 88 |
| 2-21 | Ph-CH(N(CH2Ph)2)-CH(OCO2Et)-CH=CH2 | PhCHO | Ph-CH(N(CH2Ph)2)-CH(-)-CH(OH)-Ph | 67 |

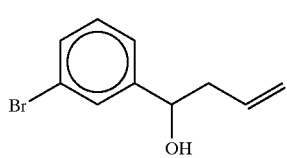

¹H-NMR, δ: 2.22 (br s, 1H) 2.35–2.56 (m, 2H) 4.67 (t, J=6.4 Hz, 1H) 5.09–5.20 (m, 2H) 5.68–5.85 (m, 1H) 7.15–7.28 (m, 2H) 7.39 (dt, J=7.5, 1.7 Hz, 1H) 7.50 (s, 1H)

¹³C-NMR, δ: 43.7, 72.4, 118.9, 122.5, 124.4, 128.9, 129.9, 130.5, 133.8, 146.1

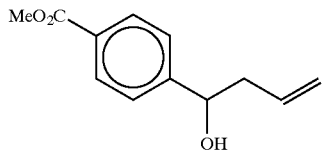

¹H-NMR, δ: 2.39–2.55 (m, 2H) 2.99 (br s, 1H) 3.87 (s, 3H) 4.75 (t, J=6.5 Hz, 1H) 5.06–5.15 (m, 2H) 5.67–5.83 (m, 1H) 7.38 (d, J=8.4 Hz, 2H) 7.95 (d, J=8.4 Hz, 2H)

¹³C-NMR, δ: 43.5, 51.9, 72.7, 118.4, 125.6, 128.9, 129.5, 133.8, 149.1, 166.9

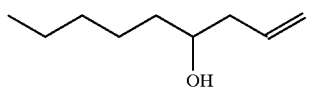

¹H-NMR, δ: 0.88 (t, J=6.6 Hz, 3H) 1.18–1.52 (m, 8H) 1.72 (br s, 1H) 2.05–2.35 (m, 2H) 3.57–3.68 (m, 1H) 5.07–5.17 (m, 2H) 5.74–5.89 (m, 1H)

¹³C-NMR, δ: 14.0, 22.6, 25.3, 31.8, 36.7, 41.9, 70.7, 117.9, 134.9

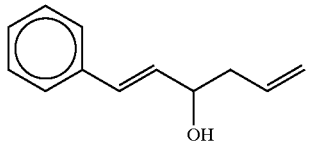

¹H-NMR, δ: 1.93 (br s, 1H) 2.32–2.50 (m, 2H) 4.35 (ddt, J=1.0, 6.3, 5.6 Hz, 1H) 5.12–5.23 (m, 2H) 5.77–5.93 (m, 1H) 6.23 (dd, J=6.3, 15.9 Hz, 1H) 6.60 (dd, J=1.0, 15.9 Hz, 1H) 7.19–7.40 (m, 5H)

¹³C-NMR, δ: 41.9, 71.7, 118.4, 126.4, 127.6, 128.5, 130.3, 131.5, 134.0, 136.6

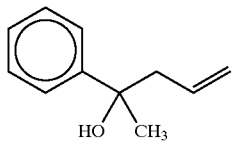

¹H-NMR, δ: 1.53 (s, 3H) 2.22 (br s, 1H) 2.48 (dd, J=8.3, 13.7 Hz, 1H) 2.67 (dd, J=6.5, 13.7 Hz, 1H) 5.06–5.15 (m, 2H) 5.53–5.68 (m, 1H) 7.16–7.46 (m, 5H)

¹³C-NMR, δ: 29.7, 48.4, 73.6, 119.3, 124.7, 126.5, 128.1, 133.6, 147.5

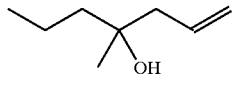

¹H-NMR, δ: 0.89 (t, J=7.0 Hz, 3H) 1.14 (9, 3H) 1.20–1.48 (m, 6H) 1.61 (br s, 1H) 2.20 (d, J=7.1 Hz, 2H) 5.04–5.14 (m, 2H) 5.76–5.93 (m, 1H)

¹³C-NMR, δ: 14.0, 23.2, 26.0, 26.6, 41.5, 46.2, 72.1, 118.4, 134.1

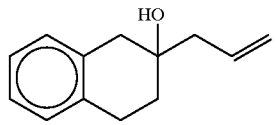

¹H-NMR, δ: 1.67–1.87 (m, 2H) 1.96 (br s, 1H) 2.28 (d, J=7.4 Hz, 2H) 2.66–3.03 (m, 4H) 5.06–5.19 (m, 2H) 5.84–6.01 (m, 1H) 6.96–7.20 (m, 4H)

¹³C-NMR, δ: 26.0, 33.5, 41.5, 45.5, 70.3, 118.8, 125.7, 125.8, 128.5, 129.4, 133.3, 134.3, 135.3

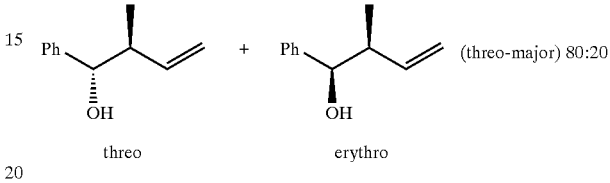

¹H-NMR, δ: 0.87 (d, J=6.8 Hz, 2H) 1.01 (d, J=6.8 Hz, 2H) 2.42–2.54 (m, 1H) 2.52–2.64 (m, 1H) 4.36 (d, J=7.9 Hz, 1H) 4.62 (d, J=5.5 Hz, 1H) 5.01–5.26 (m, 2H) 5.69–5.89 (m, 1H) 7.22–7.45 (m, 5H)

¹³C-NMR, δ:
(threo) 16.4, 46.1, 77.8, 116.6, 126.8, 127.5, 128.1, 140.6, 142.4
(erythro) 14.0, 44.6, 77.2, 115.4, 126.5, 127.2, 128.0, 140.3, 142.5

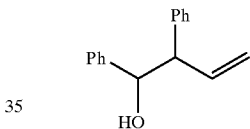

¹H-NMR, δ: 2.37 (br s, 1H) 3.48–3.58 (m, 1H) 4.82 (d, J=4.5 Hz, 1H) 5.15–5.28 (m, 2H) 6.16–6.31 (m, 1H) 6.98–7.37 (m, 10H)

¹³C-NMR, δ: 58.9, 76.8, 118.1, 126.3, 126.4, 127.1, 127.6, 128.1, 137.6, 140.4, 141.6

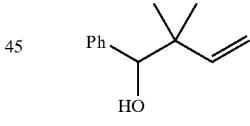

¹H-NMR, δ: 0.96 and 1.01 (2s, 6H) 2.08 (br s, 1H) 4.41 (s, 1H) 5.08 (d, J=19.5 Hz, 1H) 5.13 (d, J=16.5 Hz, 1H) 5.92 (dd, J=16.5, 19.5 Hz, 1H) 7.20–7.40 (m, 5H)

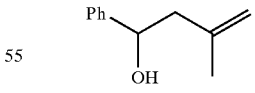

¹H-NMR, δ: 1.78 (s, 3H) 2.21 (br s, 1H) 2.41 (d, J=4.5 Hz, 2H) 4.79 (t, J=4.5 Hz, 1H) 4.84 and 4.91 (2br s, 2H) 7.22–7.40 (m, 5H)

¹³C-NMR, δ: 22.3, 48.1, 71.5, 113.8, 125.7, 127.3, 128.2, 142.2, 144.0

Reaction Product in Example 2-18

¹H-NMR: 0.95 (t, J=7.4 Hz, 3H) 1.08–1.75 (m, 11H) 1.77–1.90 (m, 1H) 1.98–2.10 (m, 1H) 2.13–2.29 (m, 1H) 2.46–2.60 (m, 1H) 3.39 (dt, J₁=3.2 Hz, J₂=7.9 Hz, 1H) 5.27 (dd, J₁=J₂=9.1 Hz, 1H) 5.69 (dt, J₁=9.1 Hz, J₂=8.9 Hz, 1H)

Reaction Product in Example 2-19

$^1$H-NMR: 0.95 (t, J=7.4 Hz, 3H) 1.12–1.80 (m, 13H) 1.98–2.11 (m, 1H) 2.13–2.29 (m, 1H) 2.50–2.62 (m, 1H) 3.33 (dt, $J_1$=3.0 Hz, $J_2$=7.9 Hz, 1H) 5.21 (dd, $J_1$=$J_2$=10.3 Hz) 5.59 (ddd, $J_1$=7.2 Hz, $J_2$=$J_3$=10.3 Hz, 1H)

Reaction Product in Example 2-20

$^1$H-NMR: 2.98 (d, J=13.5 Hz, 2H) 3.00–3.09 (m, 1H) 3.86 (d, J=13.3 Hz, 2H) 4.16 (d, J=11.0 Hz, 1H) 4.35–4.47 (m, 1H) 4.63 (dd, J=1.8, 17.3 Hz, 1H) 5.21 (dd, J=1.8, 10.3 Hz, 1H) 6.03 (dt, J=9.9, 17.2 Hz, 1H) 7.00–7.55 (m, 20H)

Reaction Product in Example 2-21

$^1$H-NMR: 0.81 (t, J=7.2 Hz, 3H) 1.04 (d, J=6.6 Hz, 3H) 0.87–1.18 (m, 2H) 2.35 (dt, J=2.9, 10.0 Hz, 1H) 2.83–2.94 (m, 1H) 3.28 (d, J=13.0 Hz, 26) 3.82 (d, J=13.0 Hz, 26) 3.82–3.88 (m, 1H) 4.97–5.06 (m, 2H) 5.46 (dt, J=16.5, 10.1 Hz, 1H) 7.20–7.41 (m, 10H)

EXAMPLE 3-1

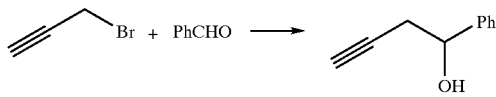

To 0.425 ml (1.43 mmol) of tetraisopropoxytitanium and 10 ml of ethyl ether solution of propargyl bromide (0.127 ml, 1.43 mmol) was added dropwise at −50° C. 1.90 ml of 1.43M ethyl ether solution containing isopropylmagnesium bromide (2.72 mmol). After stirring at −50° C. to −40° C. for 1 hour, the reaction liquid was given 0.102 ml (1.0 mmol) of benzaldehyde at −40° C. and heated to −20° C. over 30 minutes. With 1N hydrochloric acid added, the solution was heated to room temperature and separated into layers. The organic layer was washed with a saturated aqueous solution of sodium hydrogen carbonate. After drying with anhydrous magnesium sulfate, the solution was freed of solvent by vacuum distillation. The residues were purified by silica gel chromatography. Thus there was obtained 124 mg of 4-phenyl-1-butyn-4-ol (85% yields based on benzaldehyde).

EXAMPLES 3-2 TO 3-21

The procedure of Example 3-1 was repeated except that the propargyl bromide and benzaldehyde were replaced by those compounds shown in Tables 4 and 5. There were obtained corresponding allyl alcohols in yields as shown in Tables 4 and 5.

TABLE 4

| Example | Propargyl compound | Aldehyde | Reaction product | Yields (%) (anti:syn) |
|---|---|---|---|---|
| 3-1 | ≡–CH$_2$–Br | PhCHO | ≡–CH$_2$–CH(OH)–Ph | 85 |
| 3-2 | ≡–CH$_2$–Cl | PhCHO | ≡–CH$_2$–CH(OH)–Ph | 82 |
| 3-3 | ≡–CH$_2$–OC(O)OEt | PhCHO | ≡–CH$_2$–CH(OH)–Ph | 74 |
| 3-4 | ≡–CH$_2$–OAc | PhCHO | ≡–CH$_2$–CH(OH)–Ph | 36 |
| 3-5 | ≡–CH$_2$–Br | C$_8$H$_{17}$CHO | ≡–CH$_2$–CH(OH)–C$_8$H$_{17}$ | 91 |
| 3-6 | ≡–CH$_2$–Br | p-BrPhCHO | ≡–CH$_2$–CH(OH)–Ph-p-Br | 91 |
| 3-7 | ≡–CH$_2$–Br | p-MeO$_2$CPhCHO | ≡–CH$_2$–CH(OH)–Ph-p-CO$_2$Me | 86 |
| 3-8 | ≡–CH$_2$–Br | Ph–CH=CH–CHO | ≡–CH$_2$–CH(OH)–CH=CH–Ph | 74 |

TABLE 4-continued

| Example | Propargyl compound | Aldehyde | Reaction product | Yields (%) (anti:syn) |
|---|---|---|---|---|
| 3-9 | HC≡C-CH2-Br | C7H15-C(O)-CH3 | HC≡C-CH2-C(C7H15)(CH3)(OH) | 85 |
| 3-10 | HC≡C-CH2-Br | BuC(O)Bu | HC≡C-CH2-C(Bu)(Bu)(OH) | 78 |
| 3-11 | CH3-C≡C-CH2-Br | PhCHO | CH2=C=C(CH3)-CH(Ph)(OH) | 89 |

TABLE 5

| Example | Propargyl compound | Aldehyde | Reaction product | Yields (%), (anti:syn) |
|---|---|---|---|---|
| 3-12 | CH3-C≡C-CH2-Br | C7H15-C(O)-CH3 | CH2=C=C(CH3)-C(C7H15)(CH3)(OH) | 83 |
| 3-13 | TMS-C≡C-CH2-Br | PhCHO | CH2=C=C(TMS)-CH(Ph)(OH) | 83 |
| 3-14 | TMS-C≡C-CH2-Br | p-MeO2CPhCHO | CH2=C=C(TMS)-CH(Ph-p-CO2Me)(OH) | 79 |
| 3-15 | Ph-C≡C-CH2-Br | PhCHO | CH2=C=C(Ph)-CH(Ph)(OH) | 86 |
| 3-16 | TMS-C≡C-CH(C5H11)-OC(O)OEt | C5H11CHO | TMS-C≡C-CH(C5H11)-CH(C5H11)(OH) | 70 (80:20) |
| 3-17 | TMS-C≡C-CH(C5H11)-OAc | C5H11CHO | TMS-C≡C-CH(C5H11)-CH(C5H11)(OH) | 77 (80:20) |
| 3-18 | TMS-C≡C-CH(C3H6OC(O)OEt)-OC(O)OEt | C5H11CHO | TMS-C≡C-CH(C3H5OC(O)OEt)-CH(C5H11)(OH) | 88 (76:24) |

TABLE 5-continued

| Example | Propargyl compound | Aldehyde | Reaction product | Yields (%), (anti:syn) |
|---|---|---|---|---|
| 3-19 | 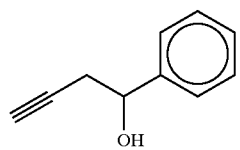 | C₅H₁₁CHO | 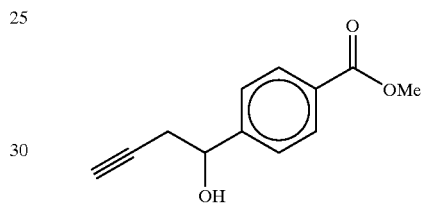 | 89 (75:25) |
| 3-20 | C₆H₁₃—≡—CH(C₂H₅)—OC(O)OEt | C₅H₁₁CHO | C₆H₁₃—≡—CH(C₂H₅)—CH(OH)—C₅H₁₁ | 89 (72:28) |
| 3-21 | TMS—≡—C(CH₃)₂—OC(O)OEt | PhCHO | TMS—≡—C(CH₃)₂—CH(OH)—Ph | 78 |

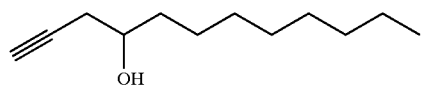

¹H-NMR, δ: 2.06 (t, J=2.6 Hz, 1H) 2.62 (dd, J=2.6 Hz, 6.4 Hz, 2H) 4.84 (t, J=6.3 Hz, 1H) 7.2–7.4 (m, 5H)

¹³C-NMR, δ: 29.3, 70.9, 72.2, 80.6, 125.7, 127.9, 128.4, 142.4

IR: 695, 750, 855, 1045, 1245, 1450, 1495, 1600, 1710, 1945, 2110, 2915, 3280, 3350 (cm⁻¹)

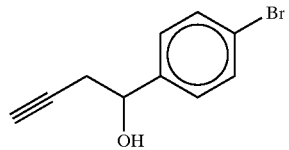

¹H-NMR, δ: 0.85 (t, J=6.7 Hz, 3H) 1.1–1.4 (m, 12H) 1.50 (t, J=6.8 Hz, 2H) 2.02 (t, J=2.6 Hz, 1H) 2.20 (bs, 1H) 2.34 (m, 2H) 3.72 (quinted, J=6.0 Hz, 1H)

¹³C-NMR, δ: 14.0, 22.6, 25.5, 27.6, 29.2, 29.5, 31.8, 36.2, 69.8, 70.6, 80.9

IR: 845, 1065, 1120, 1250, 1455, 1710, 2115, 2850, 2890, 3295, 3340 (cm⁻¹)

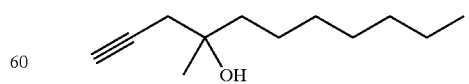

¹H-NMR, δ: 2.07 (t, J=2.6 Hz, 1H) 2.59 (dd, J=2.6 Hz, 6.6 Hz, 2H) 2.73 (bs, 1H) 4.80 (t, J=6.3 Hz, 1H) 7.24 (d, J=8.7 Hz, 2H) 7.47 (d, J=8.5 Hz, 2H)

¹³C-NMR, δ: 29.3, 71.4, 80.1, 121.7, 127.4, 131.5, 141.3

IR: 760, 820, 1005, 1055, 1190, 1255, 1400, 1485, 1590, 1700, 1745, 2100, 2880, 3275, 3360 (cm⁻¹)

¹H-NMR, δ: 2.07 (t, J=2.6 Hz, 1H) 2.64 (dd, J=1.6 Hz, 6.8 Hz, 2H) 3.00 (bs, 1H), 3.89 (s, 3H) 4.91 (bs, 1H) 7.45 (d, J=8.3 Hz) 7.99 (d, J=8.2 Hz)

¹³C-NMR, δ: 29.3, 52.0, 71.3, 71.7, 80.0, 125.7, 129.6, 147.5, 166.8

IR: 700, 765, 855, 960, 1015, 1055, 1105, 1180, 1265, 1440, 1570, 1615, 1710, 1930, 2120, 2920, 3280, 3410 (cm⁻¹)

¹H-NMR, δ: 2.08 (t, J=2.7 Hz, 1H) 2.54 (ddd, J=2.1 Hz, 3.0 Hz, 5.8 Hz, 2H) 2.69 (bs, 1H) 4.45 (q, J=6.1 Hz, 1H) 6.27 (dd, J=6.3 Hz, 15.9 Hz, 1H) 6.64 (d, J=15.9 Hz, 1H)

¹³C-NMR, δ: 27.6, 70.6, 71.0, 80.2, 126.5, 127.8, 128.5, 129.9, 131.2, 136.3

IR: 690, 750, 850, 970, 1035, 1100, 1265, 1420, 1450, 1500, 1600, 1710, 2130, 2810, 3025, 3290, 3370 (cm⁻¹)

¹H-NMR, δ: 0.85 (t, J=6.7 Hz, 3H) 1.26 (s, 3H) 1.2–1.4 (m, 10H) 1.49–1.59 (m, 2H) 1.94 (bs, 1H) 2.04 (t, J=2.7 Hz, 1H) 2.33 (d, J=1.5 Hz, 2H)

¹³C-NMR, δ: 14.0, 22.6, 23.9, 26.2, 29.2, 30.0, 31.7, 32.3, 41.1, 71.1, 71.6, 80.9

IR: 775, 910, 950, 1050, 1270, 1385, 1470, 1720, 2140, 2870, 2925, 3315, 3365 (cm$^{-1}$)

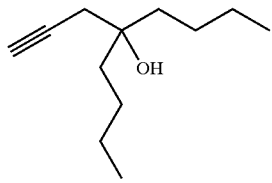

$^1$H-NMR, δ: 1.14 (t, J=6.8 Hz, 6H) 1.2–1.4 (m, 8H) 1.4–1.6 (m, 4H) 1.81 (bs, 1H) 2.01 (t, J=2.7 Hz, 1H) 2.31 (d, J=2.6 Hz, 2H)

$^{13}$C-NMR, δ: 13.9, 23.1, 25.6, 30.1, 38.3, 70.9, 73.3, 80.8

IR: 845, 1005, 1135, 1260, 1385, 1455, 1715, 1750, 2120, 2865, 2970, 3300, 3400 (cm$^{-1}$)

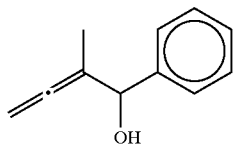

$^1$H-NMR, δ: 1.55 (t, J=3.1 Hz, 3H) 2.49 (d, J=3.8 Hz, 1H) 4.87 (m, 2H) 5.07 (bs, 1H) 7.2–7.4 (m, 5H)

$^{13}$C-NMR, δ: 14.4, 74.6, 77.5, 102.5, 126.4, 127.6, 128.2, 141.8, 204.8

IR: 695, 730, 845, 1015, 1165, 1365, 1440, 1495, 1595, 1955, 2910, 3340 (cm$^{-1}$)

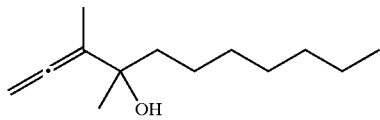

$^1$H-NMR, δ: 0.86 (t, J=6.7 Hz, 3H) 1.20–1.31 (m, 10H) 1.28 (s, 3H) 1.49–1.59 (m, 2H) 1.69 (t, J=3.2 Hz) 1.79 (bs, 1H) 4.76 (q, J=3.1 Hz)

$^{13}$C-NMR, δ: 14.1, 14.6, 22.7, 24.0, 27.1, 29.3, 30.0, 31.9, 40.4, 77.0, 105.8, 204.4

IR: 845, 925, 1090, 1125, 1255, 1375, 1455, 1705, 1955, 2865, 2920, 3345 (cm$^{-1}$)

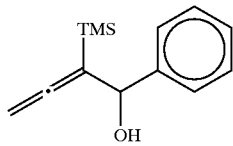

$^1$H-NMR, δ: 0.20 (s, 9H) 2.72 (d, J=4.4 Hz, 1H) 4.86 (dd, J=1.9 Hz, 2.8 Hz, 2H) 5.44 (bs, 1H) 7.4–7.6 (m, 5H)

$^{13}$C-NMR, δ: −1.18, 72.6, 72.8, 101.2, 126.8, 127.6, 128.1, 143.0, 207.0

IR: 705, 755, 845, 1050, 1200, 1255, 1410, 1460, 1500, 1605, 1935, 2960, 3370 (cm$^{-1}$)

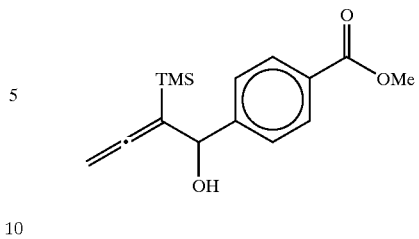

$^1$H-NMR, δ: 0.04 (s, 9H), 2.90 (bs, 1H) 3.85 (s, 3H) 4.54 (dd, J=1.2 Hz, 2.1 Hz, 2H) 5.27 (bs, 1H) 7.38 (d, J=8.6 Hz, 2H) 7.94 (d, J=8.2 Hz, 2H)

$^{13}$C-NMR, δ: −1.08, 51.9, 72.2, 72.8, 100.8, 126.5, 129.1, 129.4, 148.4, 166.9, 207.8

IR: 700, 745, 830, 1005, 1035, 1100, 1185, 1275, 1405, 1435, 1605, 1700, 1920, 2945, 3440 (cm$^{-1}$)

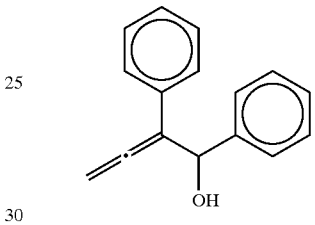

$^1$H-NMR, δ: 5.17 (m, 2H) 5.65 (bs, 1H) 2.28 (bs, 1H) 7.1–7.5 (m, 10H)

$^{13}$C-NMR, δ: 72.3, 81.0, 109.8, 126.8, 126.9, 127.7, 128.3, 133.9, 141.9, 207.7

IR: 690, 760, 795, 850, 910, 950, 1020, 1180, 1255, 1380, 1450, 1490, 1595, 1705, 1880, 1935, 2910, 3030, 3390 (cm$^{-1}$)

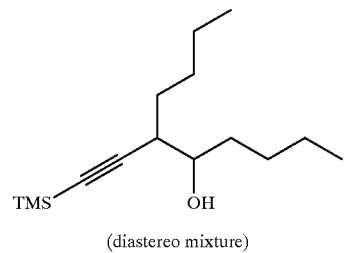

(diastereo mixture)

$^1$H-NMR, δ: 0.135 (s, 9H) (minor) 0.142 (s, 9H) (major) 0.88 (t, J=6.5 Hz, 6H) 1.77 (bs, 1H) (minor) 1.80 (bs, 1H) (major) 2.41 (dt, J=4.5 Hz, 9.0 Hz, 1H) (major) 2.49 (dt, J=4.7 Hz, 9.3 Bz, 1H) (minor) 3.43 (m, 1H) (major) 3.53 (m, 1H) (minor)

$^{13}$C-NMR, δ: 0.13, 14.0, 22.5, 25.5, 27.1, 29.9, 31.5, 31.7, 33.7, 35.5, 40.2, 72.9 (major), 73.4 (minor), 87.7 (minor), 88.6 (major), 106.6 (major), 107.7 (minor)

IR: 690, 755, 840, 925, 1020, 1055, 1120, 1250, 1380, 1405, 1460, 2170, 2860, 2930, 3370 (cm$^{-1}$)

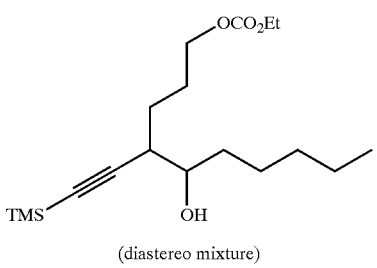

(diastereo mixture)

¹H-NMR, δ: 0.13 (s, 9H) (minor) 0.14 (s, 9H) (major) 0.88 (t, J=6.7 Hz, 3H) 1.29 (t, J=7.1 Hz, 3H) 1.37–1.98 (m, 12H) 2.41–2.54 (m, 1H) 3.39–3.48 (1H) (major) 3.51–3.58 (1H) (minor) 4.15 (t, J=6.3 Hz, 2H) 4.17 (q, J=7.1 Hz, 2H)

¹³C-NMR, δ: 0.06, 13.9, 14.2, 22.5, 25.3 (minor), 25.4 (major), 26.2 (minor), 26.7 (minor), 26.8 (major), 27.8, 31.7, 33.9 (minor), 35.4, 39.8, 63.8, 67.5 (major), 67.6 (minor), 72.9 (major), 73.3 (minor), 88.4 (minor), 89.3 (major), 105.5 (major), 106.8 (minor), 155.2

IR: 700, 770, 810, 855, 1025, 1095, 1270, 1385, 1465, 1605, 1755, 2170, 2950, 3450 (cm⁻¹)

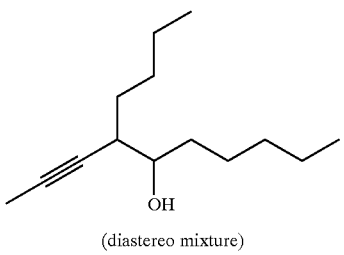

(diastereo mixture)

¹H-NMR, δ: 0.86 (t, J=6.5 Hz, 6H) 1.1–1.7 (m, 16H) 2.00 (bs, 1H) 2.07 (d, J=2.4 Hz) (minor) 2.10 (d, J=2.4 Hz) (major) 2.33–2.40 (m, 1H) (major) 2.45–2.49 (m, 1H) (minor) 3.37–3.57 (m, 1H)

¹³C-NMR, δ: 13.9, 22.5, 25.4, 27.1, 30.0, 31.5, 31.7, 33.6, 35.4, 38.8 (major), 39.1 (minor), 71.1 (minor), 71.7 (major), 72.9 (major), 73.3 (minor), 84.1 (major), 85.0 (minor)

IR: 715, 845, 915, 1030, 1120, 1255, 1380, 1460, 1710, 2115, 2860, 2915, 3300, 3350 (cm⁻¹)

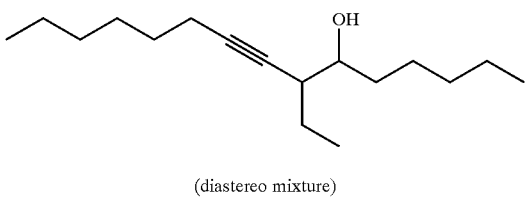

(diastereo mixture)

¹H-NMR, δ: 0.86 (t, J=6.7 Hz, 6H) 0.98 (t, J=7.4 Hz, 3H) 1.2–1.6 (m, 18H) 1.82 (bs, 1H) 2.16 (dt, J=2.2 Hz, 6.9 Hz, 2H) 2.23–2.31 (m, 1H) (major) 2.32–2.42 (m, 1H) (minor) 3.35–3.45 (m, 1H) (major) 3.46–3.55 (m, 1H) (minor)

¹³C-NMR, δ: 12.0, 12.1, 13.9, 18.7, 22.5, 22.6, 23.6, 25.3, 25.5, 28.5, 29.0, 31.3, 31.8, 33.8, 35.6, 41.1, 73.0 (major), 73.5 (minor), 79.0 (major), 80.2 (minor), 83.7 (minor), 84.6 (major)

IR: 720, 810, 905, 1015, 1085, 1155, 1250, 1375, 1455, 1735, 2120, 2860, 2920, 3365 (cm⁻¹)

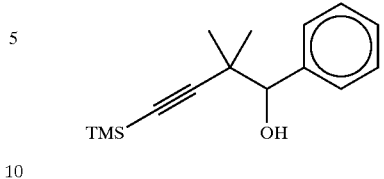

¹H-NMR, δ: 0.39 (s, 9H) 1.29 (s, 3H) 1.46 (s, 3H) 2.78 (d, J=4.4 Hz) 4.68 (d, J=4.1 Hz) 7.5–7.6 (m, 5H)

¹³C-NMR, δ: 0.09, 24.6, 26.1, 80.1, 87.0, 111.6, 127.5, 127.7, 139.9

IR (nujor): 660, 710, 745, 765, 850, 915, 980, 1015, 1035, 1050, 1095, 1145, 1205, 1255, 1350, 1390, 1465, 1765, 2175, 2920, 3440 (cm⁻¹)

EXAMPLE 3-22

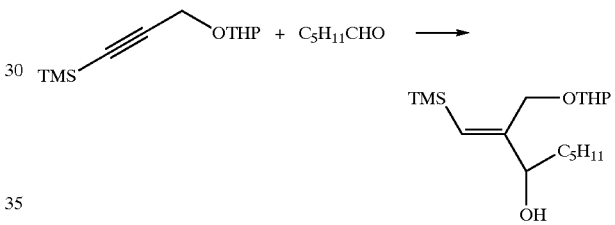

To 0.175 ml (0.60 mmol) of tetraisopropoxytitanium and 3.5 ml of ethyl ether solution of 3-trimethylsilylpropargyl alcohol tetrahydropyranyl ether (97 mg, 0.46 mmol) was added dropwise at −78° C. under an argon atmosphere 0.5 ml of 2.27M ethyl ether solution containing isopropylmagnesium bromide (1.13 mmol). After heating to −50° C. over 1 hour, the reaction liquid was stirred for 2 hours. The reaction liquid was cooled to −78° C. again and was given 0.072 ml (0.60 mmol) of hexanal. The reaction liquid was heated to −40° C. over 2 hours. With 1N hydrochloric acid added, the solution was separated into layers. The organic layer was washed with a saturated aqueous solution of sodium hydrogen carbonate. After drying with anhydrous magnesium sulfate, the solution was freed of solvent by vacuum distillation. The residues were purified by silica gel chromatography. Thus there was obtained 113 mg of the desired reaction product (yields: 78%).

EXAMPLES 3-23 TO 3-26

The procedure of Example 3-22 was repeated except that the 3-trimethylsilylpropargyl alcohol tetrahydropyranyl ether and hexanal were replaced by those compounds shown in Table 6. There were obtained corresponding addition products in yields as shown in Table 6.

TABLE 6

| Example | Propargyl compound | Aldehyde | Reaction product | Yields (%) |
|---|---|---|---|---|
| 3-22 | TMS-≡-CH₂-OTHP | C₅H₁₁CHO | TMS / OTHP, C₅H₁₁, OH | 78 |
| 3-23 | TMS-≡-CH₂-OTHP | PhCHO | gt,0080 | 78 |
| 3-24 | TMS-≡-CH₂-OSi+ | EtCHO | TMS / OSi+, OH | 71 |
| 3-25 | C₄H₉-≡-CH₂-OTHP | C₅H₁₁CHO | C₄H₉ / OTHP, C₅H₁₁, OH | 46 |
| 3-26 | Ph-≡-CH₂-OTHP | EtCHO | Ph / OTHP, OH | 63 |

THP: tetrahydropyranyl group

Reaction Product in Example 3-22
$^1$H-NMR, δ: 0.13 (s, 9H) 0.89 (br t, J=7.7 Hz, 3H) 1.19 (m, 6H) 1.46–1.65 (m, 6H) 1.65–1.78 (m, 2H) 3.55 (m, 1H) 3.87 (m, 1H) 4.05 (d, J=11.6 Hz, 1H) [4.11 (d, J=11.5 Hz, 1H)] 4.43 (d, J=11.5 Hz, 1H) [4.37 (d, J=11.6 Hz, 1H)] 4.13 (t, J=2.8 Hz, 1H) 4.64 (t, J=3.5 Hz, 1H) 5.70 (s, 1H) [5.71 (s, 1H)]

Reaction Product in Example 3-23
$^1$H-NMR, δ: 0.21 (s, 9H) 1.43–1.72 (m, 6H) 3.47 (m, 1H) 3.65 (m, 1H) 3.95 (d, J=11.6 Hz, 1H) [4.00 (d, J=11.7 Hz, 1H)] 4.35 (d, J=11.6 Hz, 1H) [4.24 (d, J=11.7 Hz, 1H)] 4.57 (t, J=3.2 Hz, 1H) [4.51 (d, J=3.4 Hz, 1H)] 5.36 (t, J=5.1 Hz, 1H) 5.94 (s, 1H) [6.02 (s, 1H)]
$^{13}$C-NMR (75 MH₂, CDCl₃): 0.09, 19.07 (19.14), 25.24, 30.39 (30.44), 61.79 (61.86), 67.22 (67.18), 78.65 (78.78), 98.49 (98.05), 126.45, 127.23, 128.18, 130.03 (129.98), 142.36 (142.41), 154.26 (154.04)

Reaction Product in Example 3-24
$^1$H-NMR, δ: 0.10 (s, 6H) 0.12 (s, 9H) 0.90 (t, J=7.4 Hz, 3H) 0.91 (s, 9H) 1.64 (m, 2H) 4.05 (t, J=7.7 Hz, 1H) 4.30 (d, J=12.0 Hz, 1H) 4.37 (d, J=11.7 Hz, 1H) 5.56 (s, 1H)

Reaction Product in Example 3-25
$^1$H-NMR, δ: 0.88 (m, 6H) 1.29 (m, 10H) 1.56 (m, 6H) 1.70 (m, 2H) 2.23 (m, 2H) 2.80 (bs, 1H) 3.56 (m, 1H) 3.88 (m, 1H) 4.05 (t, J=6.9 Hz, 1H) 4.16 (d, J=11.6 Hz, 1H) 4.33 (d, J=11.5 Hz, 1H) [4.41 (d, J=11.4 Hz, 1H)] 4.66 (t, J=3.1 Hz, 1H) 5.60 (t, J=7.4 Hz, 1H)

Reaction Product in Example 3-26
$^1$H-NMR, δ: 0.98 (t, J=7.5 Hz, 3H) [0.99 (t, J=8.0 Hz, 3H)] 1.56 (m, 3H) 1.68 (m, 3H) 1.77 (m, 2H) 3.04 (bs, 1H) 3.54 (m, 1H) 3.87 (m, 1H) 4.18 (bt, J=11.6 Hz, 1H) 4.23 (d, J=11.5 Hz, 1H) 4.50 (d, J=11.4 Hz, 1H) [4.53 (d, J=11.3 Hz, 1H)] 4.66 (t, J=3.8 Hz, 1H) 6.70 (s, 1H) [6.72 (s, 1H)]

EXAMPLE 4-1

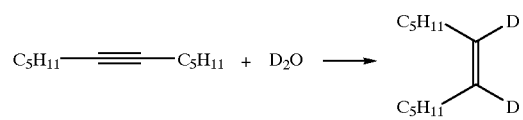

To 0.275 ml (0.938 mmol) of tetraisopropoxytitanium and 10 ml of ethyl ether solution containing 6-dodecyn (125 mg, 0.75 mmol) was added dropwise at −78° C. under an argon N atmosphere 1.53 ml of 1.53M ethyl ether solution containing isopropylmagnesium chloride (2.34 mmol). After heating to −50° C. over 30 minutes, the reaction liquid was stirred for 2 hours. The reaction liquid was cooled to −78° C. again and was given 1 ml of heavy water. The reaction liquid was heated to room temperature. With 1N hydrochloric acid added, the solution was separated into layers. The organic layer was dried with anhydrous magnesium sulfate and was freed of solvent by vacuum distillation. The residues were purified by silica gel chromatography. Thus there was obtained 104 mg of (Z)-6,7-dideuterio-6-dodecene (yields: 81%).

EXAMPLES 4-2 TO 4-6

The procedure of Example 4-1 was repeated except that the 6-dodecyn was replaced by those compounds shown in Table 7. There were obtained corresponding deuterio compounds in yields as shown in Table 7.

TABLE 7

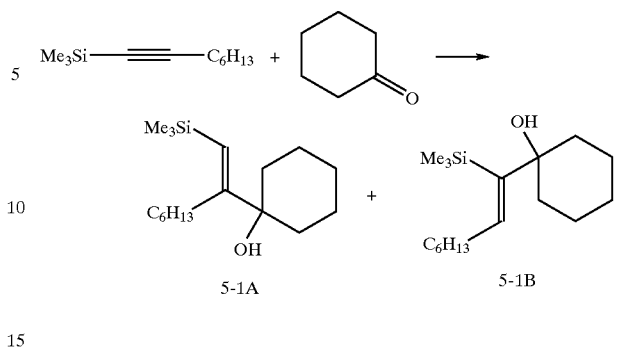

| Example | Ra | Rb | Yields (%) | Z:E |
|---|---|---|---|---|
| 4-1 | C$_5$H$_{11}$ | C$_5$H$_{11}$ | 81 | >99:1 |
| 4-2 | C$_6$H$_{13}$ | Me | 100 | >99:1 |
| 4-3 | C$_6$H$_{13}$ | CH$_2$OEE | 100 | >99:1 |
| 4-4 | Ph | Me | 74 | >99:1 |
| 4-5 | Ph | Ph | 96 | 99.4:0.6 |
| 4-6 | Me$_3$Si | C$_6$H$_{13}$ | 94 (89) | >99:1 |
| 4-7 | Me$_3$Si | Me$_3$Si | 100 | >99:1 |

EXAMPLE 4-1

(Z)-6,7-Dideuterio-6-dodecene $^1$H-NMR, δ: 0.89 (t, J=6.9 Hz, 6H) 1.21–1.42 (m, 12H) 2.01 (t, J=6.8 Hz, 4H)

$^{13}$C-NMR, δ: 14.04, 22.58, 27.05, 29.46, 31.55, 129.10, 129.40, 129.71

IR: 2925, 2855, 1730, 1460 (cm$^{-1}$)

EXAMPLE 4-2

(Z)-2,3-Dideuterio-2-nonene $^1$H-NMR, δ: 0.88 (t, J=6.0 Hz, 3H) 1.12–1.44 (m, 8H) 1.59 (s, 2H) 1.95–2.10 (m, 3H)

EXAMPLE 4-3 l-Ethoxyethylether of (Z)-2,3-dideuterio-2-nonene-1-ol $^1$H-NMR, δ: 0.88 (t, J=6.7 Hz, 3H) 1.22 (t, J=7.1 Hz, 3H) 1.33 (d, J=5.4 Hz, 3H) 1.18–1.42 (m, 8H) 2.06 (t, J=6.9 Hz, 2H) 3.50 and 3.64 (dq, J=9.4, 7.1 Hz, 2H) 4.10 (m, 2H) 4.74 (q, J=5.4 Hz, 1H)

$^{13}$C-NMR, δ: 13.93, 15.22, 19.74, 22.51, 27.32, 28.82, 29.43, 31.62, 60.24, 60.59, 98.85, 125.16, 125.49, 125.81, 132.49, 132.80, 133.10

IR: 2920, 2850, 2245, 1730, 1450, 1380, 1130, 1090, 1055, 930 (cm$^{-1}$)

EXAMPLE 4-4

(Z)-1,2-Dideuterio-1-phenyl-1-propene $^1$H-NMR, δ: 1.89 (s, 3H) 7.17–7.38 (m, 5H)

EXAMPLE 4-5

(Z)-1,2-Dideuterio-1,2-diphenylethylene $^1$H-NMR, δ: 7.14–7.29 (m, 10H)

$^{13}$C-NMR, δ: 127.05, 128.16, 128.83, 129.40, 129.85, 137.13

IR: 3150, 1600, 1490, 1445, 750, 695 (cm$^{-1}$)

EXAMPLE 4-6

(Z)-1,2-Dideuterio-1-(trimethylsilyl)-1-octene $^1$H-NMR, δ: 0.11 (s, 9H) 1.18–1.44 (m, 8H) 2.11 (t, J=7.0 Hz, 2H)

$^{13}$C-NMR, δ: 0.23, 14.06, 22.64, 29.06, 29.76, 31.82, 33.42, 127.87, 128.14, 128.41, 148.56, 148.87, 149.17

IR: 2925, 2855, 1585, 1460, 1250, 840, 755 (cm$^{-1}$)

EXAMPLE 5-1

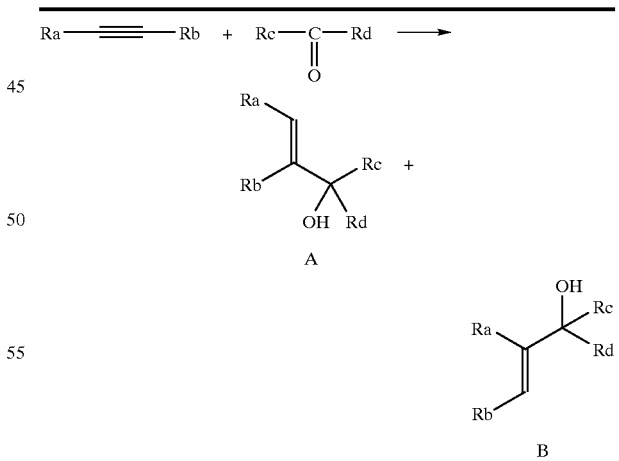

To 0.22 ml (0.75 mmol) of tetraisopropoxytitanium and 8 ml of ethyl ether solution containing 1-trimethylsilyl-1-octyne (137 mg, 0.75 mmol) was added dropwise at −78° C. under an argon atmosphere 1.20 ml of 1.25M ethyl ether solution containing isopropylmagnesium chloride (1.50 mmol). After heating to −50° C. over 30 minutes, the reaction liquid was stirred for 2 hours. The reaction liquid was cooled to −78° C. again and was given 0.054 ml (0.53 mmol) of cyclohexanone. The reaction liquid was stirred further at −75° C. to −70° C. for 1 hour. The reaction liquid was given 0.8 ml of water and heated to room temperature. The reaction liquid was filtered through celite. The filtrate was dried with anhydrous magnesium sulfate and freed of solvent by vacuum distillation. The residues were purified by silica gel chromatography. Thus there was obtained 124 mg of a mixture of 5-1A and 5-1B (yields: 84%, A:B=96:4).

EXAMPLES 5-2 TO 5-10

The procedure of Example 5-1 was repeated except that the 1-trimethylsilyl-1-octyne and cyclohexanone were replaced by those compounds shown in Table 8. There were obtained corresponding alcohols in yields as shown in Table 8.

TABLE 8

| Example | Ra | Rb | RcCORd | Yields (%) | A:B |
|---|---|---|---|---|---|
| 5-1 | Me$_3$Si | C$_6$H$_{13}$ | Cyclohexanone | 84 | 96:4 |
| 5-2 | C$_5$H$_{11}$ | C$_5$H$_{11}$ | Cyclohexane-carbaldehyde | 70 | — |
| 5-3 | Ph | Me | Cyclohexane-carbaldehyde | 81 | 16:84 |

TABLE 8-continued

Ra≡≡≡Rb + Rc—C(=O)—Rd ⟶

Ra\C=C/Rb with Rc, OH, Rd (A)

+

Ra\C=C/Rb with OH, Rc, Rd (B)

| Example | Ra | Rb | RcCORd | Yields (%) | A:B |
|---|---|---|---|---|---|
| 5-4 | $Me_3Si$ | $C_6H_{13}$ | Hexanal | 79 | 79:21 |
| 5-5 | $Me_3Si$ | $C_6H_{13}$ | 2-Methylbutanal | 84 | 86:14 |
| 5-6 | $Me_3Si$ | $C_6H_{13}$ | Cyclohexane-carbaldehyde | 86 | 85:15 |
| 5-7 | $Me_3Si$ | $C_6H_{13}$ | Crotonealdehyde | 72 | 96:4 |
| 5-8 | $Me_3Si$ | $C_6H_{13}$ | Benzaldehyde | 47 | 93:7 |
| 5-9 | $Me_3Si$ | $C_6H_{13}$ | Methyl-4-oxopentanoate | 83 | 96:4 |
| 5-10 | $Me_3Si$ | $Me_3Si$ | Cyclohexane-carbaldehyde | 70 | — |

EXAMPLE 5-1

Reaction Product of 5-1A+5-1B (96:4)

$^1$H-NMR, δ: 0.11 (s, 9H(A)) 0.22 (s, 9H(B)) 0.89 (t, J=6.6 Hz, 3H) 1.12–1.72 (m, 19H) 2.10–2.19 (m, 2H) 5.55 (s, 1H(A)) 6.14 (t, J=7.6 Hz, 1H(B))

$^{13}$C-NMR, δ: A: 0.94, 14.65, 22.70, 23.26, 26.12, 30.81, 32.36, 33.25, 33.38, 37.46, 76.15, 121.56, 166.48

IR: 3415, 2920, 2855, 1600, 1450, 1250, 840 (cm$^{-1}$)

EXAMPLE 5-2

Reaction Product of 5-2A $^1$H-NMR, δ: 0.84–0.95 (m, 6H) 1.08–1.82 (m, 24H) 1.92–2.08 (m, 4H) 3.67 (d, J=7.7 Hz, 1H) 5.31 (t, J=7.4 Hz, 1H)

$^{13}$C-NMR, δ: 14.04, 22.49, 22.54, 26.06, 26.19, 26.51, 27.48, 27.78, 28.77, 29.50, 29.79, 30.03, 31.61, 32.48, 41.37, 82.09, 128.05, 140.82

IR: 3370, 2915, 2855, 1450, 995 (cm$^{-1}$)

EXAMPLE 5-3

Reaction Product of 5-3A+5-3B (16:84)

$^1$H-NMR, δ: 0.89–1.93 (m, 12H) 1.55 (d, J=6.0 Hz, 3H(A)) 1.85 (s, 3H(B)) 3.83 (d, J=7.8 Hz, 1H(B)) 4.00 (d, J=7.1 Hz, 1H(A)) 5.74 (q, J=6.8 Hz, 1H(A)) 6.42 (s, 1H(B))

$^{13}$C-NMR, δ: A: 14.23, 25.91, 26.04, 26.46, 27.85, 30.12, 40.88, 81.65, 123.88, 126.73, 128.05, 129.27, 138.40, 143.00 B: 126.36, 127.01, 128.95

IR: 3355, 2915, 2850, 1600, 1445, 1075, 1000, 700 (cm$^{-1}$)

EXAMPLE 5-4

Reaction Product of 5-4A+5-4B (79:21)

$^1$H-NMR, δ: 0.11 (s, 9H(A)) 0.17 (s, 9H(B)) 0.82–0.97 (m, 6H) 1.17–1.69 (m, 13H) 1.96–2.08 (m, 1H(A)) 2.08–2.26 (m, 1H(A) and 2H(B)) 4.00–4.19 (m, 1H(A)) 4.14 (dt, J=1.0, 5.0 Hz, 1H(B)) 5.48 (s, 1H(A)) 6.19 (dt, J=1.0, 5.0 Hz, 1H(B))

$^{13}$C-NMR, δ: A: 0.26, 14.01, 22.59, 25.44, 29.82, 29.87, 30.52, 31.72, 31.80, 33.54, 36.30, 37.83, 75.83, 121.79, 161.88 B: 0.77, 86.09, 142.07

IR: 3345, 2920, 2855, 1610, 1460, 125.0, 835 (cm$^{-1}$)

EXAMPLE 5-10

Reaction Product of 5-10A $^1$H-NMR, δ: 0.16 and 0.18 (s, 18H) 0.82–1.80 (m, 11H) 4.03 (d, J=4.9 Hz, 1H) 6.46 (s, 1H)

$^{13}$C-NMR, δ: 1.11, 26.16, 26.30, 26.54, 26.65, 30.94, 42.05, 82.93, 141.51, 162.53

IR: 3425, 2920, 2860, 1455, 1250, 1090, 1010, 835, 750 (cm$^{-1}$)

EXAMPLE 6-1

$Me_3Si$—≡—$C_8H_{13}$+$C_3H_7CH$=N—$CH_2Ph$ $Me_3Si$—≡—$C_6H_{13}$ + $C_3H_7CH$=N—$CH_2Ph$ ⟶

$Me_3Si$, $C_6H_{13}$ / C=C / $C_3H_7$, $NHCH_2Ph$

To 9 ml of ethyl ether solution of 0.33 g (1.16 mmol) of tetraisopropoxytitanium and 212 mg (1.16 mmol) of 1-trimethylsilyl-1-octyne was added dropwise at −78° C. 1.16 ml of 2M ethyl ether solution containing isopropylmagnesium chloride (2.32 mmol). After heating to −50° C. over 30 minutes, the reaction liquid was stirred for 2 hours. The reaction liquid was given 149 mg (0.93 mmol) of N-butylidenebenzylamine, stirred at −50° C. for 1 hour, and heated to −10° C. over 2 hours. The reaction liquid was given 2 ml of water and heated to room temperature. The reaction liquid was given 3 ml of 3N hydrochloric acid and stirred to dissolve precipitates completely. The solution was made alkaline with a saturated aqueous solution of sodium hydrogen carbonate. After extraction with 60 ml of hexane-ether mixture (1:1), the organic layer was dried with anhydrous magnesium sulfate and freed of solvent by vacuum distillation. The residues were purified by silica gel chromatography. Thus there was obtained 267 mg of 1-trimethyl-2-hexyl-3-(N-benzyl)amino-(E)-1-hexene (yields: 83%).

EXAMPLE 6-2

The procedure of Example 6-1 was repeated except that water was replaced by heavy water ($D_2O$). There was obtained a deuterio compound in a yield of 83% and a conversion of 94%.

EXAMPLE 6-3

The procedure of Example 6-1 was repeated except that water was replaced by iodine. There was obtained an iodinated compound in a yield of 76%.

EXAMPLES 6-4 TO 6-16

The procedure of Example 6-1 was repeated except that the 1-trimethylsilyl-1-octyne and N-butylidenebenzylamine were replaced by those compounds shown in Table 9. There were obtained corresponding amines in yields as shown in Table 9. Incidentally, the lithio salt of imine in Examples 6-14 to 6-16 was prepared by dropping a nitrile compound into a hexane-ether solution of methyl lithium at 0° C.

TABLE 9

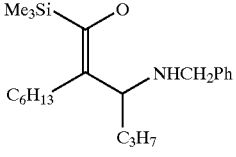

| Example | Ra | Rb | Rc | Rd | Re | Post-treatment | Reaction product | Yields (%) |
|---|---|---|---|---|---|---|---|---|
| 6-1 | Me$_3$Si | C$_6$H$_{13}$ | C$_3$H$_7$ | H | CH$_2$Ph | H$_2$O | 6B | 83 |
| 6-2 | Me$_3$Si | C$_6$H$_{13}$ | C$_3$H$_7$ | H | CH$_2$Ph | D$_2$O | 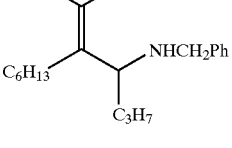 | 83 |
| 6-3 | Me$_3$Si | C$_6$H$_{13}$ | C$_3$H$_7$ | H | CH$_2$Ph | I$_2$ | (Me$_3$Si, I, C$_6$H$_{13}$, NHCH$_2$Ph, C$_3$H$_7$) | 76 |
| 6-4 | C$_3$H$_7$ | C$_3$H$_7$ | C$_3$H$_7$ | H | CH$_2$Ph | H$_2$O | 6B | 75 |
| 6-5 | Ph | CH$_3$ | C$_3$H$_7$ | H | CH$_2$Ph | H$_2$O | 6A + 6B (40:60) | 71 |
| 6-6 | Me$_3$Si | Ph | C$_3$H$_7$ | H | CH$_2$Ph | H$_2$O | 6B | 72 |
| 6-7 | Ph | Ph | C$_3$H$_7$ | H | CH$_2$Ph | H$_2$O | 6B | 82 |
| 6-8 | Me$_3$Si | C$_6$H$_{13}$ | C$_3$H$_7$ | H | C$_3$H$_7$ | H$_2$O | 6B | 90 |
| 6-9 | Me$_3$Si | C$_6$H$_{13}$ | Ph | H | Ph | H$_2$O | 6B | 89 |
| 6-10 | Me$_3$Si | C$_6$H$_{13}$ | 2-퓨릴 | H | CH$_2$Ph | H$_2$O | 6B | 82 |
| 6-11 | Me$_3$Si | C$_6$H$_{13}$ | 싸이에닐 | H | CH$_2$Ph | H$_2$O | 6B | 94 |
| 6-12 | Me$_3$Si | C$_6$H$_{13}$ | Ph | H | NMe$_2$ | H$_2$O | 6B | 92 |
| 6-13 | Me$_3$Si | C$_6$H$_{13}$ | C$_4$H$_9$ | CH$_3$ | C$_3$H$_7$ | H$_2$O | 6B | 54 |
| 6-14 | Me$_3$Si | C$_6$H$_{13}$ | C$_2$H$_5$ | CH$_3$ | Li | H$_2$O | 6B | 75 |
| 6-15 | Me$_3$Si | C$_6$H$_{13}$ | Ph | CH$_3$ | Li | H$_2$O | 6B | 68 |
| 6-16 | Me$_3$Si | C$_6$H$_{13}$ | C$_8$H$_{17}$ | CH$_3$ | Li | H$_2$O | 6B | 60 |

Reaction Product in Example 6-1

$^1$H-NMR, δ: 7.18–7.40 (m, 5H) 5.43 (s, 1H) 3.72 (d, J=13.0 Hz, 1H) 3.47 (d, J=13.0 Hz, 1H) 3.01 (t, J=5.9 Hz, 1H) 2.08–2.21 (m, 1H) 1.93–2.08 (m, 1H) 1.20–1.50 (br m, 13H) 0.89 (t, J=6.6 Hz, 3H) 0.88 (t, J=7.1 Hz, 3H) 0.13 (s, 9H)

$^{13}$C-NMR, δ: 160.62, 141.18, 128.24, 128.14, 126.66, 122.93, 64.84, 51.42, 38.10, 34.10, 31.78, 30.64, 30.03, 22.63, 19.65, 14.19, 14.05, 0.44

IR: 2880, 1590, 1440, 1230, 1100, 920, 680 (cm$^{-1}$)

Reaction Product in Example 6-4

$^1$H-NMR, δ: 7.18–7.37 (m, 5H) 5.28 (t, J=7.1 Hz, 1H) 3.72 (d, J=13.1 Hz, 1H) 3.52 (d, J=13.1 Hz, 1H) 2.97 (t, J=6.7 Hz, 1H) 1.86–2.12 (m, 4H) 1.20–1.52 (m, 9H) 0.94 (t, J=7.3 Hz, 3H) 0.93 (t, J=7.3 Hz, 3H) 0.87 (t, J=7.2 Hz, 3H)

$^{13}$C-NMR, δ: 141.30, 139.95, 128.23, 128.10, 127.96, 126.59, 65.04, 51.38, 37.35, 29.85, 29.74, 23.23, 23.16, 19.73, 14.85, 14.11, 13.90

IR: 3300 (br), 2920, 2860, 1600, 1455, 1120, 895, 730, 695 (cm$^{-1}$)

Reaction Product in Example 6-5

$^1$H-NMR, δ:

major isomer (A): 7.13–7.38 (m, 10H) 6.38 (s, 1H) 3.76 (d, J=13.2 Hz, 1H) 3.61 (d, J=13.2 Hz, 1H) 3.18 (t, J=7.0 Hz, 1H) 1.83 (s, 3H), 1.39–1.65 (m, 3H) 1.21–1.39 (m, 2H) 0.90 (t, J=7.3 Hz, 3H)

minor isomer (B): 7.10–7.41 (m, 10H) 5.65 (q, J=5.7 Hz, 1H) 3.95 (d, J=13.4 Hz, 1H) 3.72 (d, J=13.4 Hz, 1H) 3.24 (t, J=5.9 Hz, 1H) 1.55 (d, J=6.8 Hz, 3H) 1.20–1.45 (m, 5H) 0.84 (t, J=6.8 Hz, 3H)

$^{13}$C-NMR, δ:

major isomer (A): 140.91, 139.35, 138.05, 128.93, 128.28, 128.17, 128.04, 127.54, 126.73, 126.12, 66.27, 51.35, 36.48, 19.67, 14.13, 12.44 minor isomer (B): 142.31, 141.01, 138.96, 129.20, 128.28, 128.11, 127.93, 126.69, 126.51, 124.07, 64.90, 51.23, 36.90, 19.59, 14.34, 14.04

IR:

major isomer (A): 3300 (br), 2900, 1590, 1440, 1105, 830, 715, 685 minor isomer (B): 3300 (br), 3010, 2920, 2850, 1590, 1490, 1450, 1360, 1110, 1070, 900, 830, 730, 690 (cm$^{-1}$)

Reaction Product in Example 6-6

$^1$H-NMR, δ: 7.47–7.68 (m, 8H) 7.33–7.42 (m, 2H) 5.99 (s, 1H) 4.22 (d, J=13.2 Hz, 1H) 3.98 (d, J=13.2 Hz, 1H) 3.54 (t, J=85.3 Hz, 5H) 1.48–1.77 (m, 5H) 1.12 (t, J=6.2 Hz, 3H) 0.10 (s, 9H)

$^{13}$C NMR, δ: 159.01, 141.86, 140.94, 128.84, 128.75, 128.30, 128.17, 127.58, 126.91, 126.75, 67.11, 51.37, 36.78, 19.45, 14.06, 0.03

IR: 33850 (br), 3025, 2920, 1590, 1450, 1245, 1120, 850, 830, 740, 690 (cm$^{-1}$)

Reaction Product in Example 6-7

$^1$H-NMR, δ: 6.87–7.41 (m, 15H) 6.54 (s, 1H) 4.03 (d, J=13.4 Hz, 1H) 3.80 (d, J=13.4 Hz, 1H) 3.40 (t, J=5.2 Hz, 1H) 1.22–1.58 (m, 5H) 0.87 (t, J=5.5 Hz, 3H)

$^{13}$C-NMR, δ: 143.36, 140.89, 139.20, 136.92, 129.14 (2 peaks), 128.56, 128.50, 128.33, 128.13, 127.85, 127.04, 126.78, 126.42, 65.85, 51.35, 36.84, 19.60, 14.06

IR: 3400 (br), 3020, 2925, 1595, 1490, 1445, 1120, 1070, 1020, 905, 730, 690 (cm$^{-1}$)

Reaction Product in Example 6-8

$^1$H-NMR, δ: 5.32 (s, 1H) 2.94 (t, J=6.2 Hz, 1H) 2.38–2.50 (m, 1H) 2.26–2.38 (m, 1H) 2.03–2.16 (m, 1H) 1.88–2.01 (m, 1H) 1.11–1.52 (m, 15H) 0.88 (t, J=7.3 Hz, 6H) 0.87 (t, J=7.0 Hz, 3H) 0.09 (s, 9H)

$^{13}$C-NMR, δ: 160.92, 122.59, 65.39, 49.40, 38.07, 34.19, 31.80, 30.58, 30.03, 23.38, 22.64, 19.62, 14.22, 14.04, 11.86, 0.39

IR: 3350 (br), 2925, 2850, 1610, 1460, 1245, 1140, 840, 680

Reaction Product in Example 6-9

$^1$H-NMR, δ: 7.21–7.37 (m, 5H) 7.13 (dd, like t, J=J=7.9 Hz, 2H) 6.68 (dd, like t, J=J=7.3 Hz, 1H) 6.54 (d, J=8.4 Hz, 2H) 5.68 (s, 1H) 4.81 (s, 1H) 3.95 (br s, 1H) 2.18–2.32 (m, 1H) 1.90–2.03 (m, 1H) 1.37–1.61 (m, 2H) 1.20–1.37 (br s, 6H) 0.88 (t, J=6.6 Hz, 3H) 0.10 (s, 9H)

$^{13}$C-NMR, δ: 157.43, 147.63, 142.01, 128.95, 128.58, 127.71, 127.36, 124.30, 117.25, 113.33, 64.49, 34.74, 34.68, 31.67, 29.96, 22.60, 14.02, 0.29

IR: 3380, 2900, 2840, 1595, 1500, 1305, 1240, 830, 740, 680 (cm$^{-1}$)

Reaction Product in Example 6-10

$^1$H-NMR, δ: 7.37 (m, 1H) 7.18–7.35 (m, 5H) 6.30 (dd, J=3.1, J=1.8 Hz, 1H) 6.12 (d, J=3.1 Hz, 1H) 5.81 (s, 1H) 4.13 (s, 1H) 2.65 (s, 2H) 2.00–2.14 (m, 1H) 1.69–1.87 (m, 1H) 1.75 (br s, 1H) 1.12–1.38 (br s, 8H) 0.86 (t, J=6.8 Hz, 3H) 0.13 (s, 9H)

$^{13}$C-NMR, δ: 158.95, 154.17, 142.39, 141.64, 128.27, 127.99, 127.15, 122.34, 110.02, 106.90, 67.06, 44.01, 34.42, 31.66, 29.99, 29.65, 22.55, 14.02, 0.39

IR: 2925, 1600, 1455, 1250, 1150, 1010, 840, 735, 700 (cm$^{-1}$)

Reaction Product in Example 6-11

$^1$H-NMR, δ: 7.17–7.39 (m, 5H) 5.33 (s, 1H) 3.73 (d, J=13.2 Hz, 1H) 3.45 (d, J=13.2 Hz, 1H) 2.75 (d, J=6.8 Hz, 1H) 2.07–2.21 (m, 1H) 1.80–2.01 (m, 2H) 0.97–1.80 (m, 19H) 0.89 (t, J=6.3 Hz, 3H) 0.12 (s, 9H)

$^{13}$C-NMR, δ: 159.07, 141.39, 128.18, 128.14, 126.60, 124.04, 70.59, 51.61, 41.69, 34.63, 31.81, 31.07, 30.69, 30.11, 29.25, 26.71, 26.63, 26.57, 22.65, 14.06, 0.49

IR: 3350 (br), 2910, 2850, 1605, 1450, 1250, 1010, 840, 730, 690 (cm$^{-1}$)

Reaction Product in Example 6-12

$^1$H-NMR, δ: 7.18–7.36 (m, 5H) 5.76 (s, 1H) 4.38 (s, 1H) 2.97 (s, 1H) 2.44 (s, 6H) 1.97–2.17 (m, 1H) 1.82–1.97 (m, 1H) 1.21 (br s, 8H) 0.86 (t, J=6.7 Hz, 3H) 0.11 (s, 9H)

$^{13}$C-NMR, δ: 158.96, 141.25, 128.17, 127.86, 126.99, 125.57, 123.39, 67.86, 48.05, 34.73, 31.65, 30.09, 29.13, 22.56, 14.01, 0.38

IR: 3350 (br), 2925, 2850, 1600, 1460, 1250, 1020, 840, 745, 695 (cm$^{-1}$)

Reaction Product in Example 6-13

$^1$H-NMR, δ: 5.32 (s, 1H) 2.27–2.39 (m, 1H) 2.16–2.27 (m, 1H) 1.99–2.09 (m, 2H) 1.35–1.52 (m, 7H) 0.99–1.35 (m, 10H) 1.15 (s, 3H) 0.89 (t, J=7.4 Hz, 6H) 0.87 (t, J=7.3 Hz, 3H) 0.10 (s, 9H)

$^{13}$C-NMR, δ: 162.11, 123.97, 61.38, 44.42, 40.23, 32.58, 32.27, 31.79, 30.30, 26.26, 23.93, 23.73, 23.20, 22.64, 14.06, 14.02, 11.99, 0.45

IR: 3350 (br), 2920, 1595, 1460, 1370, 1245, 840, 680 (cm$^{-1}$)

Reaction Product in Example 6-14

$^1$H-NMR, δ: 5.42 (s, 1H) 1.98–2.17 (m, 2H) 1.19–1.62 (m, 12H) 1.18 (s, 3H) 0.87 (t, J=6.7 Hz, 3H) 0.73 (t, J=7.4 Hz, 3H) 0.09 (s, 9H)

$^{13}$C-NMR, δ: 164.84, 121.74, 58.15, 34.63, 33.01, 32.67, 31.75, 30.26, 28.82, 22.65, 14.02, 8.54, 0.39

IR: 3300 (br), 2920, 1595, 1455, 1370, 1240, 835, 680 (cm$^{-1}$)

Reaction Product in Example 6-15

$^1$H-NMR, δ: 7.16–7.42 (m, 5H) 5.76 (s, 1H) 1.86–1.97 (m, 2H) 1.77 (br s, 2H) 1.58 (s, 3H) 1.06–1.25 (m, 8H) 0.82 (t, J=6.9 Hz, 3H) 0.17 (s, 9H)

$^{13}$C-NMR, δ: 164.48, 147.99, 128.01, 126.23, 125.73, 121.50, 61.41, 33.57, 32.53, 31.54, 30.05, 29.75, 2.50, 13.97, 0.32

IR: 3300 (br), 2920, 1600, 1440, 1245, 840, 760, 695 (cm$^{-1}$)

Reaction Product in Example 6-16

$^1$H-NMR, δ: 5.43 (s, 1H) 2.00–2.19 (m, 2H) 1.35–1.62 (m, 6H) 1.02–1.35,(m, 18H) 1.19 (s, 3H) 0.89 (t, J=6.5 Hz, 3H) 0.87 (t, J=6.9 Hz, 3H) 0.11 (s, 9H)

$^{13}$C-NMR, δ: 165.36, 121.39, 58.02, 42.35, 33.07, 32.69, 31.86, 31.77, 30.27, 30.06, 29.54, 29.32, 29.25, 24.23, 22.66 (2 peaks), 14.07, 14.04, 0.41

IR: 2910, 2850, 1590, 1455, 1370, 1245, 830 (cm$^{-1}$)

EXAMPLE 7-1

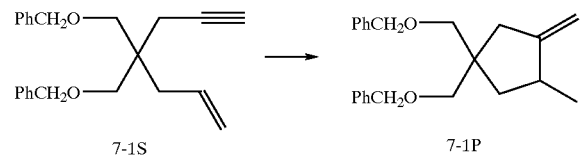

7-1S        7-1P

To 9.5 ml of ethyl ether were added under an argon atmosphere 0.37 ml (1.26 mmol) of tetraisopropoxytitanium and 330 mg (1.0 mmol) of the unsaturated compound 7-1S. After cooling to −78° C., the reaction liquid was given dropwise 2.55 ml (2.77 mmol) of isopropylmagnesium chloride. The reaction liquid was stirred at −78° C. for 30 minutes, heated to −50° C. over 30 minutes, and stirred for 2 hours. After cooling e again to −78° C., the reaction liquid was given 2 ml of 3N hydrochloric acid. The reaction liquid was heated to room temperature and extracted with hexane-ether mixture. The organic layer was washed with an saturated aqueous solution of sodium hydrogen carbonate and a saturated aqueous solution of sodium chloride. The solution was dried with anhydrous magnesium sulfate and freed of solvent by vacuum distillation. The residues were purified by silica gel chromatography. Thus there was obtained 263 mg of 7-1P in the cyclized form (yields: 79%).

EXAMPLES 7-2 TO 7-15

The procedure of Example 7-1 was repeated except that the unsaturated compound and terminator were replaced by those shown in Tables 10 and 11. There were obtained corresponding cyclized compounds in yields as shown in Tables 10 and 11.

TABLE 10

| Example | Starting material | Terminator | Reaction product | Yields (%) |
|---|---|---|---|---|
| 7-1 | PhCH₂O-/-C≡CH, PhCH₂O-/-CH=CH₂ | H₂O | PhCH₂O-/cyclopentane with =CH₂ and CH₃/-PhCH₂O | 79 |
| 7-2 | PhCH₂O-/-C≡CH, PhCH₂O-/-CH=CH₂ | CO | bicyclic ketone | 14 |
| 7-3 | PhCH₂O-/-CH=CH₂, PhCH₂O-/-CH=CH₂ | H₂O | cyclopentane dimethyl | 77 |
| 7-4 | PhCH₂O-/-CH=CH₂, PhCH₂O-/-CH=CH₂ | CO | bicyclic ketone | 51 |
| 7-5 | PhCH₂O-/-C≡C-SiMe₃, PhCH₂O-/-C≡C-SiMe₃ | H₂O | bis(SiMe₃-methylene)cyclopentane | 97 |
| 7-6 | PhCH₂O-/-C≡C-SiMe₃, PhCH₂O-/-CH=CH₂ | H₂O | cyclopentane with =CH-SiMe₃ and CH₃ | 97 |
| 7-7 | PhCH₂O-/-C≡C-SiMe₃, PhCH₂O-/-CH=CH₂ | D₂O | cyclopentane with =C(SiMe₃)D and CH₂D | 90 |
| 7-8 | PhCH₂O-/-C≡C-SiMe₃, PhCH₂O-/-CH=CH₂ | CO | bicyclic ketone with SiMe₃ | 56 |

TABLE 11

| Example | Starting material | Terminator | Reaction product | Yields (%) |
|---|---|---|---|---|
| 7-9 | CO₂Et-/-C≡CH, CO₂Et-/-C≡CH | H₂O | CO₂Et-/bis(methylene)cyclopentane/-CO₂Et | 22 |
| 7-10 | C₅H₁₁-CH(-C≡CH)(-O-CH₂-CH=CH₂) | H₂O | tetrahydrofuran with C₅H₁₁, =CH₂, CH₃ | 65 |

TABLE 11-continued

| Example | Starting material | Terminator | Reaction product | Yields (%) |
|---|---|---|---|---|
| 7-11 | PhCH₂-N(-CH₂C≡CH)(-CH₂CH=CH₂) | H₂O | 1-benzyl-3-methyl-4-methylenepyrrolidine | 53 |
| 7-12 | 2-(TMS-ethynyl)phenyl with CH(OSi^tBuMe₂)CH₂CH₂CH₃ side chain | H₂O | 4-(trimethylsilylmethylene)-3-methyl-1-(OSi^tBuMe₂)-tetralin | 47 |
| 7-13 | 2-(TMS-ethynyl)phenyl with CH(OSi^tBuMe₂)CH=CH₂ side chain | H₂O | 1-(trimethylsilylmethylene)-2-methyl-3-(OSi^tBuMe₂)-indane | 46 |
| 7-14 | PhCH₂OCH₂-C(CH₂OCH₂Ph)(CH₂C≡C-TMS)(CH₂CH=CH-CH=CH₂) | H₂O | cyclopentane products with TMS-methylene and allyl / propenyl substituents | 90 |
| 7-15 | TMS-C≡C-(CH₂)₄-CH=C=CH-Si(Me)₂Ph | H₂O | 1-(TMS-methylene)-2-(vinyl-Si(Me)₂Ph)cyclopentane | 80 |

Reaction Product in Example 7-2

¹H-NMR, δ: 1.11 (t, J=12.3 Hz, 1H) 2.03 (dd, J=2.9, 14.9 Hz, 1H) 2.17 (dd, J=8.5, 4.1 Hz, 1H) 2.54–2.64 (m, 1H) 3.05–3.20 (m, 1H) 3.22–3.63 (m, 4H) 4.35–4.60 (m, 4H) 5.82–5.86 (m, 1H) 7.17–7.49 (m, 10H)

IR: 3030, 2850, 1700 (C=O), 1630, 1455, 1410, 1360, 1260, 1205, 1090, 905, 830, 740, 700 (cm⁻¹)

Reaction Product in Example 7-3

¹H-NMR, δ: 0.83 and 0.90 (2d, J=6.8 Hz and 6.0 Hz, 6H) 1.03 and 1.24 (2dd, J=13.1 Hz and13.6 Hz, 2H) 1.67 and 1.79 (2dd, J=6.6, 5.3, 6.6 Hz and 7.4, 6.1, 7.5 Hz, 2H) 1.18–1.43 and 1.96–2.08 (m, 2H) 3.34 and 3.40 (s, 4H) 4.51 (s, 4H) 7.22–7.40 (m, 10H)

IR: 3025, 2850, 1600, 1450, 1355, 1245, 1200, 1090, 900, 835, 730, 690 (cm⁻¹)

Reaction Product in Example 7-4

$^1$H-NMR, δ: 1.45 (dd, J=6.8, 7.2 Hz, 2H) 1.94 (dd, J=8.2, 5.6 Hz, 2H) 2.11 (dd, J=4.8, 14.7 Hz, 2H) 2.41 (dd, J=9.1, 8.4 Hz, 2H) 2.57–2.81 (m, 2H) 3.34 (s, 2H) 3.40 (s, 2H) 4.35–4.55 (m, 4H) 7.15–7.38 (m, 10H)

IR: 2850, 1735, 1455, 1410, 1360, 1200, 1100, 1030, 910, 740, 695 (cm$^{-1}$)

Reaction Product in Example 7-5

$^1$H-NMR, δ: 0.17 (s, 18H) 2.47 (d, J=2.1 Hz) 3.42 (s, 4H) 4.55 (s, 4H) 6.00–6.09 (m, 2H) 7.25–7.45 (m, 10H)

$^{13}$C-NMR, δ: −0.46, 38.60, 45.15, 72.95, 73.27, 118.29, 127.34, 127.40, 128.25, 138.81, 156.30

IR: 3030, 2950, 2850, 1600, 1450, 1360, 1245, 1100, 840, 730, 690 (cm$^{-1}$)

Reaction Product in Example 7-6

$^1$H-NMR, δ: 0.09 (s, 9H) 1.03 (d, J=6.7 Hz, 3H) 1.07 (dd, J=12.8 Hz, 2.0 Hz, 1H) 1.94 (dd, J=12.9 Hz, 4.7 Hz, 1H) 2.30–2.36 (m, 2H) 2.40–2.57 (m, 2H) 3.30–3.42 (m, 4H) 4.45–4.53 (m, 4H) 5.18–5.28 (m, 1H) 7.20–7.37 (m, 10H)

$^{13}$C-NMR, 6−0.19, 18.74, 39.24, 39.88, 45.80, 73.07, 73.78, 74.88, 117.19, 127.29, 127.32, 127.39, 128.23, 138.91, 165.85

IR: 3025, 2850, 1620, 1450, 1355, 1240, 1200, 1090, 835, 730, 690 (cm$^{-1}$)

Reaction Product in Example 7-7

$^1$H-NMR, 65: 0.08 (s, 9H) 1.07 (dd, J=10.9, 2.0 Hz, 1H) 1.94 (dd, J=8.3, 4.6 Hz, 1H) 2.40–2.55 (m, 1H) 3.27–3.43 (m, 4H) 4.51 (s, 4H) 7.22–7.42 (m, 10H)

Reaction Product in Example 7-10

$^1$H-NMR, δ: 0.82–0.96 (m, 3H) 1.06–1.14 (m, 3H) 1.20–1.70 (m, 8H) 2.60–2.82 (m, 1H) 3.24 and 3.44 and 3.93 and 4.11 (4dd, J=8.3, 6.5, 7.4, 7.7 Hz, 2H) 4.24–4.37 (m, 1H) 4.80–4.92 (m, 2H)

$^{13}$C-NMR, δ: 14.01, 15.05, 17.38, 22.61, 25.04, 25.57, 31.90, 35.13, 35.76, 38.47, 38.75, 73.15, 74.12, 81.14, 81.45, 102.75, 103.07, 157.13, 157.23

IR: 2920, 2850, 1660, 1450, 1375, 1260, 1080, 1030, 880, 800 (cm$^{-1}$)

Reaction Product in Example 7-12

$^1$H-NMR, δ: 0.00 and 0.03 (2s, 9H) 0.08 and 0.12 (2s, 6H) 0.80–1.00 (m, 9H) 1.08 and 1.14 (2d, J=6.9, 6.9 Hz, 3H) 1.62–1.73 and 1.97–2.09 and 2.18–2.40 and 2.65–2.85 (4m, 3H) 4.60 and 4.76 (q and t, J=5.2, 5.6, 5.2 Hz and J=5.8 Hz, 1H) 5.43–5.47 (m, 1H) 7.15–7.52 (m, 6H)

Reaction Product in Example 7-14 (mixture)

$^1$H-NMR, δ: 0.10 (s, 9H) 1.21 (d/d, J=9, 14 Hz, 1H) 1.27 (d/d, J=9, 14 Hz, 1H) 1.33 (d/d, J=9, 14 Hz, 1H) 1.64 (d, J=7 Hz, 3H) 1.71 (d, J=7 Hz, 3H) 1.91 (d/d, J=8, 14 Hz, 1H) 1.96 (d/d, J=8, 14 Hz, 1H) 2.00 (d/d, J=8, 14 Hz, 1H) 2.38 (m, 2H) 2.38 (m, 2H) 2.53 (m, 1H) 3.06 (br q, J=8 Hz) 3.35–3.48 (m, 4H) 3.47 (br q, J=8 Hz, 1H) 4.48–4.60 (m, 4H) 4.99 (d, J=9 Hz, 1H) 5.04 (d, J=16 Hz, 1H) 5.20 (m, 1H) 5.22 (m, 1H) 5.33 (m, 1H) 5.42 (d/q, J=15.7 Hz) 5.58 (d/q, J=11.7 Hz) 5.80 (symmetric m, 1H) 7.32 (m, 10H)

IR (neat): 3100, 2940, 2860, 1670, 1640, 1470, 1380, 1260 (Me-Si), 1070, 990, 970, 920, 890 (cm$^{-1}$)

Reaction Product in Example 7-15

$^1$H-NMR, δ: 0.08 (s, 9H) 0.32 (s, 3H) 0.36 (s, 3H) 1.32 (m, 1H) 1.46 (m, 1H) 1.75 (m, 2H) 2.26 (m, 2H) 2.40 (dd, J=7.5, 14 Hz, 1H) 3.04 (q, J=7.5 Hz, 1H) 5.21 (s, 1H) 5.74 (d, J=15 Hz, 1H) 6.17 (dd, J=7.5, 15 Hz, 1H)

EXAMPLE 7-16

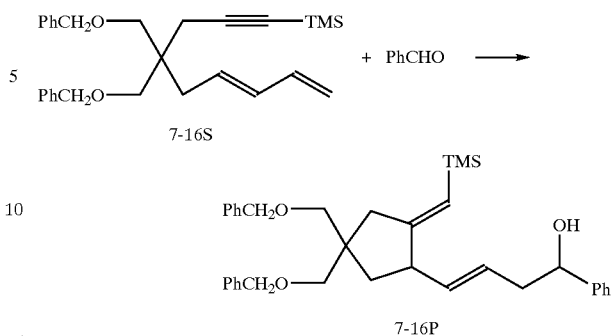

To 9.5 ml of ethyl ether were added under an argon atmosphere 0.37 ml (1.26 mmol) of tetraisopropoxytitanium and 432 mg (1.0 mmol) of the unsaturated compound 7-16S. After cooling to −78° C., the reaction liquid was given dropwise 2.55 ml (2.77 mmol) of isopropylmagnesium chloride. The reaction liquid was stirred at −78° C. for 30 minutes, heated to −50° C. over 30 minutes, and stirred for 2 hours. After cooling again to −78° C., the reaction liquid was given 0.102 ml (1.0 mmol) of benzaldehyde and heated to −40° C. and stirred for 1 hour. The reaction liquid was given 2 ml of 3N hydrochloric acid. The reaction liquid was heated to room temperature and extracted with hexane-ether mixture. The organic layer was washed with a saturated aqueous solution of sodium hydrogen carbonate and a saturated aqueous solution of sodium chloride. The solution was dried with anhydrous magnesium sulfate and freed of solvent by vacuum distillation. The residues were purified by silica gel chromatography. Thus there was obtained 518 mg of 7-16P in the cyclized form (yields: 96%).

Reaction Product in Example 7-16

$^1$H-NMR, δ: 0.06 (s, 9H) 1.32 (d/d, J=10, 14 Hz, 1H) 1.94 (d/d, J=10, 14 Hz, 1H) 2.07 (d, J=3 Hz, 1H) 2.27 (d/m, J=16 Hz, 1H) 2.48 (d, J=16 Hz, 1H) 2.50 (m, 2H) 3.06 (br m, 1H) 3.37 (d, J=11 Hz, 1H) 3.37 (s, 2H) 3.39 (d, J=11 Hz, 1H) 4.50 (s, 4H) 4.70 (d/t, J=3, 7.5 Hz, 1H) 5.20 (q, J=2 Hz, 1H) 5.34 (symmetric m, 2H) 7.29 (m, 15 Hz)

$^{13}$C-NMR, δ: 38.13, 38.95, 42.54, 46.46, 49.19, 72.86, 73.21, 73.56, 74.57, 120.28, 125.87, 126.48, 126.53, 127.34, 127.40, 128.24, 128.31, 137.19, 138.82, 163.08

IR (neat): 3400 (br, OH), 3050, 3025, 2940, 2840, 1610, 1490, 1450, 1360, 1240 (Me-Si), 1090, 1020, 900, 860, 830, 720, 680 (cm$^{-1}$)

EXAMPLES 7-17 TO 7-24

The procedure of Example 7-1 was repeated except that the unsaturated compound and terminator were replaced by those shown in Table 12. There were obtained corresponding cyclized compounds as shown in Table 12.

TABLE 12

| Example | Starting material | Terminator | Reaction product | Yields (%) |
|---|---|---|---|---|
| 7-17 | (alkyne-TMS, OCO₂Et chain) | H₂O | (cyclopentane with =CH-TMS and vinyl) | 85 |
| 7-18 | (alkyne-TMS, OCO₂Et chain) | I₂ | (cyclopentane with =C(TMS)I and vinyl) | 80 |
| 7-19 | (alkyne-TMS, OCO₂Et chain) | H₂O | (cyclohexane with =CH-TMS and vinyl) | 82 |
| 7-20 | (alkyne-Ph, OCO₂Et chain) | H₂O | (cyclopentane with =CH-Ph and vinyl) | 75 |
| 7-21 | (alkyne-C₅H₁₁, OCO₂Et chain) | H₂O | (cyclopentane with =CH-C₅H₁₁ and vinyl) | 77 |
| 7-22 | PhCH₂O—, PhCH₂O— substituted diene with OAc | H₂O | PhCH₂O—, PhCH₂O— substituted cyclopentane with methyl and vinyl | 70 |
| 7-23 | (diyne-C₅H₁₁, OAc) | H₂O | (cyclopentane with =CH-C₅H₁₁ and allene) | 86 |
| 7-24 | (alkyne-TMS, OCO₂Et) | H₂O | (cyclohexane with =CH-TMS, methyl, OCO₂Et) | 82 |

Reaction Product in Example 7-17
¹H-NMR, δ: 0.085 (s, 9H) 1.35–1.48 (m, 1H) 1.51–1.67 (m, 1H) 1.73–1.97 (m, 2H) 2.21–2.36 (m, 1H) 2.39–2.45 (m, 1H) 2.93 (td, J=7.8, 8.1 Hz, 1H) 4.97–5.06 (m, 2H) 5.25–5.30 (m, 1H) 5.63 (ddd, J=16.8, 8.1, 10.2 Hz, 1H)
¹³C-NMR, δ: 0.36, 24.87, 32.35, 33.19, 52.71, 114.79, 119.36, 141.27, 163.95
IR (neat): 2960, 2870, 1625, 1250, 995, 915, 870, 850, 685 (cm⁻¹)

Reaction Product in Example 7-18
¹H-NMR, δ: 0.26 (s, 9H) 1.63–1.76 (m, 1H) 1.77–1.97 (m, 3H) 2.27–2.49 (m, 2H) 3.47–3.52 (m, 1H) 5.06 (ddd, J=16.9, 1.7, 1.7 Hz, 1H) 5.07–5.13 (m, 1H) 5.73 (ddd, J=16.9, 10.6, 6.1 Hz, 1H)
¹³C-NMR, δ: 1.05, 26.00, 31.40, 33.51, 57.74, 102.10, 114.71, 137.27, 163.74
IR (neat): 3425, 2960, 1635, 1600, 1410, 1250, 910, 880, 840, 755, 690 (cm⁻¹)

Reaction Product in Example 7-19

¹H-NMR, δ: 0.09 (s, 9H) 1.33–1.52 (m, 3H) 1.65–1.85 (m, 3H) 1.99–2.08 (m, 1H) 2.43–2.51 (m, 1H) 2.69–2.76 (m, 1H) 4.96–5.08 (m, 2H) 5.11 (s, 1H) 5.99 (ddd, J=17.4, 7.1, 10.4 Hz, 1H)

¹³C-NMR, δ: 0.36, 24.86, 34.20, 34.29, 50.86, 114.35, 119.93, 141.37, 161.04

IR (neat): 2940, 2860, 1615, 1450, 1250, 915, 890, 840

Reaction Product in Example 7-20

¹H-NMR, δ: 1.42–1.54 (m, 1H) 1.59–1.76 (m, 1H) 1.84–2.01 (m, 2H) 2.55–2.64 (m, 1H) 2.65–2.76 (m, 1H) 3.16 (td, J=7.7, 8.2 Hz, 1H) 5.07–5.14 (m, 2H) 5.75 (ddd, J=16.8, 8.2, 10.2 Hz, 1H) 6.21 (m, 1H) 7.11–7.22 (m, 1H) 7.27–7.37 (m, 4H)

¹³C-NMR, δ: 25.27, 31.40, 33.17, 51.66, 114.94, 122.53, 125.86, 128.10, 128.16, 138.67, 141.24, 148.33

IR (neat): 3400, 2945, 2850, 1630, 1595, 1485, 1440, 985, 905, 740, 680 (cm⁻¹)

Reaction Product in Example 7-21

¹H-NMR, δ: 0.88 (t, J=6.6 Hz, 3H) 1.22–1.46 (m, 7H) 1.48–1.63 (m, 1H) 1.71–2.23 (m, 4H) 2.13–2.36 (m, 2H) 2.84–2.98 (m, 1H) 4.96–5.03 (m, 2H) 5.08–5.16 (m, 1H) 5.58–5.70 (m, 1H)

¹³C-NMR, δ: 14.07, 22.61, 24.51, 28.85, 29.30, 29.55, 31.64, 33.94, 49.66, 114.00, 122.27, 141.85, 144.58

IR (neat): 3410, 2960, 2930, 2850, 1640, 1470, 990, 910 (cm⁻¹)

Reaction Product in Example 7-22

¹H-NMR, δ anti: 0.91 (d, J=6.4 Hz, 3H) 1.08 (dd, J=11.1, 13.0 Hz, 1H) 1.30 (dd, J=11.1, 13.2 Hz, 1H) 1.51–1.73 (m, 1H) 1.81 (dd, J=7.7, 7.7 Hz, 1H) 1.85 (dd, J=7.7, 7.7 Hz, 1H) 1.89–2.20 (m, 1H) 3.35 (s, 4H) 4.51 (s, 4H) 4.90–5.00 (m, 2H) 5.56–5.69 (m, 1H) 7.21–7.36 (m, 10H)

¹³C-NMR, δ anti: 17.74, 39.71, 39.82, 41.64, 45.85, 51.75, 73.19, 75.25, 75.34, 113.96, 127.27, 127.33, 128.22, 138.98, 141.78

IR (neat): 3425, 3040, 2960, 2860, 1640, 1460, 1365, 1105, 915, 735, 695 (cm⁻¹)

Reaction Product in Example 7-23

¹H-NMR, δ: 0.89 (t, J=6.9 Hz, 3H) 1.23–1.44 (m, 6H) 1.68–1.78 (m, 2H) 2.08 (td, J=7.4, 7.5 Hz, 2H) 2.33 (t, J=7.2 Hz, 2H) 2.46–2.54 (m, 2H) 4.96–5.01 (m, 2H) 5.58 (t, J=7.5 Hz, 1H)

¹³C-NMR, δ: 14.02, 22.58, 25.04, 29.21, 29.82, 30.00, 31.63, 31.75, 78.70, 105.75, 123.97, 137.65, 202.89

IR (neat): 3350, 2960, 2930, 2855, 1950, 1670, 1470, 1445, 1380, 850 (cm⁻¹)

Reaction Product in Example 7-24

¹H-NMR, δ: 0.01 (s, 1H) 1.07 (d, J=6.6 Hz, 2H) 1.31 (t, J=7.1 Hz, 3H) 1.33–1.44 (m, 1H) 1.51–1.65 (m, 1H) 1.77–1.88 (m, 1H) 1.89–2.00 (m, 1H) 2.25–2.35 (m, 1H) 2.45–2.53 (m, 1H) 4.18 (q, J=7.1 Hz, 2H) 4.28 (td, J=9.6, 4.3 Hz, 1H) 5.26 (s, 1H)

¹³C-NMR, δ: 0.29, 14.27, 14.38, 30.87, 33.65, 45.54, 63.68, 81.96, 121.50, 154.85, 157.96

IR (neat): 2960, 2870, 1750, 1620, 1465, 1380, 1250, 1150, 970, 885, 840 (cm⁻¹)

EXAMPLE 7-25

As in Example 7-16, reaction was performed on 250 mg (0.93 mmol) of 7-25S, 0.34 ml (1.67 mmol) of tetraisopropoxytitanium, and 2.56 mmol of isopropylmagnesium bromide. Upon further reaction with 0.14 ml (1.4 mmol) of benzaldehyde, there was obtained 160 mg of 7-25P in the cyclized form (yields: 67%).

EXAMPLES 7-26 AND 7-27

As in Example 7-25, aldehydes (as starting materials) shown in Table 13 gave reaction products as shown in Table 13.

TABLE 13

| Example | Starting material | Aldehyde | Reaction product | Yields (%) |
|---|---|---|---|---|
| 7-25 | (structure with TMS alkyne, OCO₂Et) | PhCHO | (cyclopentane with TMS, Ph, OH, vinyl) | 67 |
| 7-26 | (PhCH₂O-substituted, TMS alkyne, allyl) | PhCHO | (cyclopentane with PhCH₂O groups, TMS, Ph, OH, methyl) | 54 |

TABLE 13-continued

| Example | Starting material | Aldehyde | Reaction product | Yields (%) |
|---|---|---|---|---|
| 7-27 | PhCH₂O—⟨⟩—≡—TMS<br>PhCH₂O—⟨⟩—≡—TMS | PhCH₂CH₂CHO | (cyclobutane product with TMS, PhCH₂O, OH, Ph groups) | 81 |

Reaction Product in Example 7-25
¹H-NMR, δ: −0.02 (s, 9H) 1.59–1.91 (m, 4H) 2.51 (dd, J=6.9, 6.9 Hz, 2H) 3.54–3.60 (m, 1H) 4.80–4.94 (m, 2H) 5.72–5.84 (m, 2H) 7.16–7.37 (m, 5H)
¹³C-NMR, δ: 1.08, 24.08, 32.98, 33.60, 47.36, 74.66, 113.62, 126.03, 126.34, 127.69, 135.22, 141.59, 141.59, 143.59, 159.16
IR (neat): 3460, 1640, 1605, 1500, 1250, 1010, 845, 750, 700 (cm⁻¹)

Reaction Product in Example 7-26
¹H-NMR, δ: −0.4 (s, 9H) 0.97 (d, J=7.7 Hz, 3H) 1.30 (d/d, J=6, 14 Hz, 1H) 1.58 (br s, 1H) 1.95 (d/d, J=8, 14 Hz, 1H) 2.39 (d, J=15 Hz, 1H) 2.61 (d, J=15 Hz, 1H) 2.94 (sextet, J=7.7 Hz, 1H) 3.28 (d, J=8 Hz, 1H) 3.31 (d, J=8 Hz, 1H) 3.46 (d, J=8.5 Hz, 1H) 3.55 (d, J=8.5 Hz, 1H) 4.42 (d, J=12 Hz, 1H) 4.54 (d, J=12 Hz, 1H) 4.54 (s, 2H) 5.70 (s, 1H) 7.20–7.40 (m, 15H)

Reaction Product in Example 7-27
¹H-NMR, δ: 0.18 (s, 9H) 0.23 (s, 96) 1.60 (br s, 1H) 1.80 (m, 1H) 2.12 (m, 1H) 2.28 (d, J=15 Hz, 1H) 2.29 (d, J=15 Hz, 1H) 2.42 (d, J=15 Hz, 1H) 2.49 (d, J=15 Hz, 1H) 2.68 (m, 1H) 2.89 (m, 1H) 3.34–3.46 (m, 4H) 4.45–4.58 (m, 4H) 4.98 (d, J=8.5 Hz) 5.41 (br s, 1H) 7.18–7.40 (m, 15H)

EXAMPLE 8-1

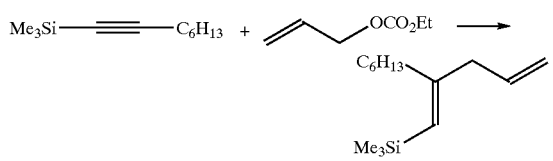

To 9 ml of ethyl ether solution containing 170 mg (0.934 mmol) of 1-trimethylsilyl-1-octyne, 121 mg (0.934 mmol) of allyl carbonate, and 0.342 ml (1.17 mmol) of tetraisopropoxytitanium was added dropwise at −78° C. 1.72 ml of 1.49M ethyl ether solution containing isopropylmagnesium bromide (2.57 mmol). After heating to −50° C. over 30 minutes, the reaction liquid was stirred for 2 hours. The reaction liquid was cooled to −78° C. again and given 2 ml of water. The reaction liquid was stirred together with 10 ml of 1N hydrochloric acid for 30 minutes. After extraction with hexane, the organic layer was dried with anhydrous magnesium sulfate and freed of solvent by vacuum distillation. The residues were purified by silica gel chromatography. Thus there was obtained 1-trimethyl-2-hexyl-1,4-pentadiens in a yield of 83%.

EXAMPLES 8-2 TO 8-11

The procedure of Example 8-1 was repeated except that the 1-trimethylsilyl-1-octyne and allyl carbonate were replaced those shown in Table 14. There were obtained corresponding dienes in respective yields as shown in Table 14.

TABLE 14

| Example | Acetylene compound | Allyl compound | Reaction product | Yields (%) |
|---|---|---|---|---|
| 8-1 | Me₃Si—≡—C₆H₁₃ | ⟋⟍OCO₂Et | C₆H₁₃\C(=CHMe₃Si)/CH₂CH=CH₂ | 83 |
| 8-2 | Me₃Si—≡—C₆H₁₃ | ⟋⟍Cl | C₆H₁₃\C(=CHMe₃Si)/CH₂CH=CH₂ | 72 |

TABLE 14-continued

| Example | Acetylene compound | Allyl compound | Reaction product | Yields (%) |
|---|---|---|---|---|
| 8-3 | Me$_3$Si—≡—C$_6$H$_{13}$ | ⁀OPh | C$_6$H$_{13}$ / Me$_3$Si | 80 |
| 8-4 | Me$_3$Si—≡—C$_6$H$_{13}$ | ⁀OAc | C$_6$H$_{13}$ / Me$_3$Si | 55 |
| 8-5 | Me$_3$Si—≡—C$_6$H$_{13}$ | ⁀OCO$_2$Et (D$_2$O termination) | C$_6$H$_{13}$ / Me$_3$Si D | 77 |
| 8-6 | Me$_3$Si—≡—C$_6$H$_{13}$ | ⁀CH(OEt)$_2$ | C$_6$H$_{13}$ / Me$_3$Si ~OEt | 64 (E:Z = 95:5) |
| 8-7 | Me$_3$Si—≡—C$_6$H$_{13}$ | methallyl OCO$_2$Et | C$_6$H$_{13}$ / Me$_3$Si | 20 |
| 8-8 | Me$_3$Si—≡—C$_6$H$_{13}$ | crotyl OCO$_2$Et | C$_6$H$_{13}$ / Me$_3$Si | 16 |
| 8-9 | Ph—≡—Me | ⁀OCO$_2$Et | Me / Ph | 65 |
| 8-10 | C$_3$H$_7$—≡—C$_3$H$_7$ | ⁀OCO$_2$Et | C$_3$H$_7$ / C$_3$H$_7$ | 66 |
| 8-11 | C$_3$H$_7$—≡—C$_3$H$_7$ | ⁀OCO$_2$Et (D$_2$O termination) | C$_3$H$_7$ / C$_3$H$_7$ D | 70 |

Reaction Product in Example 8-1
$^1$H-NMR, δ: 0.097 (s, 9H) 0.89 (t, J=6.7 Hz, 3H) 1.23–1.47 (m, 8H) 2.12 (t, J=7.9 Hz, 2H) 2.82 (d, J=7.0 Hz, 2H) 4.99–5.03 (m, 1H) 5.06 (s, 1H) 5.20 (s, 1H) 5.73–5.88 (m, 1H)
$^{13}$C-NMR, δ: 0.37, 14.05, 22.62, 29.03, 29.59, 31.82, 36.24, 115.90, 124.30, 136.88, 157.96
IR: 2930, 1610, 1250, 840 (cm$^{-1}$)
Elemental analysis value C$_{14}$H$_{26}$Si:
Calculated value C,74.92; H,12.57. Found value C,74.90; H,12.49.
Reaction Product in Example 8-6
(E isomer)
$^1$H-NMR, δ: 0.085 (s, 9H) 0.89 (t, J=6.7 Hz, 3H) 1.18–1.44 (m, 11H) 2.11 (t, J=7.8 Hz, 2H) 2.66 (d, J=7.4 Hz, 2H) 3.74 (q, J=14.0 Hz, 2H) 4.70–4.80 (m, 1H) 5.22 (s, 1H) 6.20 (d, J=12.5 Hz, 1H)
$^{13}$C-NMR, δ: 0.396, 14.03, 14.77, 22.61, 29.10, 29.61, 31.82, 36.04, 37.20, 64.69, 102.14, 123.20, 147.08, 159.41
IR: 2918, 1645, 1607, 1245, 1200, 1153, 832 (cm$^{-1}$)
(Z isomer)
$^1$H-NMR, δ: 0.085 (s, 9H) 0.89 (t, J=6.7 Hz, 3H) 1.18–1.44 (m, 11H) 2.11 (t, J=7.8 Hz, 2H) 2.86 (d, J=7.4 Hz, 2H) 3.78 (q, J=12.8 Hz, 2H) 4.37 (q, J=13.8 Hz, 1H) 5.21 (s, 1H) 6.01 (d, J=6.2 Hz, 1H)
$^{13}$C-NMR, δ: 0.396, 14.03, 15.26, 22.61, 29.10, 29.61, 33.57, 36.32, 37.20, 67.49, 104.88, 122.62, 145.23, 159.08

Reaction Product in Example 8-7

¹H-NMR, δ: 0.097 (s, 9H) 0.89 (t, J=6.6 Hz, 3H) 1.23–1.42 (m, 8H) 1.65 (s, 3H) 2.07 (t, J=7.9 Hz, 2H) 2.78 (s, 2H) 4.7130 (s, 1H) 4.7963 (s, 1H) 5.22 (s, 1H)

¹³C-NMR, δ: 0.34, 14.05, 21.84, 22.63, 29.12, 29.71, 31.82, 35.45, 48.43, 112.16, 125.57, 144.06, 157.16

Reaction Product in Example 8-8

¹H-NMR, δ: 0.11 (s, 9H) 0.88 (t, J=6.2 Hz, 3H) 1.10 (d, J=6.9 Hz, 3H) 1.22–1.45 (m, 8H) 2.07–2.14 (m, 2H) 2.78–2.88 (m, 1H) 4.91–5.01 (m, 2H) 5.20 (s, 1H) 5.68–5.80 (m, 1H)

Reaction Product in Example 8-9

¹H-NMR, δ: 1.86 (s, 3H) 2.91 (d, J=6.8 Hz, 2H) 5.07–5.16 (m, 2H) 5.82–5.96 (m, 1H) 6.30 (s, 1H) 7.16–7.34 (m, 5H)

¹³C-NMR, δ: 17.80, 44.95, 116.28, 125.75, 125.94, 127.99, 128.78, 136.38, 137.28, 138.43

IR: 2907, 1639, 1602, 997, 918, 740, 700 (cm⁻¹)

Reaction Product in Example 8-10

¹H-NMR, δ: 0.87–0.93 (m, 6H) 1.30–1.42 (m, 4H) 1.95–2.02 (m, 4H) 2.72 (d, J=6.7 Hz, 2H) 4.98–5.05 (m, 2H) 5.17 (t, J=7.3 Hz, 1H) 5.72–5.86 (m, 1H)

¹³C-NMR, δ: 13.87, 14.10, 21.43, 23.17, 29.94, 32.18, 41.53, 115.29, 126.19, 137.58, 137.64

IR: 2922, 2870, 1636, 1458, 995, 910 (cm⁻¹)

EXAMPLE 9-1

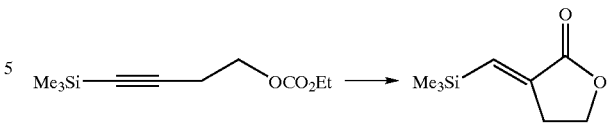

To 7.5 ml of ethyl ether solution containing 284 ml (1.0 mmol) of tetraisopropoxytitanium and 0.5 mmol of 1-trimethylsilyl-1-butyne-4-carbonate was added dropwise at −50° C. 1.54 ml of 1.3M ethyl ether solution containing isopropylmagnesium bromide (2 mmol). The reaction liquid was stirred at −45° C. to −40° C. for 1 hour. The reaction liquid was given 5 ml of 1N hydrochloric acid at −40° C. and then heated to room temperature and stirred for 30 minutes. After layer separation, the organic layer was washed with a saturated aqueous solution of sodium hydrogen carbonate, dried with anhydrous magnesium sulfate, and freed of solvent by vacuum distillation. The residues were purified by silica gel chromatography. Thus there was obtained lactone in a yield of 81%.

EXAMPLES 9-2 TO 9-10

The procedure of Example 9-1 was repeated except that the 1-trimethylsilyl-1-butyne-4-carbonate and terminator (1N hydrochloric acid) were replaced by those shown in Tables 15 and 16. There were obtained corresponding lactones or α,β-unsaturated esters in respective yields as shown in Tables 15 and 16.

TABLE 15

| Example | Starting material | Terminator | Reaction product | Yields (%) |
|---|---|---|---|---|
| 9-1 | Me₃Si—≡—⁀OCO₂Et | H₂O | Me₃Si lactone structure | 81 |
| 9-2 | Me₃Si—≡—CH(Et)—OCO₂Et | H₂O | Me₃Si lactone with Et | 84 |
| 9-3 | Me₃Si—≡—CH(Et)—OCO₂Et | D₂O | Me₃Si D-lactone with Et | 88 |
| 9-4 | C₆H₁₃—≡—⁀OCO₂Et | H₂O | C₆H₁₃ lactone structure; C₆H₁₃ CO₂Et/OH acyclic | 62; 20 |

TABLE 15-continued

| Example | Starting material | Terminator | Reaction product | Yields (%) |
|---|---|---|---|---|
| 9-5 | Me₃Si—≡—CH₂CH₂CH₂OCO₂Et | H₂O | Me₃Si-substituted δ-valerolactone (exocyclic =CH) | 76 |
| 9-6 | Me₃Si—≡—CH₂CH₂CH₂OCO₂Et | I₂ | I,Me₃Si-substituted δ-valerolactone | 74 |
| 9-7 | Et—≡—CH₂CH₂CH₂OCO₂Et | H₂O | Et-substituted δ-valerolactone | 65 |

TABLE 16

| Example | Starting material | Terminator | Reaction product | Yields (%) |
|---|---|---|---|---|
| 9-8 | Et—≡—CH₂CH₂CH₂OCO₂Et | D₂O | D,Et-substituted δ-valerolactone | 63 |
| 9-9 | Me₃Si—≡—CH₂CH₂CH₂CH₂OCO₂Et | H₂O | Me₃Si—CH=C(CO₂Et)—CH₂CH₂CH₂CH₂OH | 66 |
| 9-10 | Me₃Si—≡—CH₂CH₂CH₂CH₂OCO₂Et | D₂O | Me₃Si—CD=C(CO₂Et)—CH₂CH₂CH₂CH₂OH | 64 |

Reaction Product in Example 9-1

¹H-NMR, δ: 0.22 (s, 9H) 2.98 (d/t, J=2.1, 6.6 Hz, 2H) 4.40 (t, J=6.6 Hz, 2H) 6.97 (t, J=2.1 Hz, 1H)

¹³C-NMR, δ: −1.49, 27.23, 64.92, 138.79, 139.46, 170.39

Reaction Product in Example 9-2

¹H-NMR, δ: 0.17 (s, 9H) 0.98 (t, J=6.9 Hz, 3H) 1.67 (m, 2H) 2.50 (d/d/d, J=17.4, 6.0, 2.4 Hz, 1H) 3.01 (d/d/d, J=17.4, 6.6, 2.4 Hz, 1H) 4.43 (t/t, J=6.3, 6.3 Hz, 1H) 6.88 (t, J=2.4 Hz, 1H)

¹³C-NMR, δ: −1.49, 8.89, 29.18, 33.02, 78.18, 138.94, 140.16, 170.00

Reaction Product in Example 9-4

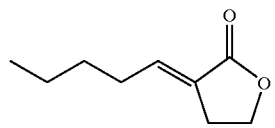

¹H-NMR, δ: 0.89 (t, J=6.8 Hz, 3H) 1.30 (m, 6H) 1.49 (m, 2H) 2.20 (d/t, J=7.2, 7.2 Hz, 2H) 2.87 (m, 2H) 4.37 (t, J=7.8 Hz, 2H) 6.74 (m, 1H)

¹³C-NMR, δ: 13.93, 22.44, 25.02, 28.03, 28.89, 30.16, 31.51, 65.27, 125.08, 140.93, 171.10

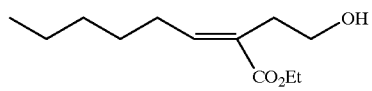

¹H-NMR, δ: 0.89 (t, J=6.9 Hz, 3H) 1.31 (m, 9H) 1.45 (m, 2H) 1.90 (br s, OH) 2.22 (d/t, J=7.5, 7.2 Hz, 2H) 2.60 (t, J=6.6 Hz, 2H) 3.69 (t, J=6.6 Hz, 2H) 4.20 (q, J=6.9 Hz, 2H) 6.89 (t, J=7.5 Hz, 1H)

Reaction Product in Example 9-5

¹H-NMR, δ: 0.14 (s, 9H) 1.92 (t/t, J=6.6, 5.4 Hz, 2H) 2.65 (t, J=6.6 Hz, 2H) 4.30 (t/d, J=5.4, 2.1 Hz, 2H) 7.18 (t, J=2.1 Hz, 1H)

¹³C-NMR, δ: −1.49, 23.21, 27.78, 69.00, 139.86, 145.62, 165.60

Reaction Product in Example 9-6
$^1$H-NMR, δ: 0.37 (s, 9H) 2.04 (m, 2H) 2.74 (m, 2H) 4.2 (m, 2H)
$^{13}$C-NMR, δ: 1.50; 23.07, 28.77, 66.49, 113.87, 144.69, 167.30

Reaction Product in Example 9-7
$^1$H-NMR, δ: 1.02 (t, J=7.5 Hz, 3H) 1.91 (t/t, J=6.3, 5.7 Hz, 2H) 2.13 (d/q, J=7.5, 7.5 Hz, 2H) 2.50 (m, 2H) 4.28 (t, J=5.7 Hz, 2H) 7.00 (m, 1H)
$^{13}$C-NMR, δ: 12.39, 21.43, 22.48, 23.28, 68.36, 124.79, 147.59, 166.50

Reaction Product in Example 9-9
$^1$H-NMR, δ: 0.19 (s, 9H) 1.30 (t, J=6.9 Hz, 3H) 1.45–1.70 (m, 4H) 2.09 (br s, OH) 2.41 (m, 2H) 3.66 (t, J=6.0 Hz, 2H) 4.19 (q, J=6.9 Hz, 2H) 6.81 (s, 1H)

EXAMPLE 9-11

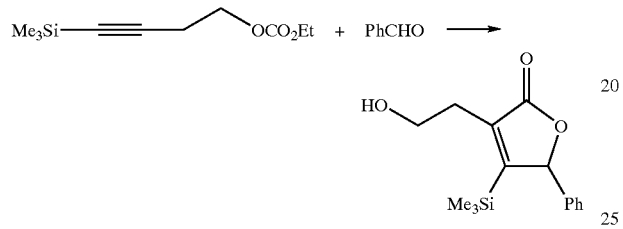

To 7.5 ml of ethyl ether solution containing 369 ml (1.3 mmol) of tetraisopropoxytitanium and 1.0 mmol of 1-trimethylsilyl-1-butyne-4-carbonate was added dropwise at −50° C. 2 ml of 1.3M ethyl ether solution containing isopropylmagnesium bromide (2.6 mmol). The reaction liquid was stirred at −45° C. to −40° C. for 1 hour. The reaction liquid was given 212 mg (2 mmol) of benzaldehyde at −40° C. The reaction liquid was heated to 0° C. over 1 hour, given 5 ml of 1N hydrochloric acid, heated to room temperature, and stirred for 30 minutes. After layer separation, the organic layer was washed with a saturated aqueous solution of sodium hydrogen carbonate, dried with anhydrous magnesium sulfate, and freed of solvent by vacuum distillation. The residues were purified by silica gel chromatography. Thus there was obtained a product in cyclized form in a yield of 65%.

EXAMPLE 9-12 TO 9-16

The procedure of Example 9-11 was repeated except that the 1-trimethylsilyl-1-butyne-4-carbonate was replaced by those shown in Table 17. There were obtained corresponding products cyclized form in respective yields as shown in Table 17.

TABLE 17

| Example | Acetylene compound | Reaction product | Yields (%) |
|---|---|---|---|
| 9-11 | Me₃Si—≡—CH₂CH₂OCO₂Et | lactone with HO-CH₂CH₂, Me₃Si, Ph substituents | 65 |
| 9-12 | Me₃Si—≡—CH(Et)OCO₂Et | lactone with Et-CH₂CH(OH)-, Me₃Si, Ph substituents | 50 |
| 9-13 | C₆H₁₃—≡—CH₂CH₂OCO₂Et | lactone with Ph-CH(OH)-, C₆H₁₃ substituents (furanone) | 56 |
|  |  | lactone with HO-CH₂CH₂, C₆H₁₃, Ph substituents | 12 |

TABLE 17-continued

| Example | Acetylene compound | Reaction product | Yields (%) |
|---|---|---|---|
| 9-14 | Me₃Si—≡—CH₂CH₂CH₂OCO₂Et | [lactone with HO(CH₂)₃ chain, Me₃Si, Ph] | 70 |
| 9-15 | Et—≡—CH₂CH₂CH₂OCO₂Et | [lactone with HO(CH₂)₃ chain, Et, Ph] | 74 |
| 9-16 | Me₃Si—≡—(CH₂)₄OCO₂Et | [lactone with HO(CH₂)₄ chain, Me₃Si, Ph] | 69 |

Reaction Product in Example 9-11

$^1$H-NMR, δ: 0.04 (s, 9H) 2.77 (t, J=5.8 Hz, 2H) 3.87 (t, J=5.8 Hz, 2H) 5.88 (s, 1H) 7.17 (m, 2H) 7.36 (m, 3H)

$^{13}$C-NMR, δ: −1.09, 29.87, 61.12, 87.65, 128.00, 128.81, 129.52, 134.81, 138.44, 164.98, 175.10

Reaction Product in Example 9-12

$^1$H-NMR, δ: 0.02 (s, 9H) 1.01 (t, J=6.0 Hz, 3H) 1.58 (m, 2H) 2.56 (d/d, J=11.7, 6.6 Hz, 1H) 2.70 (d, J=11.7 Hz, 1H) 2.75 (br s, OH) 3.86 (m, 1H) 5.88 (s, 1H) 7.20 (m, 2H) 7.36 (m, 3H)

$^{13}$C-NMR, δ: −1.09, 10.00, 30.89, 34.04, 71.76, 87.78, 128.04, 128.82, 129.51, 134.89, 138.70, 164.83, 175.30

Reaction Product in Example 9-13

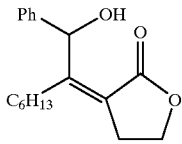

$^1$H-NMR, δ: 0.88 (t, J=6.8 Hz, 3H) 1.23 (m, 6H) 1.42 (m, 2H) 2.13 (t, J=7.5 Hz, 2H) 2.96 (m, 2H) 4.13 (d, J=6.0 Hz, OH) 4.40 (t, J=7.5 Hz, 2H) 6.43 (d, J=6.0 Hz, 1H) 7.20–7.50 (m, 5H)

$^{13}$C-NMR, δ: 13.94, 22.41, 27.71, 27.77, 29.69, 31.31, 32.99, 65.45, 71.22, 120.78, 126.11, 127.38, 128.23, 141.65, 159.36, 171.32

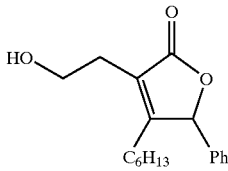

$^1$H-NMR, δ: 0.88 (t, J=6.8 Hz, 3H) 1.23 (m, 6H) 1.40 (m, 2H) 2.00 (m, 1H) 2.39 (m, 1H) 2.62 (t, J=6.0 Hz, 2H) 3.86 (t, J=6.0 Hz, 2H) 5.75 (s, 1H) 7.21 (m, 2H) 7.40 (m, 3H)

Reaction Product in Example 9-14

$^1$H-NMR, δ: 0.01 (s, 9H) 1.84 (t/t, J=7.5, 6.0 Hz, 2H) 2.57 (t, J=7.5 Hz, 2H) 2.70 (br S, OH) 3.69 (t, J=6.0 Hz, 2H) 5.81 (s, 1H) 7.14 (m, 2H) 7.33 (m, 3H)

$^{13}$C-NMR, δ: −1.19, 22.21, 32.23, 61.42, 87.21, 127..88, 128.74, 129.41, 134.98, 140.94, 163.18, 175.00

Reaction Product in Example 9-15

$^1$H-NMR, δ: 0.98 (t, J=7.8 Hz, 3H) 1.81 (t/t, J=7.5, 6.0 Hz, 2H) 2.02 (d/q, J=15.6, 7.8 Hz, 1H) 2.45 (d/q, J=15.6, 7.8 Hz, 1H) 2.47 (t, J=7.5 Hz, 2H) 2.78 (br s, OH) 3.67 (t, J=6.0 Hz, 2H) 5.75 (s, 1H) 7.20 (m, 2H) 7.38 (m, 3H)

$^{13}$C-NMR, δ: 12.31, 19.43, 19.72, 31.13, 61.16, 83.86, 126.07, 126.84, 128.86, 129.22, 134.62, 165.41, 175.00

Reaction Product in Example 9-16

$^1$H-NMR, δ: 0.06 (s, 9H) 1.71 (m, 4H) 1.89 (br s, OH) 2.52 (m, 2H) 3.76 (m, 2H) 5.82 (s, 1H) 7.17 (m, 2H) 7.38 (m, 3H)

$^{13}$C-NMR, δ: −1.09, 25.50, 25.94, 32.53, 62.33, 86.94, 127.92, 128.77, 129.42, 135.21, 141.36, 162.10, 174.50

EXAMPLE 10-1

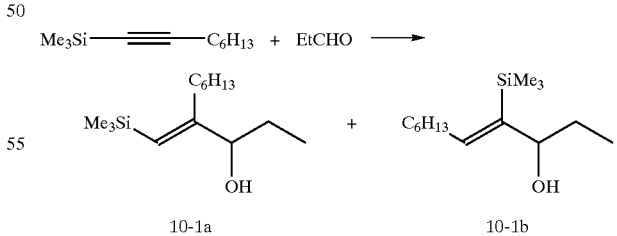

In 10 ml of ether were dissolved 0.75 ml (1.5 mmol) of trimethoxychlorotitanium (as 2M ether solution) and 0.219 ml (1.2 mmol) of 1-trimethylsilyl-1-octyne. To the solution (cooled to −78° C.) was added dropwise 1.97 ml of 1.52M ether solution containing 3 mmol of isopropylmagnesium bromide. The reaction liquid was heated to −30° C. and stirred for 5 hours. The reaction liquid was cooled again to −78° C. and given 0.066 ml (0.9 mmol) of propanal, followed by stirring for 1 hour. The reaction liquid was stirred with 20 ml of 1N hydrochloric acid at room temperature for 30 minutes. After extraction with 30 ml of ether, the organic layer was dried with anhydrous magnesium sulfate and freed of solvent by vacuum distillation. The residues were purified by silica gel chromatography. Thus there was obtained a mixture of adducts (10-1a+10-1b) in a yield of 35%.

This mixture was dissolved in 1 ml of tetrahydrofuran, and the solution was stirred together with a catalytic amount of potassium hydride at 0° C. for 1 hour. The solution was given 3 ml of aqueous solution of ammonium chloride and extracted with ether. The organic layer was dried with anhydrous magnesium sulfate and freed of solvent by vacuum distillation. The residues were purified by silica gel chromatography. Thus there was isolated 10-1a. It was found to have an optical rotation $[\alpha]_D = 1.7°$ and an optical purity of 20% ee (by $^1$H-NMR of its MTPA ester).

EXAMPLES 10-2 TO 10-6

The procedure of Example 10-1 was repeated except that the trimethoxychlorotitanium and propanal were replaced by those shown in Tables 18 and 19. There were obtained mixtures of corresponding adducts whose ratio, yield, optical rotation, and optical purity are shown in Tables 18 and 19.

TABLE 18

| Example | Titanium compound | Aldehyde | Reaction product (ratio) a | b | Yields of mixture (%) | Reaction product a Optical rotation $([\alpha]_a)$ | Optical purity (% ee) |
|---|---|---|---|---|---|---|---|
| 10-1 | ClTi(O-menthyl)₃ | EtCHO | (structure a) 77 | (structure b) 23 | 35 | 1.7 | 20 |
| 10-2 | ClTi(O-menthyl)₃ | iBuCHO | (structure a) 80 | (structure b) 20 | 26 | 1.0 | 12 |
| 10-3 | Ti(TADDOL-Ph)₂ | EtCHO | (structure a) 1 | (structure b) 1 | 31 | −3.2 | 62 |

TABLE 19

| Example | Titanium compound | Aldehyde | Reaction product (ratio) a | b | Yields of mixture (%) | Reaction product a Optical rotation $([\alpha]_a)$ | Optical purity (% ee) |
|---|---|---|---|---|---|---|---|
| 10-4 | Ti(TADDOL-Me)₂ | EtCHO | (structure a) 84 | (structure b) 16 | 8 | — | — |

TABLE 19-continued

| | | | Reaction product (ratio) | | Yields of mixture (%) | Reaction product a Optical rotation ([α]ₐ) | Reaction product a Optical purity (% ee) |
|---|---|---|---|---|---|---|---|
| Example | Titanium compound | Aldehyde | a | b | | | |
| 10-5 | Ti(...)₂ (pinacolate) | CyCHO | TMS/nC₆H₁₃ alcohol (81) | nC₆H₁₃/TMS alcohol (19) | 21 | — | 62 |
| 10-6 | ClTi(Menthol(+)) | EtCHO | TMS/nC₆H₁₃ alcohol with Et (64) | nC₆H₁₃/TMS alcohol with Et (26) | 9 | — | — |
| | | iBuCHO | TMS/nC₆H₁₃ alcohol with iBu (80) | nC₆H₁₃/TMS alcohol with iBu (20) | 15 | 23 | 14 |

Reaction Product in Example 10-1

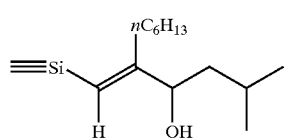

a

¹H-NMR, δ: 5.45 (s, 1H) 3.79 (t, J=4.8 Hz, 1H) 2.12–2.25 (m, 1H) 1.92–2.05 (m, 1H) 1.72–1.88 (m, 1H) 1.55–1.20 (m, 11H) 1.05–0.80 (m, 9H) 0.11 (s, 9H)

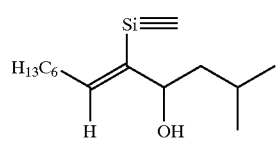

b

¹H-NMR, δ: 5.58–5.30 (m, 2H) 3.68 (t, J=7.5 Hz, 1H) 2.10–1.95 (m, 2H) 1.70–1.50 (m, 1H) 1.45–1.20 (m, 10H) 1.00–0.80 (m, 9H) 0.08 (s, 9H)

EXAMPLES 11-1 TO 11-4

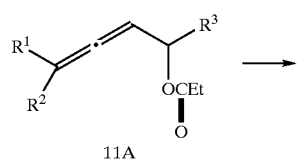

11A

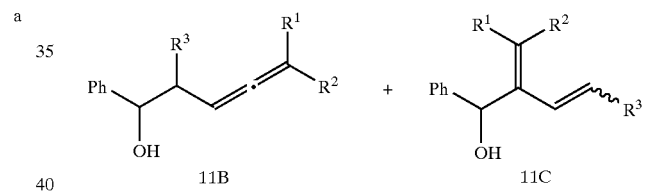

To an ethyl ether solution (10 ml) containing allenyl alcohol derivative 11A (1.0 mmol) and tetraisopropoxytitanium (0.296 ml, 1.0 mmol) was added isopropylmagnesium bromide (2.0 mmol) in ethyl ether solution at −60° C. The reaction liquid was stirred at −50° C. to −40° C. for 1.5 hours. The reaction liquid was given benzaldehyde (74 mg, 0.7 mmol) at 40° C. and then heated to room temperature over 1 hour. After mixing with 5 ml of 3N hydrochloric acid, the reaction liquid was separated into layers. The organic layer was dried with anhydrous magnesium sulfate and freed of solvent by vacuum distillation. The residues were purified by silica gel chromatography. Thus there were obtained reaction products in allene form 11B and diene form 11C in yields as shown in Table 20.

TABLE 20

| | 11A | | | Yields (%) | | |
|---|---|---|---|---|---|---|
| Example | $R^1$ | $R^2$ | $R^3$ | 11B | 11C | Recovered 11A |
| 11-1 | H | H | H | 22 | 22 | 40 |
| 11-2 | Et | H | H | 30 | 40 (E/Z = 1/3) | 15 |

TABLE 20-continued

| | 11A | | | Yields (%) | | |
|---|---|---|---|---|---|---|
| Example | R¹ | R² | R³ | 11B | 11C | Recovered 11A |
| 11-3 | H | H | Et | 28 | 41 (E only) | 13 |
| 11-4 | —(C₂H)₃— | | H | 18 | 58 | 28 |

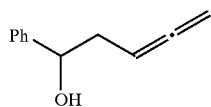

¹H-NMR, δ: 2.40–2.51 (m, 2H) 4.66–4.80 (m, 2H) 4.75 (t, J=6.3 Hz, 1H) 7.22–7.43 (m, 5H)

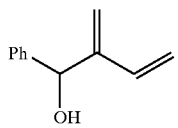

¹H-NMR, δ: 5.04 (d, J=11.3 Hz, 1H) 5.21 (d, J=17.9 Hz, 1H) 5.33 (br s, 1H) 5.40 (d, J=1.2 Hz, 1H) 5.46 (br s, 1H) 6.31 (dd, J=11.3, 17.9 Hz, 1H) 7.22–7.43 (m, 5H)

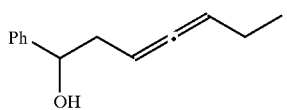

¹H-NMR, δ: 0.96 (t, J=7.9 Hz, 3H) 1.89–2.08 (m, 2H) 2.39–2.49 (m, 2H) 4.74 (t, J=6.4 Hz, 1H) 5.05–5.20 (m, 2H) 7.15–7.42 (m, 5H)

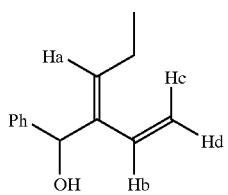

¹H-NMR, δ: 0.92–1.02 (m, 3H) 1.88–2.08 (m, 2H) (Hd) 5.09 (d, J=12.5 Hz, 1H) (Hc) 5.17 (d, J=18.4 Hz, 1H) 5.47 (br s, 1H) (Ha) 5.79 (t, J=7.5 Hz, 1H) (Hb) 6.53 (dd, J=12.5, 18.4 Hz, 1H) 7.15–7.42 (m, 5H)

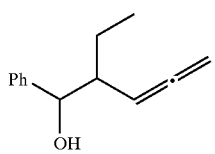

¹H-NMR, δ: 0.94 (t, J=7.2 Hz, 3H) 1.55–2.25 (m, 3H) 4.63 (d, J=9.8 Hz, 1H) 4.65–4.80 (m, 2H) 4.93–5.03 (m, 1H) 7.15–7.43 (m, 5H)

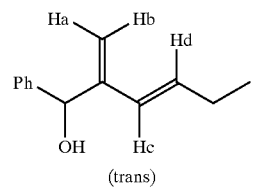

¹H-NMR, δ: 0.86 (t, J=6.4 Hz, 3H) 1.95–2.08 (m, 2H) (Ha, Hb) 5.18 (br s, 1H), 5.22 (br s, 1H), 5.40 (br s, 1H) (Hd) 5.76 (dt, J=16.3, 6.8 Hz, 1H) (Hc) 5.97 (d, J=16.3 Hz, 1H) 7.15–7.43 (m, 5H)

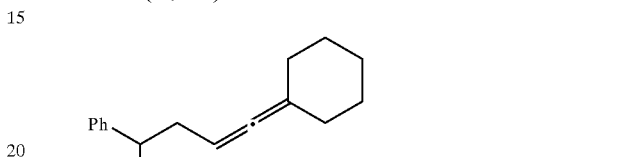

¹H-NMR, δ: 1.22–1.79 (m, 10H) 1.81–1.95 (m, 2H) 4.72 (t, J=6.8 Hz, 1H) 4.91–4.99 (m, 1H) 7.15–7.42 (m, 1H)

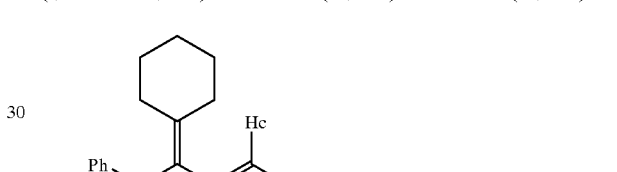

¹H-NMR, δ: 1.22–1.79 (m, 10H) (Hc) 5.02 (d, J=16.9 Hz, 1H) (Hb) 5.12 (d, J=12.0 Hz, 1H) 5.89 (br s, 1H) (Ha) 6.37 (dd, J=12.0, 16.9 Hz, 1H) 7.15–7.42 (m, 5H)

EXAMPLE 11-5

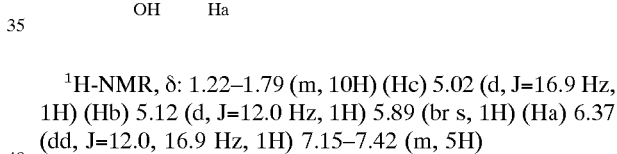

To an ethyl ether solution (12 ml) containing 3-[(ethoxycarbonyl)oxy]-1,2-nonadiene (424 mg, 2.0 mmol) and tetraisopropoxytitanium (0.89 ml, 3.0 mmol) was added at −78° C. an ethyl ether solution containing isopropylmagnesium bromide (6.0 mmol). The reaction liquid was heated to −50° C. over 30 minutes and stirred for 1 hour. The reaction liquid was given dropwise a tetrahydrofuran solution (4 ml) containing iodine (761 mg, 3.0 mmol). After heating to 0° C. over 1.5 hours, the reaction liquid was given 3N hydrochloric acid (4 ml) and separated into layers. The organic layer was washed with a saturated aqueous solution of sodium thiosulfate and a saturated aqueous solution of sodium hydrogen carbonate, dried with anhydrous magnesium sulfate, and freed of solvent by vacuum distillation. The residues were purified by silica gel chromatography. There was obtained 385 mg of (E)-2-iodo-1,3-nonadiene as an iodinated compound (yield: 77%).

EXAMPLES 11-6 TO 11-8

The procedure of Example 11-5 was repeated by using allenyl alcohols shown in Table 21. There were obtained iodinated compounds as shown in Table 21.

TABLE 21

| Example | Allenyl alcohol | Reaction product | Yields (%) |
|---|---|---|---|
| 11-5 | {C5H11, OCO2Et allenyl} | I, C5H11 diene | 77 |
| 11-6 | TMS, OCO2Et allenyl | I, TMS diene | 55 |
| 11-7 | cyclohexylidene-allenyl OCO2Et | cyclohexylidene vinyl iodide | 85 |
| 11-8 | C5H11, OCO2Et allenyl | C5H11, I diene | 78 (E/Z = 57/43) |

Reaction Product in Example 11-5
$^1$H-NMR, δ: 0.90 (t, J=6.8 Hz, 3H) 1.20–1.60 (m, 6H) 2.19 (q, J=7.1 Hz, 2H) 5.56 (d, J=14.8 Hz, 1H) 5.86 (s, 1H) 5.93 (dt, J=14.8, 7.1 Hz, 1H) 6.21 (s, 1H)
$^{13}$C-NMR, 65: 14.0, 22.5, 28.8, 31.4, 31.8, 108.6, 126.2, 131.1, 142.1

Reaction Product in Example 11-6
$^1$H-NMR, δ: 0.22 (s, 9H) 5.60 (s, 1H) 5.86 (s, 1H) 6.05 (s, 1H) 6.20 (s, 1H)

Reaction Product in Example 11-7
$^1$H-NMR, δ: 1.45–1.75 (m, 6H) 2.50–2.65 (m, 4H) 5.22 (d, J=10.4 Hz, 1H) 5.45 (d, J=15.9 Hz, 1H) 6.34 (dd, J=10.4, 15.9 Hz, 1H)
$^{13}$C-NMR, δ: 26.6, 27.7, 28.0, 32.5, 43.3, 99.2, 122.2, 134.4, 149.2

Reaction Product in Example 11-8
$^1$H-NMR, δ:
(E&Z) 0.80–1.03 (m, 3H) 1.15–1.75 (m, 6H) 2.23–2.40 (m, 2H)
(Z) 5.32 (d, J=10..4 Hz, 1H) 5.44 (d, J=15.9 Hz, 1H) 6.11 (dd, J=10.4, 15.9 Hz, 1H) 5.40 (t, J=7.8 Hz, 1H)
(E) 5.15 (d, J=10.3 Hz, 1H) 5.40 (d, J=16.2 Hz, 1H) 5.92 (t, J=6.8 Hz, 1H) 5.98 (dd, J=10.3, 16.2 Hz, 1H)

EXAMPLE 11-9

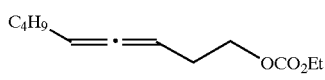

11-9S

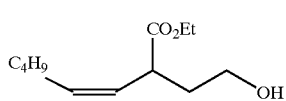

11-9P

To a diethyl ether solution (8.4 ml) containing 11-9S (179 mg, 0.843 mmol) and tetraisopropoxytitanium (335 mg, 1.18 mmol) was added at −78° C. under an argon atmosphere a diethyl ether solution containing isopropylmagnesium chloride (2.28 mmol). The reaction liquid was heated to −50° C. over 1 hour and stirred for 2 hours. After addition of water (0.3 ml), the reaction liquid was heated to room temperature and then stirred together with diethyl ether (10 ml) and sodium fluoride (300 mg) for 10 minutes. The reaction liquid was filtered through celite and freed of solvent by vacuum evaporation. The residues were purified by silica gel chromatography. Thus there was obtained 150 mg of 11-9P (yield: 83%, cis/trans=77/23).

$^1$H-NMR, δ: 0.84–0.93 (m, 3H) 1.20–1.40 (m, 7H) 1.60–1.82 (m, 2H) 1.90–2.17 (m, 3H) 3.09–3.74 (m, 3H) 4.07–4.18 (m, 2H) 5.30–5.63 (m, 2H)

EXAMPLE 11-10

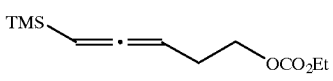

11-10S

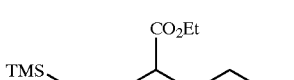

11-10P

The procedure of Example 11-9 was repeated to make 11-10S (194 mg, 0.85 mmol) into 11-10P (109 mg) (yield: 56%, cis form only).

¹H-NMR, δ: 0.16 (s, 9H) 1.26 (t, J=7.1 Hz, 3H) 1.54 (bs, 1H) 1.72–1.87 (m, 1H) 1.96–2.10 (m, 1H) 3.40 (dt, J=10.4, 7.2 Hz, 1H) 3.58–3.76 (m, 2H) 4.15 (q, J=7.1 Hz, 2H) 5.71 (d, J=13.8 Hz, 1H) 6.24 (dd, J=10.4, 13.8 Hz, 1H)

EXAMPLES 12-1 TO 12-8

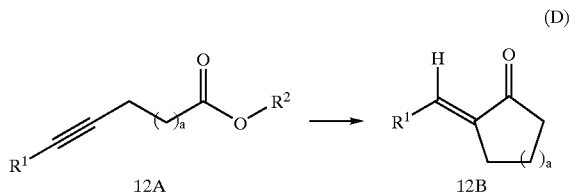

To an ethyl ether solution (10 ml) containing acetylene carboxylate ester 12A (1.0 mmol) and triisopropoxychlorotitanium (1.5 mmol) was added at −78° C. an ethyl ether solution containing isopropylmagnesium bromide (3.0 mmol). The reaction liquid was stirred at −50° C. to −45° C. for 2 hours. The reaction liquid was given 0.3 ml of a saturated aqueous solution of sodium hydrogen carbonate and heated to room temperature. The reaction liquid was stirred together with 1 g each of sodium fluoride and celite. After filtration, the filtrate was concentrated under reduced pressure and the residues were purified by silica gel chromatography. There were obtained samples of 12B (cyclized form) in respective yields shown in Table 22. (In Table 22, D denotes a deuterium atom. Termination with heavy water in place of water gives rise to products in deuterio form.)

TABLE 22

| | | | | 12B | |
|---|---|---|---|---|---|
| Example | 12A | | | Yield (%) | Deuterio form (%) |
| 12-1 | R¹ = Me₃Si | R² = Me | n = 2 | 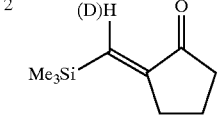 | 18~35 |
| 12-2 | Me₃Si | Et | 2 | " | 25 |
| 12-3 | Me₃Si | ⁱPr | 2 | " | 72 (98% D) |
| 12-4 | Me₃Si | ᵗBu | 2 | " | 12 |
| 12-5 | Me₃Si | ⁱPr | 3 | 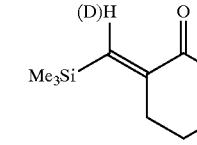 | 79 (98% D) |
| 12-6 | ᵗBu | ⁱPr | 3 | 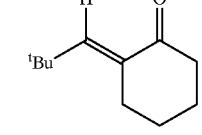 | 70 |
| 12-7 | Ph | ⁱPr | 3 | 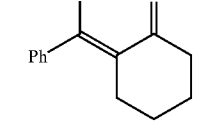 | 68 |
| 12-8 | 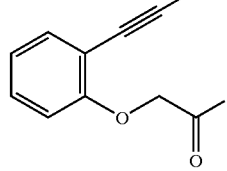 | | | 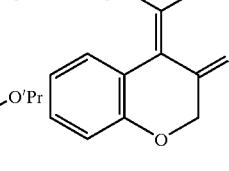 | 72 |

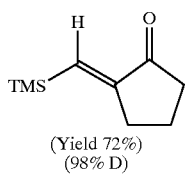

(Yield 72%)
(98% D)

¹H-NMR, δ: 0.15 (s, 9H) 1.86–2.00 (m, 2H) 2.31 (t, J=7.9 Hz, 2H) 2.68 (dt, J=2.6, 7.3 Hz, 2H) 6.65 (t, J=2.6 Hz, 1H)

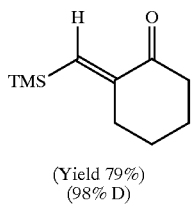

(Yield 79%)
(98% D)

¹H-NMR, δ: 0.15 (s, 9H) 1.69–1.96 (m, 4H) 2.45 (t, J=6.5 Hz, 2H) 2.62 (t, J=6.2 Hz, 2H) 6.56 (br s, 1H)
¹³C-NMR, δ: −0.7, 23.8, 24.3, 32.1, 40.4, 136.3, 151.8, 201.3

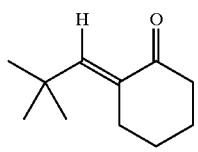

¹H-NMR, δ: 0.16 (s, 9H) 1.68–1.91 (m, 4H) 2.43 (t, J=6.7 Hz, 28) 2.67 (dt, J=2.0, 6.5 Hz, 2H) 6.57 (t, J=2.0 Hz, 1H)

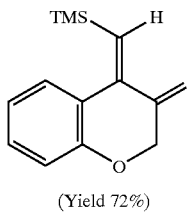

(Yield 72%)

¹H-NMR, δ: 0.21 (s, 9H) 4.55 (s, 2H) 7.00 (s, 1H) 7.02–7.12 (m, 2H) 7.31 (t, J=7.8 Hz, 1H) 7.42 (d, J=7.8 Hz, 1H)

EXAMPLE 12-9

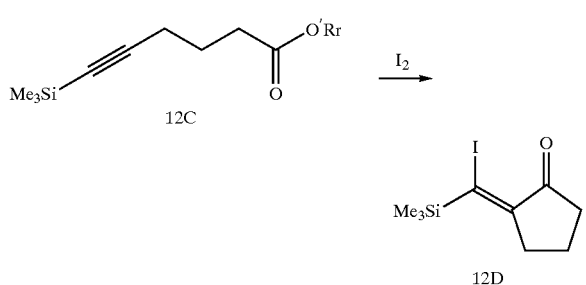

To an ethyl ether solution (10 ml) containing acetylene carboxylate ester 12C (1.0 mmol) and triisopropoxychlorotitanium (1.5 mmol) was added at −78° C. an ethyl ether solution containing isopropylmagnesium bromide (3.0 mmol). The reaction liquid was stirred at −50° C. to −45° C. for 2 hours. The reaction liquid was given an ethyl ether solution (5 ml) of iodine (3.0 mmol). The reaction liquid was heated to 0° C. over 1.5 hours. With 5 ml of 3N hydrochloric acid added, the reaction liquid was separated into layers. The organic layer was dried with anhydrous magnesium sulfate and freed of solvent by vacuum distillation. The residues were purified by silica gel chromatography. There was obtained 12D in iodated form (yield: 56%).

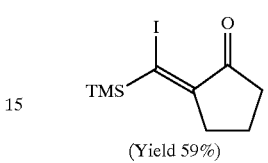

(Yield 59%)

¹H-NMR, δ: 0.32 (s, 9H) 1.70–1.86 (m, 2H) 2.41 (t, J=8.0 Hz, 2H) 2.76 (t, J=7.6 Hz, 2H)

EXAMPLE 12-10

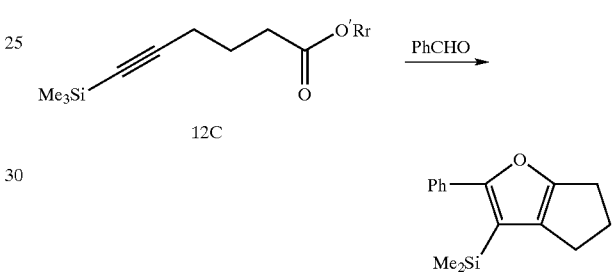

To an ethyl ether solution (10 ml) containing acetylene carboxylate ester 12C (1.0 mmol) and triisopropoxychlorotitanium (1.5 mmol) was added at −78° C. an ethyl ether solution containing isopropylmagnesium bromide (3.0 mmol). The reaction liquid was stirred at −50° C. to −45° C. for 2 hours. The reaction liquid was given benzaldehyde (1.5 mmol). The reaction liquid was heated to 0° C. over 1.5 hours. With 5 ml of 3N hydrochloric acid added, the reaction liquid was separated into layers. The organic layer was dried with anhydrous magnesium sulfate and freed of solvent by vacuum distillation. The residues were purified by silica gel chromatography. There was obtained 12E in furan form (yield: 62%).

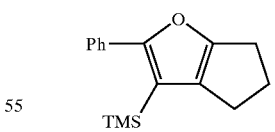

¹H-NMR, δ: 0.21 (s, 9H) 2.38–2.53 (m, 2H) 2.57–2.82 (m, 4H) 7.10–7.65 (m, 5H)

EXAMPLES 13-1 TO 13-11

To an ethyl ether solution (4.6 mmol) containing any of 11 kinds of acetylene carboxylate ester 13A (1.0 mmol) shown in Table 23 and triisopropoxychlorotitanium (2.3 mmol) was added at −78° C. an ethyl ether solution containing isopropylmagnesium bromide (4.6 mmol). The reaction liquid was stirred at −50° C. to −45° C. for 2 hours. With 5 ml of 3N hydrochloric acid added, the reaction liquid was separated into layers. The organic layer was dried with anhydrous magnesium sulfate and freed of solvent by vacuum distillation. The residues were purified by silica gel chromatography. There were obtained samples of 13B in α,β-unsaturated ketone form in respective yields as shown in Table 23. In the case where heavy water was added in place of 3N hydrochloric acid, there were obtained compounds having a deuterium atom in the same yield.

TABLE 23

| Example | 13A | 13B | Yields (%) |
|---|---|---|---|
| 13-1 | Me₃Si—≡—CH₂CH₂OAc | Me₃Si-CH=C(COCH₃)-CH₂CH₂OH | 69 |
| 13-2 | Me₃Si—≡—(CH₂)₃OAc | Me₃Si-CH=C(COCH₃)-(CH₂)₃OH | 58 |
| 13-3 | Me₃Si—≡—(CH₂)₄OAc | Me₃Si-CH=C(COCH₃)-(CH₂)₄OH | 47 |
| 13-4 | Me₃Si—≡—CH₂CH₂OC(O)Ph | Me₃Si-CH=C(COPh)-CH₂CH₂OH | 76 |
| 13-5 | Me₃Si—≡—(CH₂)₃OC(O)Ph | Me₃Si-CH=C(COPh)-(CH₂)₃OH | 77 |
| 13-6 | Me₃Si—≡—(CH₂)₃OC(O)CH=CHCH₃ | Me₃Si-CH=C(COCH=CHCH₃)-(CH₂)₃OH | 38 |
| 13-7 | Me₃Si—≡—(CH₂)₃OC(O)O$^t$Bu | Me₃Si-CH=C< cyclic hemiketal with $^t$Bu, OH / Me₃Si-CH=CH-(CH₂)₃-OC(O)O$^t$Bu | 39.5 / 23.5 |
| 13-8 | Me₃Si—≡—(CH₂)₃OC(O)CF₃ | Me₃Si-CH=C< cyclic hemiketal with CF₃, OH | 48 |
| 13-9 | Et—≡—(CH₂)₃OAc | Et-CH=C(COCH₃)-(CH₂)₃OH | 22 |

TABLE 23-continued

| Example | 13A | 13B | Yields (%) |
|---|---|---|---|
| 13-10 | 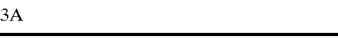 | 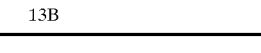 | 61 |
| 13-11 |  | 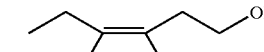 | |

Reaction Product in Example 13-1

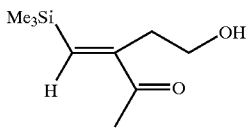

$^1$H-NMR, δ: 0.11 (s, 9H) 2.35 (s, 3H) 2.61 (t, J=6.35 Hz, 2H) 3.62 (t, J=6.32 Hz, 2H) 6.77 (s, 1H)

$^{13}$C-NMR, δ: −0.29 (3C), 25.8, 34.1, 62.8, 144.6, 153.3, 202.0

IR: 3430, 2950, 1670, 1600, 1360, 1250, 850 (cm$^{-1}$)

Reaction Product in Example 13-2

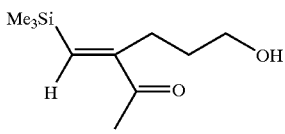

$^1$H-NMR, δ: 0.20 (s, 9H) 1.57–1.62 (m, 2H) 2.34 (s, 3H) 2.42 (t, J=7.57 Hz, 2H) 3.56 (t, J=6.21 Hz, 2H) 6.69 (s, 1H)

$^{13}$C-NMR, δ: −0.36 (3C), 259.7, 26.4, 33.2, 62.0, 142.7, 155.9, 201.0

IR: 3400, 2930, 1660, 1580, 1360, 1240, 840 (cm$^{-1}$)

Reaction Product in Example 13-3

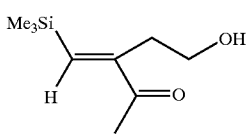

$^1$H-NMR, δ: 0.16 (s, 9H) 1.30–1.41 (m, 2H) 1.54 (tt, J=6.90 Hz, 2H) 2.29 (s, 3H) 2.31 (t, J=7.58 Hz, 2H) 3.60 (t, J=6.53 Hz, 2H) 6.59 (s, 1H)

$^{13}$C-NMR, δ: −0.39 (3C), 25.8, 26.1, 30.3, 32.6, 62.6, 141.4, 156.4, 200.6

Reaction Product in Example 13-4

$^1$H-NMR, δ: 0.21 (s, 9H) 2.80 (t, J=6.08 Hz, 2H) 3.77 (t, J=6.05 Hz, 2H) 6.30 (s, 1H)

$^{13}$C-NMR, δ: −0.15 (3C), 35.6, 62.7, 128.2, 129.9, 132.4, 137.3, 144.3, 152.5, 200.0

Reaction Product in Example 13-5

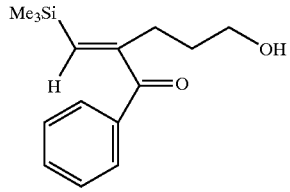

$^1$H-NMR, δ: 0.19 (s, 9H) 1.65–1.75 (m, 2H) 2.65 (t, J=7.67 Hz, 2H) 3.62 (t, J=6.32 Hz, 2H) 6.18 (s, 1H) 7.38–7.44 (m, 2H) 7.48–7.54 (m, 1H) 7.69–7.72 (m, 2H)

$^{13}$C-NMR, δ: −0.29 (3C), 28.2, 32.4, 62.1, 128.1, 129.6, 132.1, 137.6, 142.2, 154.9, 199.3

IR: 3380, 2920, 1650, 1600, 1450, 1240, 1060, 850 (cm$^{-1}$)

Reaction Product in Example 13-6

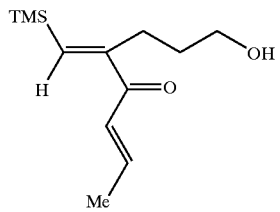

¹H-NMR, δ: 0.21 (s, ⁹H) 1.59–1.68 (m, 2H) 1.92 (dd, J=6.44, 1.5 Hz, 3H) 2.52 (t, J=7.41 Hz, 2H) 3.57 (t, J=6.18 Hz, 2H) 6.55 (s, 1H) 6.69 (dd, J=15.2, 1.5 Hz, 1H) 6.82–6.54 (m, 1H)

¹³C-NMR, δ: –0.25 (3C), 18.4, 27.1, 32.9, 62.0, 127.3, 140.3, 143.8, 156.4, 193.4

Reaction Product in Example 13-7-1

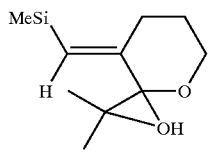

¹H-NMR, δ: 0.17 (s, 9H) 1.22 (s, 9H) 1.57–1.63 (m, 2H) 2.42 (t, J=7.82 Hz, 2H) 3.61 (t, J=6.24 Hz, 2H) 5.76 (s, 1H)

¹³C-NMR, δ: –0.02 (3C), 28.2 (3C), 30.3, 32.4, 43.6 (1C), 62.3, 131.2, 156.7, 213.8

IR: 3430, 2960, 1680, 1600, 1260, 1140, 860 (cm⁻¹)

Reaction Product in Example 13-7-2

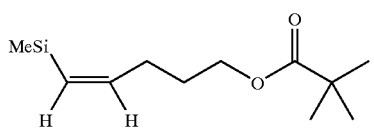

¹H-NMR, δ: 0.11 (s, 9H) 1.20 (s, 9H) 1.62–1.76 (m, 2H) 2.20 (dt, J=6.51, 7.47 Hz, 2H) 4.06 (t, J=6.50 Hz, 2H) 5.52 (d, J=1.40 Hz, 1H) 6.28 (dt, J=14.1, 7.2 Hz, 1H)

¹³C-NMR, δ: 0.15 (3C), 27.2 (3C), 28.9, 30.0, 38.7 (1C), 64.0, 130.0, 147.5, 178.5

IR: 2940, 1720, 1600, 1480, 1280, 1240, 1150, 840 (cm⁻¹)

Reaction Product in Example 13-8

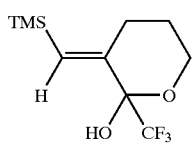

¹H-NMR, δ: 0.16 (s, 9H) 1.65–1.78 (m, 1H) 1.94–2.08 (m, 1H) 2.55–2.63 (m, 1H) 2.94 (s, 1H) 6.05 (s, 1H)

¹³C-NMR, δ: 0.28, 24.9, 26.4, 61.2, 120.7, 124.6, 131.3, 146.9

Reaction Product in Example 13-10

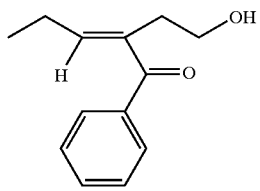

¹H-NMR, δ: 1.06 (t, J=7.56 Hz, 3H) 2.34 (dt, J=15.2, 7.5 Hz, 2H) 2.72 (t, J=6.08 Hz, 2H) 3.76 (t, J=6.06 Hz, 2H) 6.35 (t, J=7.41 Hz, 1H)

¹³C-NMR, δ: 13.3, 22.3, 30.6, 62.3, 128.1, 129.6, 131.9, 137.5, 138.2, 150.0, 200.2

EXAMPLE 13-12

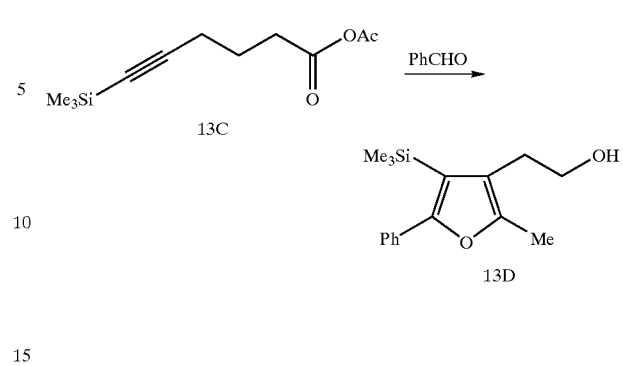

To an ethyl ether solution (10 ml) containing acetylene alcohol ester 13C (1.0 mmol) and triisopropoxychlorotitanium (2.3 mmol) was added at –78° C. an ethyl ether solution containing isopropylmagnesium bromide (4.6 mmol). The reaction liquid was stirred at –50° C. to –45° C. for 1 hour. The reaction liquid was given 74 mg (0.7 mmol) of benzaldehyde at –40° C. and heated to 0° C. over 1 hour. With 5 ml of 3N hydrochloric acid added, the reaction liquid was separated into layers. The organic layer was dried with anhydrous magnesium sulfate and freed of solvent by vacuum distillation. The residues were purified by silica gel chromatography. There was obtained 13D in furan form (yield: 62%).

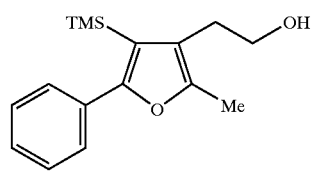

¹H-NMR, δ: 0.16 (s,9H) 2.31 (s, 3H) 2.74 (t, J=6.98 Hz, 2H) 3.76 (t, J=6.89 Hz, 2H) 7.34–7.41 (m, 3H) 7.44–7.47 (m, 2H)

¹³C-NMR, δ: 1.11(3C), 11.5, 29.0, 63.1, 114.9, 120.5, 127.8(2C), 128.1, 129.1(2C), 133.4, 148.9, 158.0

EXAMPLES 14-1 TO 14-9

To an ethyl ether solution (7 ml) containing any of 9 kinds of olefin ester 14A (1.0 mmol) shown in Table 24 and tetraisopropoxytitanium (2.0 mmol) was added at –50° C. an ethyl ether solution containing isopropylmagnesium bromide (4.0 mmol). The reaction liquid was stirred at –45° C. to –40° C. for 2 hours. The reaction liquid was heated to 0° C. and stirred for 2 hours. With 5 ml of 3N hydrochloric acid added, the reaction liquid was separated into layers. The organic layer was dried with anhydrous magnesium sulfate and freed of solvent by vacuum distillation. The residues were purified by silica gel chromatography. There were obtained samples of 14B in cyclopropane form in respective yields as shown in Table 24.

TABLE 24
| Example | 14A | 14B | Yields (%) | Z/E |
|---|---|---|---|---|
| 14-1 | 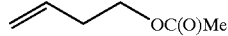 | 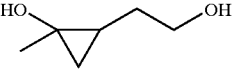 | 93 | 58:42 |
| 14-2 | 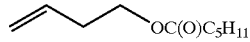 | 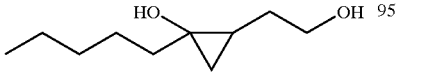 | 95 | 88:12 |
| 14-3 | 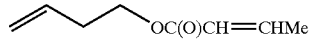 | 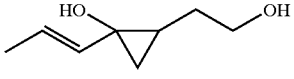 | 78 | 93:7 |
| 14-4 | 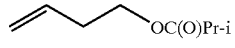 | 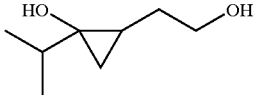 | 88 | 88:12 |
| 14-5 | 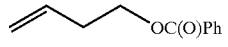 |  | 85 | >97:3 |
| 14-6 | 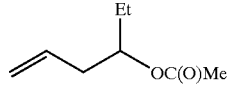 | 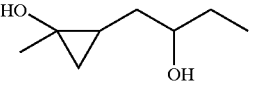 | 33 (70) | 41:59 (95:5) |
| 14-7 | 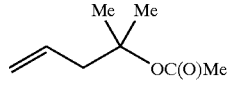 | 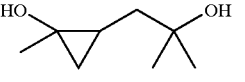 | 28 (78) | 47:53 (91:9) |
| 14-8 | 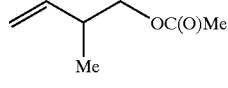 | 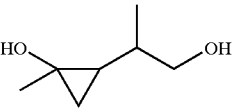 | 74 | >97:3 |
| 14-9 | 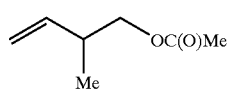 | 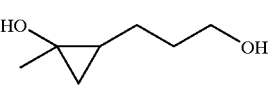 | 25 | 73:27 |
*Values in parentheses are those which were obtained in the case where the reaction liquid was stirred at 0° C., heated to 20° C., and stirred again for 3.5 hours.
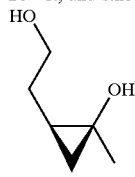
$^{1}$H-NMR, δ: 0.41 (m, 1H) 0.65 (m, 2H) 1.40 (s, 3H) 1.57 (m, 1H) 2.00 (m, 1H) 3.65 (m, 1H) 3.80 (m, 1H)
$^{13}$C-NMR, δ: 19.99, 23.09, 25.86, 31.19, 54.07, 62.43
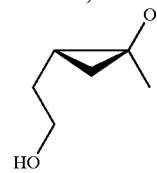
$^{1}$H-NMR, δ: 0.13 (d/d, J=6.0, 6.0 Hz, 1H) 0.89 (d/d, J=10.2, 6.0 Hz, 1H) 1.05 (m, 1H) 1.43 (s, 3H) 1.51 (d/t, J=6.2, 6.2 Hz, 2H) 2.90 (br s, 2H) 3.70 (t, J=6.2 Hz, 2H)
$^{13}$C-NMR, δ: 19.62, 20.62, 22.09, 32.74, 54.91, 62.39
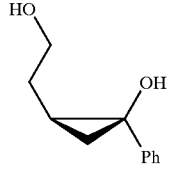
$^{1}$H-NMR, δ: 0.93 (d/d, J=5.8, 5.8 Hz, 1H) 1.18 (m, 1H) 1.27 (d/d, J=10.2, 5.8 Hz, 1H) 1.72 (m, 1H) 2.12 (m, 1H) 3.64 (m, 1H) 3.80 (m, 1H) 7.15–7.35 (m, 5H)
$^{13}$C-NMR, δ: 23.31, 31.18, 27.57, 57.83, 62.45, 124.05, 125.91, 128.15, 145.82

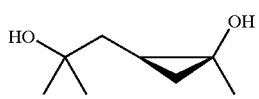

¹H-NMR, δ: 0.43 (d/d, J=5.8, 5.8 Hz, 1H) 0.65 (d/d, J=9.6, 5.8 Hz, 1H) 0.74 (m, 1H) 1.28 (s, 3H) 1.33 (s, 3H) 1.44 (s, 3H) 1.52 (d/d, J=15.0, 10.3 Hz, 1H) 1.92 (d/d, J=15.0, 5.1 Hz, 1H)

¹³C-NMR, δ: 20.57, 20.93, 26.02, 28.16, 31.32, 42.00, 54.14, 71.37

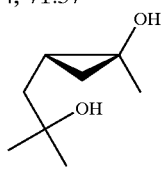

¹H-NMR, δ: 0.17 (d/d, J=6.0, 6.0 Hz, 1H) 0.97 (d/d, J=10.2, 6.0 Hz, 1H) 1.10 (m, 1H) 1.2–1.35 (s, 7H) 1.42 (s, 3H) 1.65 (d/d, J=13.8, 5.7 Hz, 1H) 1.8–2.5 (m, 2H)

¹³C-NMR, δ: 20.48, 20.90, 21.31, 29.50, 29.13, 43.36, 54.82, 71.33

EXAMPLES 15-1 TO 15-8

To an ethyl ether Solution (7 ml) containing any of 8 kinds of olefin alcohol ester 15A (1.0 mmol) shown in Table 25 and tetraisopropoxytitanium (1.3 mmol) was added at −50° C. an ethyl ether solution containing isopropylmagnesium chloride (2.6 mmol). The reaction liquid was stirred at −50° C. to −40° C. for 1 hour. With 5 ml of 3N hydrochloric acid added, the reaction liquid was separated into layers. The organic layer was dried with anhydrous magnesium sulfate and freed of solvent by vacuum distillation. The residues were purified by silica gel chromatography. Thus there were obtained samples of 15B in lactone form or ring-opened form in respective yields as shown in Table 25.

TABLE 25

| Example | 15A | 15B | Yields (%) |
|---|---|---|---|
| 15-1 | | | 92 |
| 15-2 | | | 92 |
| 15-3 | | | 89 |
| 15-4 | | | 86 |
| 15-5 | | | 79 |
| 15-6 | | | 30 |

TABLE 25-continued

| Example | 15A | 15B | Yields (%) |
|---|---|---|---|
| 15-7 | (benzaldehyde with cyclic carbonate, OEt) | (phenol with CH(CH3)CO2Et, OH) | 89 |
| 15-8 | (allyl dimethyl carbinol carbonate OEt) | (trimethyl butyrolactone) | 46 |

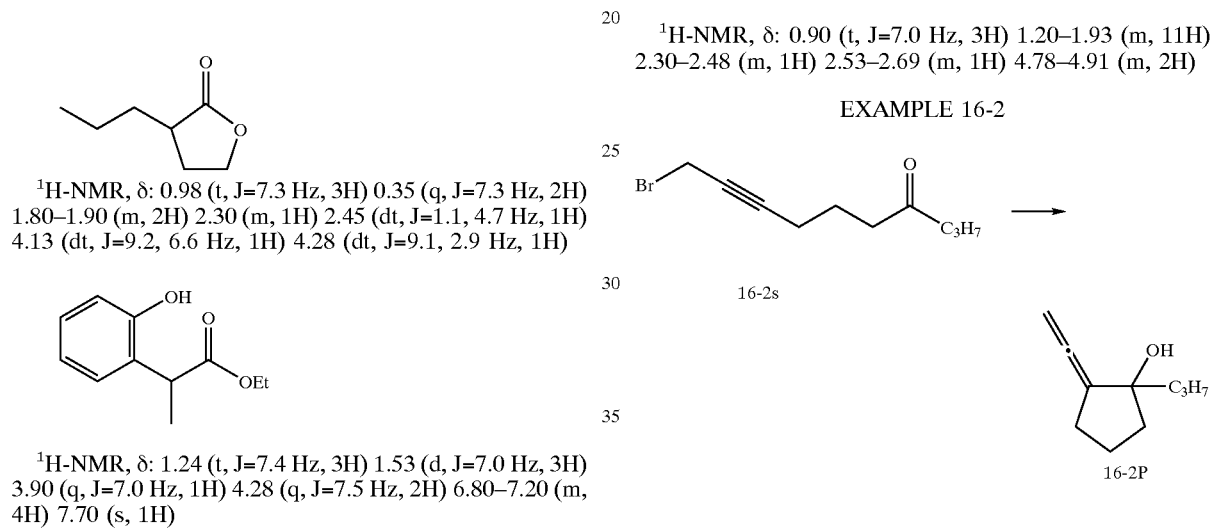

$^1$H-NMR, δ: 0.98 (t, J=7.3 Hz, 3H) 0.35 (q, J=7.3 Hz, 2H) 1.80–1.90 (m, 2H) 2.30 (m, 1H) 2.45 (dt, J=1.1, 4.7 Hz, 1H) 4.13 (dt, J=9.2, 6.6 Hz, 1H) 4.28 (dt, J=9.1, 2.9 Hz, 1H)

$^1$H-NMR, δ: 1.24 (t, J=7.4 Hz, 3H) 1.53 (d, J=7.0 Hz, 3H) 3.90 (q, J=7.0 Hz, 1H) 4.28 (q, J=7.5 Hz, 2H) 6.80–7.20 (m, 4H) 7.70 (s, 1H)

EXAMPLE 16-1

16-1S → 16-1P

To a diethyl ether solution (5.6 ml) containing chlorotriisopropoxytitanium (293 mg, 1.13 mmol) was added at −78° C. a diethyl ether solution (1.67 ml) containing isopropylmagnesium bromide (2.17 mmol). The reaction liquid was stirred for 1 hour. The reaction liquid was given a diethyl ether (2 ml) containing 16-1S (187 mg, 0.763 mmol) and then heated to room temperature over 3 hours. The reaction liquid was given a saturated aqueous solution of sodium hydrogen carbonate at 0° C. and then stirred together with sodium fluoride and celite at room temperature. After filtration (to remove celite), the filtrate was concentrated under reduced pressure. The residues were purified by silica gel chromatography. Thus there was obtained 82 mg of 16-1P in cyclized form (yields: 65%)

$^1$H-NMR, δ: 0.90 (t, J=7.0 Hz, 3H) 1.20–1.93 (m, 11H) 2.30–2.48 (m, 1H) 2.53–2.69 (m, 1H) 4.78–4.91 (m, 2H)

EXAMPLE 16-2

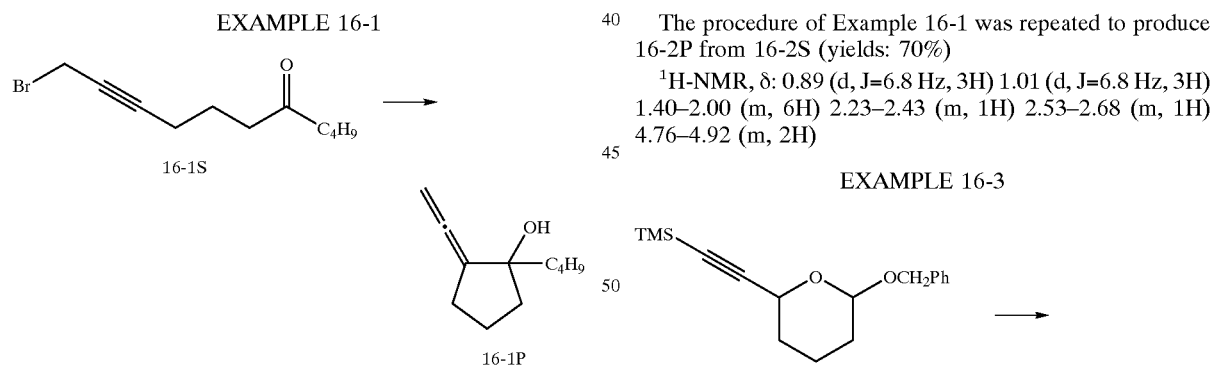

The procedure of Example 16-1 was repeated to produce 16-2P from 16-2S (yields: 70%)

$^1$H-NMR, δ: 0.89 (d, J=6.8 Hz, 3H) 1.01 (d, J=6.8 Hz, 3H) 1.40–2.00 (m, 6H) 2.23–2.43 (m, 1H) 2.53–2.68 (m, 1H) 4.76–4.92 (m, 2H)

EXAMPLE 16-3

16-3S → 16-3P

To a diethyl ether solution (3.6 ml) containing 16-3S (103 mg, 0.356 mmol) and tetraisopropoxytitanium (142 mg, 0.498 mmol) was added at −50° C. a diethyl ether solution (0.55 ml) containing isopropylmagnesium bromide (0.962 mmol). The reaction liquid was stirred for 1 hour and then heated to room temperature over 1 hour. With 1N hydrochloric acid added, the reaction liquid was separated into layers. The organic layer was dried with anhydrous magnesium sulfate and freed of organic solvent by vacuum distillation. The residues were purified by silica gal chromatography. Thus there were obtained 51 mg of 16-3P in cis form (yields: 79%) and 6.5 mg of 16-3P in trans form (yields: 10%).

EXAMPLES 16-4 AND 16-5

The procedure of Example 16-3 was repeated to give cyclized products except that the starting materials were changed as shown in Table 26.

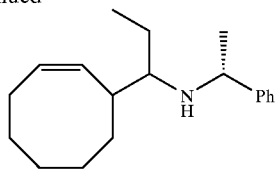

To an ethyl ether solution (8 ml) containing tetraisopropoxytitanium (0.37 ml, 1.28 mmol) and 3-bromocyclooctene (219 mg, 1.16 mmol) was added dropwise at −50° C. under an argon atmosphere a 1.53M ethyl ether solution (1.67 ml) containing isopropylmagnesium bromide (2.56 mmol). The reaction liquid was stirred at −50° C. to −40° C. for 1.5 hours. The reaction liquid was given N-propylidene-((R)-1-

TABLE 26

| Example | Starting material | Reaction product | Yields (%) |
|---|---|---|---|
| 16-3 | TMS-alkyne-tetrahydropyran-OCH₂Ph | TMS-alkyne-cyclopentane-OH | cis-form 79% trans-form 10% |
| 16-4 | Ph-alkyne-tetrahydropyran(Me)-OCH₂Ph | Ph-alkyne-cyclopentane(CH₃)-OH | cis-form 62% |
| 16-5 | C₆H₁₃-alkyne-tetrahydropyran(Me)-OCH₂Ph | C₆H₁₃-alkyne-cyclopentane(Me)-OH | cis-form 53% |

Reaction Product in Example 16-3

¹H-NMR, δ: (cis-form) 0.15 (s, 9H) 1.45–2.20 (m, 7H) 2.61–2.71 (m, 1H) 4.10–4.16 (m, 1H)

(trans-form) 0.15 (s, 9H) 1.50–2.15 (m, 7H) 2.54–2.63 (m, 1H) 4.15–4.24 (m, 1H)

Reaction Product in Example 16-4

¹H-NMR, δ: 1.41 (s, 38) 1.56–2.18 (m, 7H) 2.70 (dd, J=8.2, 9.9 Hz, 1H) 7.27–7.47 (m, 5H)

Reaction Product in Example 16-5

¹H-NMR, δ: 0.88 (t, J=6.8 Hz, 3H) 1.17 (s, 3H) 1.20–2.13 (m, 15H) 2.19 (t, J=7.1 Hz, 2H) 3.58–3.68 (m, 1H)

phenylethyl)amine (130 mg, 0.81 mmol) at −40° C. and then stirred for 5 hours. With water added, the reaction liquid was separated into layers. The organic layer was dried with anhydrous magnesium sulfate and freed of solvent by vacuum distillation. The residues were purified by silica gal chromatography. Thus there were obtained 147 mg of adduct (yields: 67%), which has a diastereomer ratio of 92:8.

¹H-NMR, δ: 0.77 (t, J=7.4 Hz, 3H) 1.19–1.76 (m, 14H) 1.98–2.10 (m, 1H) 2.12–2.29 (m, 1H) 2.32–2.40 (m, 1H) 2.54–2.69 (m, 1H) 3.80 (q, J=6.5 Hz, 1H) 5.38 (dd, J₁=J₂= 9.8 Hz, 1H) 5.65–5.77 (m, 1H) 7.16–7.39 (m, 5H)

EXAMPLE 17-1

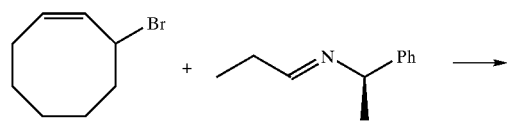

EXAMPLE 17-2

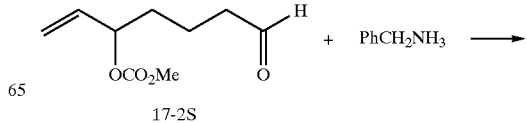

17-2S

-continued

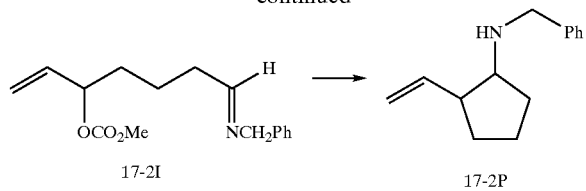

17-2I → 17-2P

To a tetrahydrofuran solution (1 ml) containing benzylamine (55 mg, 0.5 mmol) were added at 0° C. anhydrous magnesium sulfate, aldehyde 17-2S (93 mg, 0.5 mmol), and triethylamine (0.07 mmol, 0.5 mmol). The reaction liquid was stirred for 2 hours. With anhydrous pentane added, the reaction liquid was filtered off to separate solids, and the filtrate was concentrated. Thus there was obtained imine 17-2I in quantitative yields.

To a diethyl ether solution (7 ml) containing this imine and tetraisopropoxytitanium (0.224 ml, 0.75 mmol) was added at −78° C. a diethyl ether solution (0.857 ml) containing isopropylmagnesium bromide (2.25 mmol). The reaction liquid was heated to −50° C. and stirred for 30 minutes. The reaction liquid was heated to room temperature over 3 hours. With water added, the reaction liquid was separated into layers. The organic layer was dried with anhydrous magnesium sulfate and freed of organic solvent. The residues were purified by silica gel chromatography. Thus there was obtained 100 mg of amine 17-2P (yields: 57%).

EXAMPLES 17-3 TO 17-11

The procedure of Example 17-2 was repeated to produce amines from aldehyde and amine (through imine) as shown in Table 27.

TABLE 27

| Example | Aldehyde | Amine | Amine produced P | Yields (%) (diastereomer ratio) |
|---|---|---|---|---|
| 17-2 | (aldehyde structure with OCO₂Me and CHO, vinyl) | PhCH₂NH₂ | (vinyl cyclopentane with NBn) | 57 |
| 17-3 | (aldehyde structure with OCO₂Me, vinyl) | PhCH₂NH₂ | (vinyl cyclohexane with NBn) | 38 |
| 17-4 | (benzaldehyde with CH₂CH(OCO₂Me)CH=CH₂) | PhCH₂NH₂ | (indane with NBn and vinyl) | 38 |
| 17-5 | (MeO₂CO-CH₂-C≡C-CH₂CH₂CHO) | PhCH₂NH₂ | (cyclopentane with N-CH₂Ph and vinylidene) | 27 |
| 17-6 | (TMS-C≡C-CH(OCO₂Me)-CH₂CH₂CHO) | PhCH₂NH₂ | (TMS-alkynyl cyclopentane with NCH₂Ph) + (TMS-vinyl cyclopentane with NCH₂Ph) | 30 + 17 |

TABLE 27-continued

| Example | Aldehyde | Amine | Amine produced P | Yields (%) (diastereomer ratio) | |
|---|---|---|---|---|---|
| 17-7 | (vinyl-CH(OCO₂Me)-CH₂CH₂CH₂-CHO) | H₂N-CH(Me)-Ph | N-CH(Me)-Ph on vinyl-cyclopentane | 55 | 1:1 |
| 17-8 | (vinyl-CH(OCO₂Me)-(CH₂)₃-CHO) | H₂N-CH(Me)-Ph | N-CH(Me)-Ph on vinyl-cyclopentane | 63 | 7:3 |
| 17-9 | 2-(1-(OCO₂Me)-allyl)benzaldehyde | H₂N-CH(Me)-Ph | N-CH(Me)-Ph on vinyl-indane | 55 | 74:23:1.8:1.2 |
| 17-10 | MeO₂CO-CH₂-C≡C-CH₂CH₂-CHO | H₂N-CH(Me)-Ph | allenyl-cyclopentane-N-CH(Me)-Ph | 31 | 6:4 |
| 17-11 | TMS-C≡C-CH(OCO₂Me)-CH₂CH₂-CHO | H₂N-CH(Me)-Ph | TMS-C≡C-cyclopentane-N-CH(Me)-Ph + TMS-CH=CH-cyclopentane-N-CH(Me)-Ph | 37 / 11 | 54:46 / 53:47 |

17-2I

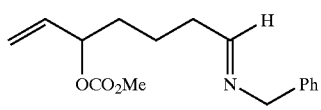

¹H-NMR, δ: 1.60–1.80 (m, 4H) 2.30–2.40 (m, 2H) 3.78 (s, 3H) 4.57 (q, J=6.7 Hz) 5.05–5.12 (br d, J=5.6 Hz, 1H) 5.21 (d, J=10.4 Hz, 1H) 5.31 (dd, J=1.2, 17.2 Hz, 1H) 5.79 (ddd, J=6.7, 10.4, 17.1 Hz, 1H) 7.20–7.40 (m, 5H) 7.76–7.80 (m, 1H)

17-2P

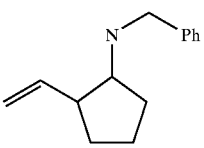

¹H-NMR, δ: 1.30 (m, 7H) 2.67–2.74 (m, 1H) 3.09 (dt like q, J=6.2, 12.8 Hz, 1H) 3.76 (s, 2H) 5.10 (d, J=10.9 Hz, 1H) 5.11 (d, J=17.0 Hz) 5.88 (ddd, J=8.3, 10.7, 16.7 Hz) 7.20–7.40 (m, 5H)

¹³C-NMR, δ: 21.62, 29.49, 31.14, 46.92, 52.20, 61.65, 115.60, 126.70, 128.07, 128.26, 138, 140.84

IR (neat): 3075, 3030, 2970, 2875, 1750, 1640, 1500, 1460, 1345, 1270, 1140, 1080, 030, 1005, 920, 740, 700 (cm$^{-1}$)

17-3I

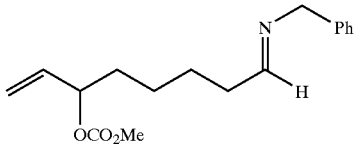

$^1$H-NMR, δ: 1.35–1.80 (m, 6H) 2.31 (dt like q, J=7.1, 11.9 Hz, 2H) 3.77 (s, 3H) 4.56 (s, 2H) 5.04 (dt like q, J=7.0, 13.0 Hz, 1H) 5.20 (d, J=10.4 Hz, 1H) 5.28 (d, J=17.1 Hz, 1H) 5.78 (ddd, J=6.7, 10.4, 17.1 Hz, 1H) 7.20–7.35 (m, 5H) 7.77–7.81 (m, 1H)

17-3P

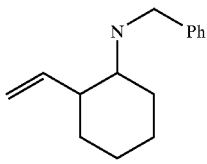

$^1$H-NMR, δ: 1.25–1.80 (m, 9H) 2.45–2.57 (m, 1H) 2.70 (dt, J=4.8, 9.2 Hz) 3.76 (s, 2H) 5.10 (d, J=15.5 Hz) 5.11 (d, J=11.6 Hz, 1H) 7.20–7.40 (m, 5H)

$^{13}$C-NMR, δ: 23.05, 23.11, 28.43, 29.11, 43.36, 50.91, 56.62, 115.44, 126.61, 128.00, 128.20, 139.37, 141.05

IR (neat): 3075, 3025, 2930, 2855, 1750, 1640, 1500, 1460, 1270, 1130, 1075, 1030, 1000, 915, 740, 700 (cm$^{-1}$)

17-4I

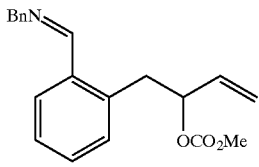

$^1$H-NMR, δ: 3.23 (dd, J=7.5, 13.6 Hz, 1H) 3.32 (dd, J=6.1, 13.4 Hz, 1H) 3.69 (s, 3H) 4.85 (s, 2H) 5.13 (d, J=7.9 Hz, 1H) 5.18 (d, J=14.5 Hz, 1H) 5.28 (dt like q, J=6.6, 13.7 Hz, 1H) 5.80 (ddd, J=6.5, 10.6, 17.2 Hz, 1H) 7.20–7.40 (m, 8H) 7.86 (dd, J=2.0, 7.0 Hz, 1H) 8.71 (s, 1H)

17-4P

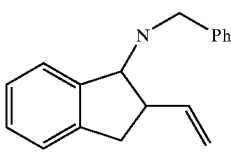

$^1$H-NMR, δ: 2.87 (dd, J=4.8, 15.6 Hz, 1H) 3.01 (dd, J=7.0, 15.8 Hz, 1H) 3.28 (dt, J=7.1, 13.7 Hz, 1H) 3.83 (d, J=13.2 Hz, 1H) 3.93 (d, J=13.2 Hz, 1H) 4.22 (d, J=6.4 Hz, 1H) 5.16 (dt, J=2.2, 10.4 Hz, 1H) 5.24 (d, J=16.5 Hz, 1H) 5.85 (ddd, J=8.7, 10.3, 17.30 Hz, 1H) 7.20–7.45 (m, 9H)

$^{13}$C-NMR, δ: 36.41, 48.61, 51.33, 64.75, 116.65, 124.50, 124.76, 126.23, 126.80, 127.33, 128.07, 128.28, 137.79, 140.69, 142.01, 144.78

IR (neat): 3400, 3075, 3040, 2930, 2850, 1750, 1640, 1610, 1500, 1460, 1370, 1330, 1270, 1140, 1080, 1035, 1010, 920, 800, 750, 700 (cm$^{-1}$)

17-5I

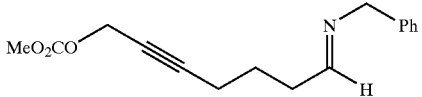

$^1$H-NMR, δ: 1.70–1.83 (m, 2H) 2.23–2.45 (m, 2H) 2.41 (br d, J=4.4 Hz, 2H) 3.80 (s, 3H) 4.57 (s, 2H) 4.71 (s, 2H) 7.20–7.40 (m, 5H) 7.78–7.85 (m, 1H)

17-5P

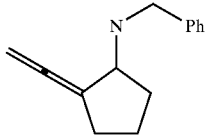

$^1$H-NMR, δ: 1.45–2.00 (m, 5H) 2.35–2.60 (m, 2H) 3.65–3.78 (m, 1H) 3.85 (s, 2H) 4.75–4.90 (m, 2H) 7.15–7.40 (m, 5H)

$^{13}$C-NMR, δ: 23.08, 29.68, 34.10, 51.86, 60.94, 105.84, 126.80, 128.30, 141.0, 202.4

17-6I

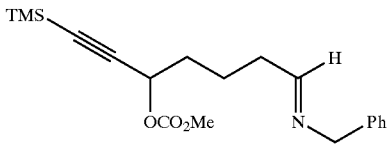

$^1$H-NMR, δ: 0.16 (s, 9H) 1.70–1.93 (m, 4H) 2.35 (dt like q, J=7.5, 12.0 Hz, 2H) 3.80 (s, 3H) 4.57 (s, 2H) 5.25 (t, J=6.1 Hz, 1H) 7.20–7.40 (m, 5H) 7.79 (t, J=4.7 Hz)

17-6P

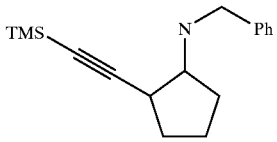

$^1$H-NMR, δ: 0.15 (s, 9H) 1.50–1.90 (m, 7H) 2.96 (dt like q, J=6.1, 11.2 Hz, 1H) 3.05–3.17 (m, 1H) 3.74 (d, J=12.8 Hz) 3.84 (d, J=12.8 Hz) 7.20–7.40 (m, 5H)

$^{13}$C-NMR, δ: 0.20, 21.56, 30.94, 31.06, 35.48, 52.23, 61.32, 107.30, 126.79, 128.18, 128.30, 140.60, 149.34

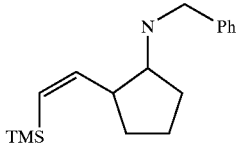

$^1$H-NMR, δ: 0.14 (s, 9H) 1.36 (br s, 1H) 1.46–1.96 (m, 6H) 2.81 (dt, J=6.2, 13.0 Hz) 3.13 (dt like q, J=6.2, 12.8 Hz, 1H) 3.76 (s, 2H) 5.71 (d, J=13.9 Hz) 6.43 (dd, J=10.5, 14.0 Hz) 7.20–7.40 (m, 5H)

$^{13}$C-NMR, δ: 0.41, 22.51, 31.94, 32.03, 46.52, 52.42, 62.15, 126.70, 128.03, 128.26, 130.01, 140.82, 149.34

IR (neat): 3400, 3175, 3030, 2965, 2875, 1605, 1500, 1460, 1345, 1250, 1140, 1070, 1030, 840, 760, 730, 700 (cm$^{-1}$)

17-7I

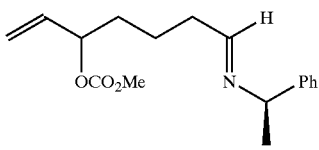

¹H-NMR, δ: 1.48 (d, J=6.7 Hz, 3H) 1.50–1.80 (m, 4H) 2.26–2.33 (m, 2H) 3.77 (s, 3H) 4.27 (q, J=6.7 Hz) 5.00–5.10 (m, 1H) 5.21 (d, J=10.4 Hz, 1H) 5.30 (d, J=17.3 Hz, 1H) 5.78 (ddd, J=6.6, 10.4, 17.0 Hz, 1H) 7.20–7.40 (m, 5H) 7.73 (t, J=5.1 Hz, 3H)

17-7P

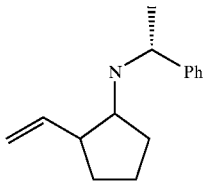

¹H-NMR, δ: 1.27 (d, J=6.6 Hz, 3H)
diastereomer 1.31 (d, J=6.6 Hz, 3H) 1.40–1.90 (m, 7H) 2.50 (dt, J=6.5, 13.6 Hz, 1H)
diastereomer 2.63–2.73 (m, 1H) 2.89 (dt, J=6.9, 12.9 Hz, 1H) 3.75–3.87 (m, 1H) 5.03 (m, 2H) 5.79–5.93 (m, 1H) 7.20–7.40 (m, 5H)
¹³C-NMR, δ: 20.88, 21.64, 24.44, 24.86, 29.24, 30.98, 31.37, 45.54, 47.09, 55.83, 56.23, 59.21, 60.17, 115.50, 115.56, 138.68, 138.77, 146.2, 146.4
IR (neat): 3400, 3075, 3040, 2975, 2875, 1760, 1690, 1640, 1610, 1500, 1460, 1380, 1275, 1140, 1035, 1005, 920, 770, 705 (cm⁻¹)

17-8I

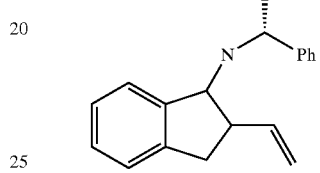

¹H-NMR, δ: 1.35–1.45 (m, 2H) 1.48 (d, J=6.7 Hz) 2.28 (dt, J=5.1, 12.2 Hz, 2H) 3.77 (s, 3H) 4.27 (q, J=6.7 Hz) 5.00–5.08 (m, 1H) 5.20 (dd, J=1.2, 10.5 Hz, 1H) 5.28 (dd, J=1.8, 17.1 Hz, 1H) 5.76 (ddd, J=6.9, 10.5, 17.3 Hz, 1H) 7.20–7.40 (m, 5H) 7.73 (t, J=5.1 Hz, 1H)

17-8P

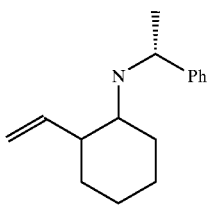

(major product)
¹H-NMR, δ: 1.25 (d, J=6.5 Hz, 3H) 1.30–1.70 (m, 9H) 2.42–2.52 (m, 1H) 2.52–2.64 (m, 1H) 3.47 (q, J=6.9 Hz, 1H) 5.15 (dd, J=2.2, 18.0 Hz, 1H) 5.16 (dd, J=2.2, 10.3 Hz, 1H) 6.06 (ddd, J=8.5, 10.7, 16.9 Hz, 1H) 7.20–7.35 (m, 5H)

¹³C-NMR, δ: 22.17, 24.37, 24.90, 29.47, 30.22, 42.38, 54.54, 55.14, 115.92, 126.58, 126.69, 128.24, 138.86, 146.62
IR (neat): 3300, 3050, 2950, 2850, 1760, 1700, 1640, 1610, 1500, 1460, 1380, 1280, 1140, 1005, 920, 770, 705 (cm⁻¹)

(minor product)
¹H-NMR, δ: 1.29 (d, J=6.6 Hz, 3H) 1.40–1.75 (m, 9H) 2.22–2.32 (m, 1H) 2.51 (dt, J=3.8, 8.2, 10.9 Hz, 1H) 3.47 (q, J=7.1 Hz, 1H) 5.04 (d, J=13.0 Hz, 1H) 5.08 (d, J=5.3 Hz, 1H) 5.93 (ddd, J=7.2, 10.6, 17.7 Hz, 1H) 7.20–7.35 (m, 5H)
¹³C-NMR, δ: 22.69, 23.46, 24.79, 28.13, 28.70, 44.14, 53.73, 54.27, 115.21, 126.59, 126.64, 140.02, 146.34
IR (neat): 2930, 2860, 1640, 1500, 1480, 1375, 1270, 1120, 920, 765, 700 (cm⁻¹)

17-9P

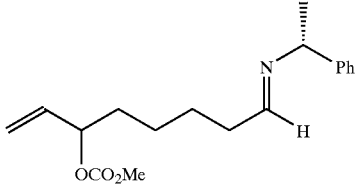

A:B:C:D=74:23:1.8:1.2
cis major diastereomer A
¹H-NMR, δ: 1.30 (d, J=6.5 Hz, 1H) 1.64 (s, 1H) 2.72 (dd, J=1.8, 15.5 Hz, 1H) 2.91 (dd, J=6.7, 15.8 Hz) 3.20–3.31 (m, 1H) 3.90–4.03 (m, 2H) 5.14 (dd, J=2.2, 10.1 Hz, 1H) 5.24 (dd, J=2.1, 17.0 Hz, 1H) 5.72 (ddd like dt, J=9.9, 17.1 Hz, 1H) 7.10–7.54 (m, 9H)
¹³C-NMR, δ: 25.33, 36.46, 47.99, 55.47, 62.88, 116.55, 124.26, 124.55, 126.34, 126.82, 126.95, 127.10, 128.34, 138.08, 141.24, 145.11, 145.94
IR (neat): 3080, 3040, 2975, 2940, 2875, 1735, 1645, 1610, 1500, 1460, 1380, 1305, 1270, 1130, 1010, 920, 800, 760, 705 (cm⁻¹)

cis minor diastereomer B
¹H-NMR, δ: 1.31 (d, J=6.6 Hz, 1H) 1.50 (br s, 1H) 2.92 (d, J=6.5 Hz, 2H) 3.07 (dt, J=6.8, 13.6 Hz, 1H) 3.90–4.10 (m, 2H) 5.14 (dd, J=1.2, 10.9 Hz, 1H) 5.15 (dd, J=1.2, 17.0 Hz, 1H) 5.94 (ddd, J=8.7, 10.4, 18.1 Hz, 1H) 7.10–7.54 (m, 9H)
¹³C-NMR, δ: 24.48, 35.96, 48.91, 55.36, 62.23, 116.30, 124.43, 124.89, 126.05, 126.86, 127.16, 128.42, 142.09, 145.77, 146.25
IR (neat): 3080, 3040, 2975, 2930, 2875, 1650, 1620, 1500, 1470, 1130, 1030, 930, 760, 705 (cm⁻¹)

C:D=1.8:1.2 diastereomixture
¹H-NMR, δ: (C)1.34 (d, J=6.6 Hz, 1H) (D)1.40 (d, J=6.6 Hz, 1H) 1.54 (s, 1H) 2.62 (dd, J=9.9, 15.5 Hz, 1H) (D)2.72 (dt, J=7.8, 15.3 Hz, 1H) (C)2.85 (dt, J=7.4, 15.5 Hz, 1H) (D)3.00–3.10 (m, 2H) (D)5.81 (ddd, J=7.9, 10.3, 18.1 Hz, 1H) (C)5.95 (ddd, J=8.6, 10.2, 17.2 Hz, 1H) 7.10–7.50 (m, 9H)
¹³C-NMR, δ: 24.76, 25.54, 36.65, 37.39, 53.87, 54.81, 55.50, 56.73, 65.70, 144.43, 114.87, 123.88, 124.09, 124.23, 124.55, 126.43, 126.78, 126.93, 127.18, 127.25, 128.30, 128.34, 140.77, 141.53, 141.8, 142.08, 145.60, 146.2
IR (neat): 3330, 3080, 2980, 2930, 2870, 1645, 16106 1500, 1485, 1460, 1375, 1215, 1185, 1140, 1030, 1000, 920, 750, 705 (cm⁻¹)

17-10I

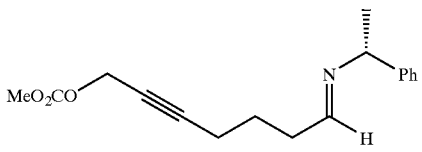

¹H-NMR, δ: 1.48 (d, J=6.7 Hz, 3H) 1.78 (dt, J=7.3, 14.6 Hz, 2H) 2.25–2.32 (m, 2H) 2.33–2.40 (m, 2H) 3.80 (s, 3H) 4.28 (q, J=6.7 Hz) 7.20–7.35 (m, 5H) 7.70 (t, J=4.7 Hz)

17-10P

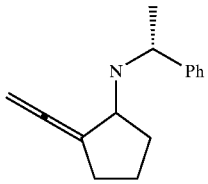

A:B=6:4

¹H-NMR, δ: 1.32 (d, J=6.7 Hz, 3H) (B)1.36 (d, J=6.7 Hz, 3H) 1.40–1.85 (m, 4H) 2.28–2.56 (m, 2H) 3.36–3.52 (m, 1H) (B)3.88 (q, J=6.7 Hz, 1H) 4.08 (q, J=6.7 Hz, 1H) 4.70–4.94 (m, 2H) 7.20–7.40 (m, 5H)

¹³C-NMR, δ: 23.54, 23.71, 24.52, 24.90, 34.01, 35.30, 55.90, 56.44, 58.33, 59.69, 77.11, 77.92, 106.15, 106.3, 126.69, 126.75, 126.99, 128.20, 128.42, 145.9, 146.0, 202.1, 202.4

IR (neat): 3400, 3075, 3050, 2975, 2875, 1965, 1500, 1460, 1380, 1280, 1135, 850, 765, 700 (cm⁻¹)

17-11I

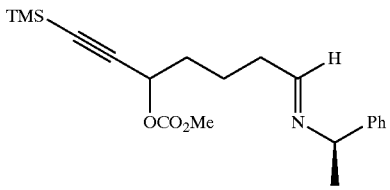

¹H-NMR, δ: 0.17 (s, 9H) 1.48 (d, J=6.7 Hz, 3H) 1.70–1.90 (m, 4H) 2.28–2.35 (m, 2H) 3.80 (s, 3H) 4.28 (q, J=6.6 Hz) 5.25 (t, J=6.0 Hz) 7.20–7.35 (m, 5H) 7.75 (t, J=4.7 Hz)

17-11P

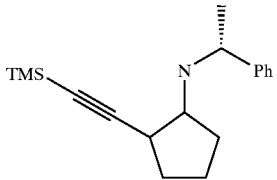

A:B-54:46 diastereomer A

¹H-NMR, δ: 0.20 (s, 9H) 1.34 (d, J=6.5 Hz) 1.40–1.50 (m, 1H) 1.65–1.90 (m, 6H) 2.78–2.87 (m, 1H) 2.94–3.00 (m, 1H) 3.89 (q, J=6.5 Hz, 1H) 7.20–7.40 (m, 5H)

¹³C-NMR, δ: 0.27, 21.07, 25.48, 30.94, 31.30, 34.22, 56.33, 59.75, 87.94, 107.65, 126.76, 126.86, 128.29, 145.83

IR (neat): 3400, 3070, 3030, 2970, 2870, 2160, 1500, 1460, 1365, 1255, 1100, 1030, 903, 845, 760, 700 (cm⁻¹)

diastereomer B

¹H-NMR, δ: 0.14 (s, 9H) 1.36 (d, J=6.5 Hz) 1.45–1.60 (m, 1H) 1.70–1.95 (m, 6H) 2.74–2.86 (m, 1H) 2.97 (dt like q, J=6.6, 13.2 Hz, 1H) 3.84 (q, J=6.6 Hz, 1H) 7.20–7.40 (m, 5H)

¹³C-NMR, δ: 0.15, 21.57, 23.71, 30.75, 30.84, 35.87, 55.80, 58.95, 87.99, 107.66, 126.72, 126.78, 128.25, 128.31, 146.00

IR (neat): 3400, 3075, 3030, 2950, 2875, 2170, 1610, 1500, 1480, 1460, 1380, 1255, 1145, 920, 850, 760, 740, 700 (cm⁻¹)

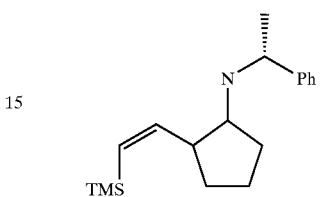

A:B=53:47 diastereomixture

¹H-NMR, δ: (B)0.10 (s, 9H) (A)0.17 (s, 9H) 1.30–1.90 (m, 7H) (B)2.60–2.74 (m, 1H) (A)2.74–2.84 (m, 1H) 2.85–2.96 (m, 1H) 3.75–3.84 (m, 1H) 5.60 (d, J=14.1 Hz, 1H) 6.34–6.46 (m, 1H) 7.20–7.35 (m, 5H)

¹³C-NMR, δ: 0.41, 0.46, 21.73, 22.49, 24.49, 24.97, 31.56, 31.62, 31.89, 32.37, 45.24, 46.57, 55.73, 56.46, 59.55, 60.41, 126.61, 128.24, 129.63, 130.14, 146.0, 146.5, 149.15, 149.33

IR (neat): 3400, 2960, 2860, 1650, 1500, 1465, 1370, 1250, 1140, 840, 760, 700 (cm⁻¹)

EXAMPLE 18-1

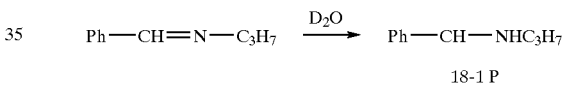

To a diethyl ether solution (8 ml) containing tetraisopropoxytitanium (426 mg, 1.5 mmol) and N-(phenylmethylidene)propylamine (147 mg, 1.0 mmol) was added at −78° C. a diethyl ether solution (2.46 ml) containing isopropylmagnesium chloride (3.0 mmol). The reaction liquid was heated to −50° C. over 1 hour and stirred for 2 hours. To the resulting titanium compound was added heavy water at −78° C., and the reaction liquid was heated to room temperature. The reaction liquid was separated into layers and the organic layer was dried with anhydrous magnesium sulfate and freed of organic solvent by vacuum distillation. The residues were purified by silica gel chromatography. Thus there was obtained 145 mg of amine 18-1P (yields: 97%).

¹H-NMR, δ: 7.19–7.36 (m, 5H) 3.79 (s, 1H) 2.60 (t, J=7.2 Hz, 2H) 1.45–1.62 (m, 2H) 1.45 (br s, 1H) 0.92 (t, J=7.4 Hz, 3H)

EXAMPLE 18-2

The procedure of Example 18-1 was repeated except that the titanium compound was given benzaldehyde (265 mg, 2.5 mmol) in place of heavy water and the reaction liquid was stirred at −50° C. for 2 hours. With water added, the reaction liquid was treated in the same manner as in Example 18-1. There was obtained 64 mg of amine 18-2P (yields: 25%).

$^1$H-NMR, δ: 6.97–7.80 (m, 10H) 4.99 (d, J=8.3 Hz, 1H) 3.76 (d, J=8.5 Hz, 1H) 2.50 (t, J=7.9 Hz, 2H) 1.26 (br s, 1H) 1.00–1.19 (m, 2H) 0.59 (t, J=7.4 Hz, 3H)

EXAMPLE 19-1

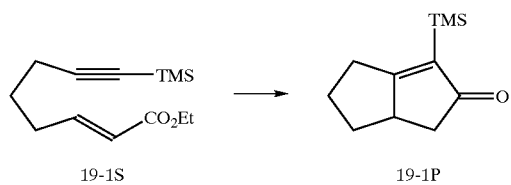

19-1S        19-1P

To a diethyl ether solution (4.3 ml) containing chlorotriisopropoxytitanium (155 mg, 0.6 mmol) was added at −78° C. under an argon atmosphere a diethyl ether solution (0.78 ml, 1.2 mmol) containing 19-1S (119 mg, 0.5 mmol) and isopropylmagnesium chloride. The reaction liquid was stirred for 30 minutes, heated to −20° C. over 1 hour, and stirred for 2 hours. With 1N hydrochloric acid added and heating to room temperature, the reaction liquid was extracted with diethyl ether. The organic layer was washed with a saturated aqueous solution of sodium hydrogen carbonate and dried with anhydrous magnesium sulfate and freed of organic solvent by vacuum distillation. The residues were purified by silica gel chromatography. Thus there was obtained 58 mg of 19-1P in cyclized form (yields: 60%).

19-1P $^1$H-NMR, δ: 0.19 (s, 9H) 1.10 (d/q, J=7.9, 11.9 Hz, 1H) 1.87–2.20 (m, 3H) 2.03 (d/d, J=3.9, 17.6 Hz, 1H) 2.54 (d/t, J=19.4, 8.9 Hz, 1H) 2.57 (d/d/d, J=0.8, 6.5, 17.6 Hz, 1H) 2.66 (d/d/d, J=3.0, 10.7, 19.4 Hz, 1H) 2.74–2.87 (m, 1H)

$^{13}$C-NMR, δ 1.11, 25.74, 27.54, 30.98, 43.14, 48.51, 135.16, 198.84, 214.70

IR (neat): 2970, 2920, 2870, 1690, 1610, 1420, 1250, 1230, 1140, 930, 870, 860, 840, 760, 690 (cm$^{-1}$)

EXAMPLE 19-2

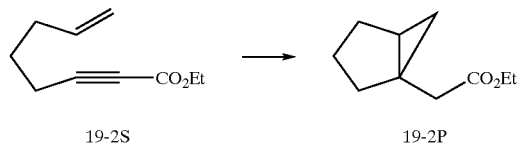

19-2S        19-2P

The procedure of Example 19-1 was repeated so that 19-2S (83 mg, 0.5 mmol) gave 62 mg of 19-2P in cyclized form (yields: 74%).

19-2P $^1$H-NMR, δ: 0.36 (d/d, J=4.8, 8.2 Hz, 1H) 0.45 (t, J=4.8 Hz, 1H) 1.08–1.22 (m, 1H) 1.25 (t, J=7.1 Hz, 3H) 1.50–1.86 (m, 6H) 2.37 (d, J=15.0 Hz, 1H) 2.47 (d, J=15.0 Hz, 1H) 4.14 (q, J=7.1 Hz, 2H)

$^{13}$C-NMR, δ: 12.09, 14.28, 21.37, 23.36, 25.23, 27.47, 31.77, 41.00, 59.99, 172.70

IR (neat): 2950, 2860, 1740, 1260, 1180, 1170, 1150, 1040 (cm$^{-1}$)

EXAMPLE 19-3

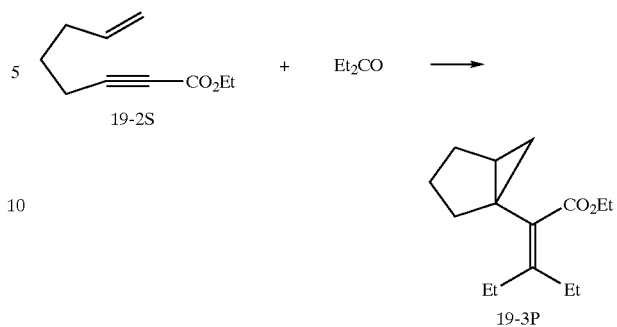

19-3P

As in Example 19-1, reaction was performed on 19-2S (83 mg, 0.5 mmol), chlorotriisopropoxytitanium (155 mg, 0.6 mmol), and isopropylmagnesium chloride (1.2 mmol). The reaction liquid was given diethyl ketone (0.076 ml, 0.75 mmol) and stirred at room temperature for 3 hours. With 1N hydrochloric acid added, the reaction liquid was treated and purified in the same manner as in Example 19-1. Thus there was obtained 68 mg of 19-3P (yields: 57%).

19-3P $^1$H-NMR, δ: 0.47 (d/d, J=4.7, 8.3 Hz, 1H) 0.65 (t, J=4.7 Hz, 1H) 1.00 (t, J=7.5 Hz, 3H) 1.04 (t, J=7.6 Hz, 3H) 1.17–1.23 (m, 1H) 1.29 (t, J=7.1 Hz, 3H) 1.54–1.93 (m, 6H) 2.17 (d/q, J=13.9, 7.5 Hz, 1H) 2.23 (d/q, J=13.9, 7.5 Hz, 1H) 2.27 (d/q, J=13.4, 7.6 Hz, 1H) 2.38 (d/q, J=13.4, 7.6 Hz, 1H) 4.15 (d/q, J=10.7, 7.1 Hz, 1H) 4.20 (d/q, J=10.7, 7.1 Hz, 1H)

$^{13}$C-NMR, δ: 12.40, 13.31, 14.40, 14.45, 21.17, 24.28, 25.15, 27.66, 28.44, 33.57, 59.70, 130.47, 152.23, 170.42

IR (neat): 2970, 2940, 2870, 1720, 1640, 1220, 1200, 1070 (cm$^{-1}$)

EXAMPLE 20-1

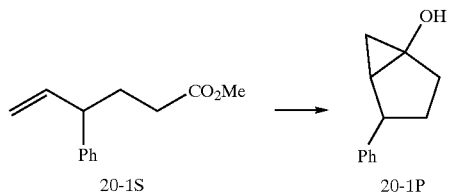

20-1S        20-1P

To a diethyl ether solution (12 ml) containing tetraisopropoxytitanium (568 mg, 2.0 mmol) and 20-1S (204 mg, 1.0 mmol) was added at −45° C. a diethyl ether solution (3.08 ml) containing isopropylmagnesium chloride (4.0 mmol). The reaction liquid was stirred for 1 hour and heated to 0° C. over 2.5 hours. With tetrahydrofuran (3 ml) and water (1.3 ml) added, the reaction liquid was heated to room temperature and stirred for 30 minutes. The supernatant organic layer was isolated and dried with anhydrous magnesium sulfate and freed of organic solvent by vacuum distillation. The residues were purified by silica gel chromatography. Thus there was obtained 134 mg of 20-1P in cyclopropyl alcohol form (yields: 77%, diastereomer ratio A:B=55:45).

20-1P

A $^1$H-NMR, δ: 0.76 (dd, J$_1$=6.0 Hz, J$_2$=5.4 Hz, 1H) 1.04 (m, 1H) 1.52 (dd, J$_1$=9.6 Hz, J$_2$=5.4 Hz, 1H) 1.88–1.70 (m, 2H) 1.94–2.18 (m, 2H) 2.38 (br s, 1H) 3.02 (d, J=6.6 Hz, 1H) 7.15–7.35 (m, 5H)

¹³C-NMR, δ: 16.41, 29.92, 30.58, 31.44, 45.13, 65.34, 125.90, 127.05, 128.41, 147.00

B

¹H-NMR, δ: 0.90 (dd, J₁=J₂=5.7 Hz, 1H) 0.99 (dd, J₁=9.4 Hz, J₂=5.7 Hz, 1H) 1.20 (m, 1H) 1.68 (m, 1H) 2.00–2.23 (m, 3H) 3.55 (m, 1H) 7.15–7.33 (m, 5H)

¹³C-NMR, δ: 13.48, 28.36, 29.31, 34.33, 43.47, 63.43, 125.99, 126.98, 128.20, 144.15

EXAMPLE 20-2

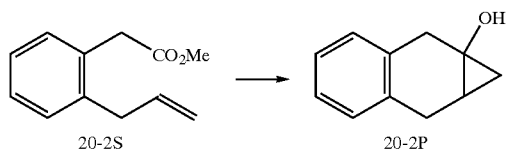

The procedure of Example 20-1 was repeated to make 20-2S into 20-2P in cyclized form (yield: 98%).

20-2P

¹H-NMR, δ: 0.45 (dd, J₁=J₂=5.7 Hz, 1H) 0.71 (dd, J₁=10.2 Hz, J₂=5.7 Hz, 1H) 1.50 (m, 1H) 2.74 (br s, 1H) 2.90 (d, J_{AB}=15.6 Hz, 1H) 3.23 (d, J_{AB}=15.6 Hz, 1H) 3.27 (m, 2H) 7.00–7.17 (m, 4H)

¹³C-NMR, δ: 12.15, 19.37, 30.17, 37.19, 55.60, 125.94, 126.44, 128.72, 128.91, 133.74, 134.96

EXAMPLE 21-1

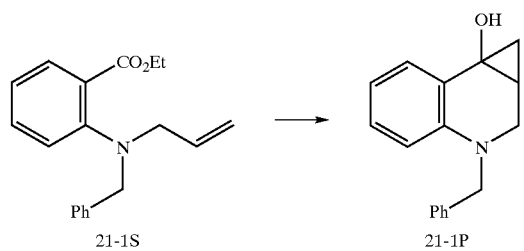

To a diethyl ether solution (5 ml) containing 21-1S (148 mg, 0.5 mmol) was added at −78° C. tetraisopropoxytitanium (213 mg, 0.75 mmol) and was further added a diethyl ether solution (0.97 ml) containing isopropylmagnesium chloride (1.45 mmol). The reaction liquid was heated to room temperature over 2 hours. With tetrahydrofuran (2.5 ml) and water (1.2 ml) added, the reaction liquid was extracted with diethyl ether. The organic layer was dried with anhydrous magnesium sulfate and freed of organic solvent by vacuum distillation. The residues were purified by silica gel chromatography. Thus there was obtained 118 mg of 21-1P in cyclopropyl alcohol form (yields: 94%).

EXAMPLES 21-2 TO 21-7

The procedure of Example 21-1 was repeated to give the results as shown in Table 28.

TABLE 28

| Example | Starting material | Reaction product | Yields (%) |
|---|---|---|---|
| 21-1 | | | 94 |
| 21-2 | | | 94 |
| 21-3 | | | 74 |
| 21-4 | | | 80 |

TABLE 28-continued

| Example | Starting material | Reaction product | Yields (%) |
|---|---|---|---|
| 21-5 | | | 80 |
| 21-6 | | | 75 |
| 21-7 | | | 59 |

21-1P
$^1$H-NMR, δ: 7.62 (dd, J=1.7, 7.5 Hz, 1H) 7.28 (m, 5H) 7.05 (dt, J=1.7, 7.8 Hz, 1H) 6.83 (t, J=7.2 Hz, 1H) 6.61 (d, J=8.3 Hz, 1H) 4.46 (d, J=15.5 Hz, 1H) 4.22 (d, J=15.5 Hz, 1H) 3.14 (d, J=2.1 Hz, 2H) 1.88 (m, 1H) 1.51 (t, J=5.5 Hz, 1H) 1.23 (dd, J=5.0, 9.6 Hz, 1H)
$^{13}$C-NMR, δ: 142.32, 138.21, 128.83, 128.48, 127.37, 126.91, 126.66, 124.30, 118.00, 112.22, 54.55, 53.27, 45.20, 28.95, 16.47
IR (neat): 3250, 2980, 2950, 2820, 2730, 2160, 1565, 1463, 1418, 1320, 1290, 1255, 1210, 1180, 1135, 1090, 1035, 1010, 990, 910, 870, 690, 660 (cm$^{-1}$)

21-2P
$^1$H-NHR, δ: 7.54 (dd, J=7.5, 1.5 Hz, 1H) 7.09 (m, 3H) 6.33 (s, 1H) 4.18 (dd, J=10.7, 5.5 Hz, 1H) 3.83 (d, J=10.7 Hz, 1H) 2.88 (br s, 1H) 1.76 (dd, J=9.4, 5.9 Hz, 1H) 1.01 (t, J=5.4 Hz, 1H)
$^{13}$C-NMR, δ: 145.46, 132.88, 132.56, 120.97, 129.81, 119.38, 108.98, 91.99, 60.81, 46.38, 28.42, 24.00
IR (neat): 3340, 3050, 2960, 2925, 2875, 1615, 1563, 1480, 1459, 1475, 1332, 1303, 1240, 1225, 1156, 910, 770, 742, 680 (cm$^{-1}$)

21-3P
$^1$H-NMR, δ: 7.56 (dd, J=7.0, 1.2 Hz, 1H) 7.15 (m, 4H) 6.57 (s, 1H) 4.21 (dt, J=13.1, 3.8 Hz, 1H) 3.41 (dt, J=11.9, 9.2 Hz, 1H) 2.81 (br s, 1H) 2.16 (m, 2H) 1.81 (m, 1H) 1.40 (dd, J=10.0, 6.2 Hz, 1H) 1.13 (t, J=6.3 Hz, 1H)
$^{13}$C-NMR, δ: 140.64, 136.05, 128.03, 120.63, 119.93, 108.54, 96.23, 52.98, 36.74, 21.99, 21.18, 17.02
IR (neat): 3380, 3075, 2950, 2980, 1720, 1670, 1625, 1570, 1535, 1495, 1480, 1430, 1390, 1370, 1340, 1325, 1278, 1260, 1235, 1175, 1120, 1080, 1055, 1025, 980, 950, 925, 800, 780, 760, 690 (cm$^{-1}$)

21-4P
$^1$H-NMR, δ: 6.46 (dd, J=3.0, 1.2 Hz, 1H) 6.18 (t, J=3.0 Hz, 1H) 6.00 (dd, J=3.4, 1.2 Hz, 1H) 4.23 (dd, J=11.4, 5.7 Hz, 1H) 3.70 (d, J=11.4 Hz, 1H) 2.76 (br s, 1H) 2.17 (m, 1H) 1.67 (dd, J=9.3, 5.7 Hz, 1H) 0.91 (t, J=5.3 Hz, 1H)
$^{13}$C-NMR, δ: 138.48, 113.89, 112.04, 98.35, 61.14, 48.47, 27.48, 23.63
IR (nujor): 3800, 2970 (nujor), 2900 (nujor), 1580, 1518, 1490 (nujor), 1450, 1402 (nujor), 1360, 1330, 1262, 1250, 1121, 1075, 960, 935, 920, 855, 805, 758, 732 (cm$^{-1}$)

21-5P
$^1$H-NMR, δ: 6.51 (dd, J=2.6, 1.8 Hz, 1H) 6.22 (dd, J=3.5, 1.7 Hz, 1H) 6.12 (t, J=3.2 Hz, 1H) 3.88 (ddd, J=12.9, 5.9, 1.9 Hz, 1H) 3.43 (td, J=12.9, 4.7 Hz, 1H) 2.16 (tdd, J=13.0, 5.6, 3.3 Hz, 1H) 2.00 (m, 1H) 1.64 (m, 1H) 1.30 (dd, J=9.9, 6.0 Hz, 1H) 1.00 (t, J=6.0 Hz, 1H)
$^{13}$C-NMR, δ: 132.86, 119.08, 107.05, 102.87, 52.95, 40.56, 21.51, 21.04, 16.24
IR (nujor): 3150, 2890 (nujor), 2845 (nujor), 1685, 1630, 1540, 1515, 1480, 1460 (nujor), 1395 (nujor), 1319, 1298, 1242, 1215, 1165, 1098, 1055, 1035, 988, 940, 903, 870, 825, 750, 680, 665 (cm$^{-1}$)

21-6P
$^1$H-NMR, δ: 0.90 (t, J=4.5 Hz, 1H) 0.96 (dd, J=4.7, 8.9 Hz, 1H) 1.44–1.54 (m, 1H) 2.37 (d, J=9.33 Hz, 1H) 2.96 (dd, J=8.76, 3.48 Hz, 1H) 2.91 (dd, J=13.89, 5.25 Hz, 1H) 3.02 (dd, J=13.86, 4.92 Hz, 1H) 3.38 (dd, J=6.60, 5.31 Hz, 1H) 3.64 (dd, J=15.51, 13.86 Hz, 2H) 7.10–7.38 (m, 10H)

21-7P
$^1$H-NMR, δ: 0.75 (dd, J=10.62, 4.47 Hz, 1H) 0.96 (dd, J=6.16, 4.47 Hz, 1H) 1.20–1.30 (m, 1H) 1.56–1.68 (m, 1H) 1.88–2.00 (m, 1H) 2.18–2.28 (m, 1H) 2.60–2.70 (m, 1H) 3.14 (dd, J=6.42, 4.77 Hz, 1H) 3.49 (dd, J=6.06, 5.37 Hz, 1H) 3.55 (d, J=13.9 Hz, 1H) 3.69 (d, J=13.80 Hz, 1H) 7.10–7.40 (m, 10H)

EXAMPLE 21-8

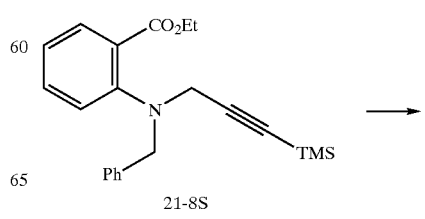

21-8S

117
-continued

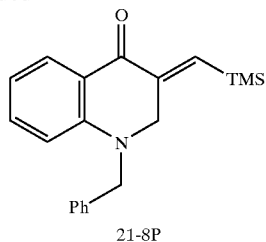
21-8P

To a diethyl ether solution (5 ml) containing 21-8S (183 mg, 0.5 mmol) was added at −78° C. tetraisopropoxytitanium (156 mg, 0.55 mmol) and was further added a diethyl ether solution (0.7 ml) containing isopropylmagnesium chloride (1.05 mmol). The reaction liquid was stirred at −50° C. for 2 hours. With tetrahydrofuran (2.5 ml) and water (1.2 ml) added, the reaction liquid was extracted with diethyl ether. The organic layer was dried with anhydrous magnesium sulfate and freed of organic solvent by vacuum distillation. The residues were purified by silica gel chromatography. Thus there was obtained 101 mg of 21-8P in cyclic enone form (yields: 63%).

EXAMPLE 21-9 TO 21-18

The procedure of Example 21-1 was repeated to give the results as shown in Table 29.

TABLE 29

| Example | Starting material | Reaction product | Yields (%) |
|---|---|---|---|
| 21-8 | | | 63 |
| 21-9 | | | 61 |
| 21-10 | | | 50 |
| 21-11 | | | 62 |
| 21-12 | | | 57 |

TABLE 29-continued

| Example | Starting material | Reaction product | Yields (%) |
|---|---|---|---|
| 21-13 |  | 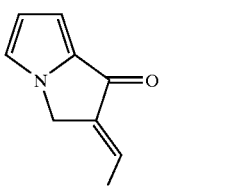 | 53 |
| 21-14 | 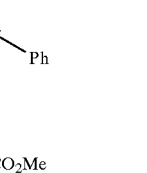 | 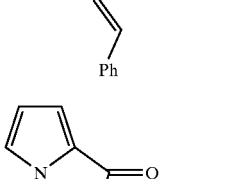 | 76 |
| 21-15 | 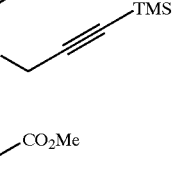 | 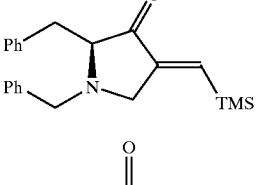 | 76 |
| 21-16 | 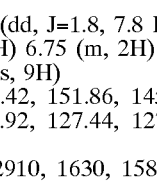 | 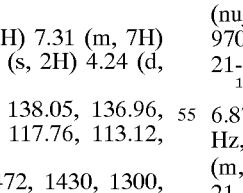 | 76 |
| 21-17 | 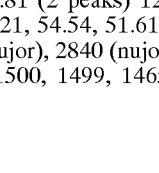 | 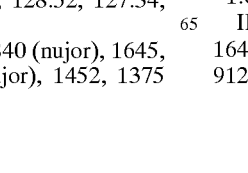 | 75 |
| 21-18 | | | 75 |

21-8P $^1$H-NMR, δ: 8.04 (dd, J=1.8, 7.8 Hz, 1H) 7.31 (m, 7H) 6.98 (t, J=1.8 Hz, 1H) 6.75 (m, 2H) 4.54 (s, 2H) 4.24 (d, J=1.7 Hz, 2H) 0.07 (s, 9H)

$^{13}$C-NMR, δ: 189.42, 151.86, 145.91, 138.05, 136.96, 135.49, 129.65, 128.92, 127.44, 127.28, 117.76, 113.12, 54.49, 53.87, 0.74

IR (neat): 2980, 2910, 1630, 1583, 1472, 1430, 1300, 1223, 1190, 1148, 1092, 950, 833, 816, 724, 703, 655 (cm$^{-1}$)

21-9P $^1$H-NMR, δ: 8.08 (dd, J=1.8, 7.9 Hz, 1H) 7.81 (t, J=2.2 Hz, 1H) 7.33 (m, 11H) 6.78 (t, J=7.4 Hz, 1H) 6.67 (d, J=8.6 Hz, 1H) 4.60 (d, J=2.3 Hz, 2H) 4.58 (s, 2H)

$^{13}$C-NMR, δ: 183.5, 150.9, 136.61, 135.58, 135.37, 131.8, 129.79, 129.17, 128.81 (2 peaks) 128.78, 128.52, 127.34, 126.77, 117.52, 113.21, 54.54, 51.61

IR (neat): 2920 (nujor), 2840 (nujor), 2840 (nujor), 1645, 1603, 1587, 1556, 1500, 1499, 1465 (nujor), 1452, 1375 (nujor), 1350, 1330, 1270, 1250, 1222, 1198, 1170, 1099, 970, 750, 722, 700 (cm$^{-1}$)

21-10P $^1$H-NMR, δ: 8.04 (dd, J=1.7, 7.9 Hz, 1H) 7.31 (m, 5H) 6.87 (br t, J=7.7 Hz, 1H) 6.75 (t, J=7.4 Hz, 1H) 6.68 (d, J=8.4 Hz, 1H) 4.59 (s, 2H) 4.22 (s, 2H) 2.06 (q, J=7.4 Hz, 1H) 1.43 (m, 2H) 1.25 (m, 6H) 0.87 (t, J=6.8 Hz, 3H)

21-11P $^1$H-NMR, δ: 7.77 (d, J=8.3 Hz, 1H) 7.41 (m, 2H) 7.20 (m, 1H) 7.15 (s, 1H) 7.11 (t, J=2.3 Hz, 1H) 4.99 (d, J=2.3 Hz, 2H) 0.29 (s, 9H)

$^{13}$C-NMR, δ: 181.10, 148.91, 135.73, 134.90, 132.10, 131.80, 125.46, 124.14, 121.68, 110.47, 100.86, 45.59, −1.09

IR (nujor): 2925 (nujor), 2855 (nujor), 1702, 1630, 1543, 1648 (nujor), 1382 (nujor), 1353, 1250, 1228, 1170, 1152, 912, 880, 860, 847, 735, 718 (cm$^{-1}$)

21-12P

¹H-NMR, δ: 7.78 (d, J=7.2 Hz, 1H) 7.68 (s, 1H) 7.52 (m, 6H) 7.40 (t, J=6.9 Hz, 1H) 7.21 (t, J=6.9 Hz, 1H) 7.15 (9, 1H) 5.30 (s, 2H)

21-13P

¹H-NMR, δ: 7.76 (d, J=8.2 Hz, 1H) 7.38 (m, 2H) 7.19 (m, 1H) 7.09 (d, J=1.1 Hz, 1H) 6.88 (tt, J=7.8, 2.2 Hz, 1H) 4.91 (d, J=2.2 Hz, 2H) 2.30 (q, J=7.4 Hz, 2H) 1.57 (m, 2H) 1.33 (m, 6H) 0.90 (t, J=6.7 Hz, 3H)

¹³C-NMR, δ: 182.00, 138.10, 137.79, 136.24, 134.57, 131.72, 125.18, 124.03, 121.44, 110.33, 99.96, 43.96, 31.62, 29.83, 29.09, 28.33, 22.53, 14.03

IR (nujor): 2925 (nujor), 2850 (nujor), 1708, 1652, 1543, 1470 (nujor), 1380 (nujor), 1350, 1280, 1230, 1180, 1155, 810, 738 (cm⁻¹)

21-14P

¹H-NMR, δ: 7.08 (dd, J=2.2, 1.1 Hz, 1H) 6.94 (t, J=2.2 Hz, 1H) 6.86 (dd, J=4.4, 1.1 Hz, 1H) 6.52 (dd, J=4.0, 2.2 Hz, 1H) 4.86 (d, J=2.3 Hz, 2H) 0.22 (s, 9H)

¹³C-NMR, δ: 177.69, 149.37, 133.08, 122.15, 116.64, 109.46, 107.79, 47.66, −1.08

IR (nujor): 2990 (nujor), 2920 (nujor), 1725, 1660, 1565, 1495 (nujor), 1410 (nujor), 1348, 1302, 1272, 1170, 1110, 1090, 1075, 990, 935, 918, 890, 875, 802, 775, 742, 720 (cm⁻¹)

21-15P

¹H-NMR, δ: 7.52 (t, J=2.2 Hz, 1H) 7.49–7.35 (m, 4H) 7.11 (d, J=1.7 Hz, 1H) 6.87 (dd, J=4.1, 1.1 Hz, 1H) 6.54 (dd, J=4.0, 2.3 Hz) 5.16 (d, J=2.1 Hz, 2H)

¹³C-NMR, δ: 179.28, 134.75, 134.48, 131.54, 130.05, 129.63, 129.06, 122.06, 116.75, 111.65, 108.85, 47.59

IR (nujor): 2980 (nujor), 2875 (nujor), 1695, 1645, 1538, 1465 (nujor), 1383 (nujor), 1313, 1138, 1039, 963, 781, 755, 699 (cm⁻¹)

21-16P

¹H-NMR, δ: 7.04 (d, J=1.7 Hz, 1H) 6.81 (m, 1H) 6.70 (tt, J=7.8, 2.1 Hz, 1H) 6.50 (dd, J=4.0, 2.3 Hz, 1H) 4.86 (d, J=2.2 Hz, 2H) 2.21 (q, J=7.6 Hz, 2H) 1.52 (m, 2H) 1.42–1.25 (m, 6H) 0.89 (t, J=6.6 Hz, 3H)

¹³C-NMR, δ: 178.90, 136.34, 135.30, 135.25, 121.84, 116.26, 108.39, 45.89, 31.53, 29.50, 28.94, 28.30, 22.45, 13.95

IR (neat): 2960, 2880, 1718, 1663, 1543, 1499, 1420, 1388, 1329, 1285, 1155, 1109, 1069, 1031 (cm⁻¹)

21-17P

¹H-NMR, δ: 0.14 (s, 3H) 3.11 (m, 1H) 3.15 (dd, J=2.46, 14.28 Hz, 2H) 3.26 (t, J=4.53, 5.49 Hz, 1H) 3.32–3.37 (m, 1H) 3.40 (d, J=13.32 Hz, 1H) 3.83 (d, J=14.82 Hz, 1H) 4.13 (d, J=13.20 Hz, 1H) 6.81 (t, J=2.76, 2.13 Hz, 1H) 7.20–7.50 (m, 10H)

21-18P

¹H-NMR, δ: 0.13 (s, 3H) 2.51–2.73 (m, 2H) 3.04–3.14 (m, 1H) 3.02 (dd, J=5.49, 13.86 Hz, 1H) 3.13 (dd, J=6.03, 13.74 Hz, 1H) 3.49 (t, J=6.03, 6.06 Hz, 1H) 3.56 (d, J=13.74 Hz, 1H) 3.90 (d, J=13.47 Hz, 1H) 6.70 (s, 1H) 7.15–7.33 (m, 10H)

Referential Example 1

To a THF suspension (50 ml) containing sodium hydride (0.92 g, 21 mmol, 55% in oil) was added dropwise at 0° C. diethyl malonate (3.2 g, 20 mmol). The reaction liquid was heated to room temperature and stirred for 1 hour. The reaction liquid was stirred overnight together with allyl bromide (2.9 g, 24 mmol). With water added, the reaction liquid was extracted with ether. The organic layer was washed with a saturated aqueous solution of sodium chloride and dried with anhydrous magnesium sulfate. After solvent removal, the residues were purified by silica gel chromatography. Thus there was obtained 2.88 g of diethyl allylmalonate (yields: 72%). This product was identical with commercial one.

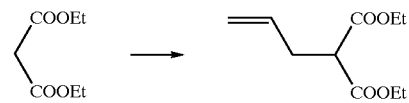

Referential Example 2

The procedure of Referential Example 1 was repeated to give 3.56 g of diethyl allyl(benzyl)malonate (yields: 82%) from diethyl allylmalonate (3.0 g, 15 mmol) and benzyl bromide (3.1 g, 18 mmol).

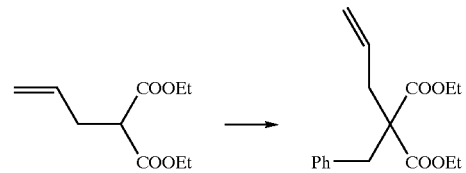

Characteristic Values of diethyl allyl(benzyl)malonate

¹H-NMR, δ: 1.24 (t, J=7.1 Hz, 6H) 2.57 (d, J=7.3 Hz, 2H) 3.24 (s, 2H) 4.13–4.25 (m, 4H) 5.13–5.18 (m, 2H) 5.70–5.85 (m, 1H) 7.09–7.20 (m, 2H) 7.21–7.30 (m, 3H)

¹³C-NMR, δ: 14.59, 37.09, 38.67, 59.42, 61.78, 119.68, 127.46, 128.77, 130.59, 133.27, 136.68, 171.32

IR (neat): 3080, 2990, 1730, 1640, 1495, 1445, 1370, 1280, 1250, 1210, 1190, 1150, 1100, 1080, 1040, 920, 860, 740, 700

Elemental analysis value $C_{17}H_{22}O_4$:

Calculated value (%) C,70.32; H,7.64. Found value (%) C,69.82; H,7.82.

EXAMPLE 22-1

To an ether solution (7.5 ml) containing tetraisopropoxytitanium (0.284 g, 1.0 mmol) and diethyl allyl(benzyl) malonate (0.145 g, 0.5 mmol) was added dropwise at −50° C. 1.53 ml of 1.31M ether solution containing isopropylmagnesium chloride (2 mmol). Upon stirring at −40° C. for 1 hour, the reaction liquid turned from yellow into brown. With 1N hydrochloric acid added, the reaction liquid was stirred at room temperature for 15 minutes. After treatment and purification as in Referential Example 1, there was obtained diethyl benzylmalonate in deallylated form (yields: 97%).

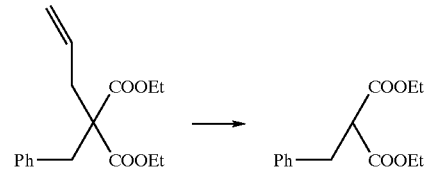

EXAMPLE 22-2

To an ether solution (7.5 ml) containing tetraisopropoxytitanium (0.284 g, 1.0 mmol) and diethyl malonate (0.145 g, 0.5 mmol) was added dropwise at −50° C. 1.53 ml of 1.31M ether solution containing isopropylmagnesium chloride (2 mmol). Upon stirring at −40° C. for 1 hour, the reaction liquid turned from yellow into brown. The reaction liquid was stirred together with benzaldehyde (0.080 g, 0.75 mmol) at 0° C. for 1 hour. With 1N hydrochloric acid added, the reaction liquid was stirred at room temperature for 15 minutes. After treatment and purification as in Referential Example 1, there was obtained diethyl benzylmalonate in deallylated form (yields: 97%).

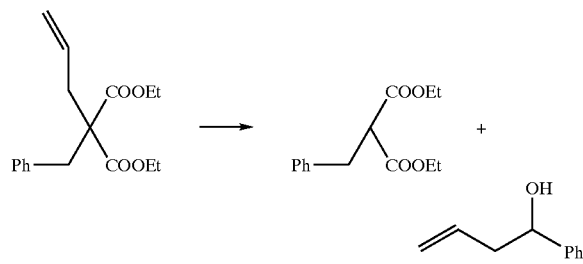

Referential Example 3

The procedure of Referential Example 2 was repeated to give 9.01 g of diethyl allyl(5-iodopentyl)malonate (yields: 70%) from diethyl allylmalonate (6.5 g, 325 mmol) and 1,5-diiodopentane (21.1 g, 65 mmol).

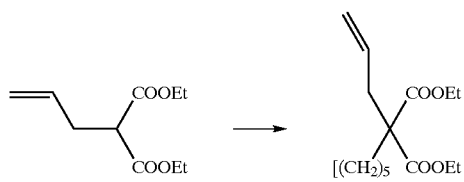

Characteristic Values of diethyl allyl(5-iodopentyl)malonate $^1$H-NMR, δ: 1.24 (t, J=7.1 Hz, 6H) 1.15–1.30 (m, 2H) 1.40 (tt, $J_1$, $J_2$=7.3 Hz, 2H) 1.76–1.88 (m, 4H) 2.63 (d, J=7.7 Hz, 2H) 3.16 (t, J=7.0 Hz, 2H) 4.18 (q, J=7.1 Hz, 4H) 5.06–5.12 (m, 2H) 5.56–5.70 (m, 1H)

$^{13}$C-NMR, δ: 6.52, 14.12, 22.80, 30.62, 32.01, 33.06, 37.02, 57.35, 61.15, 118.81, 132.54, 171.21

IR (neat): 3090, 2885, 2840, 1735, 1645, 1470, 1450, 1370, 1290, 1230, 1210, 1150, 1100, 1030, 925, 860

Elemental analysis value $C_{15}H_{25}O_4I$:

Calculated value (%) C,45.47; H,6.36. Found value (%) C,45.22; H,6.47.

Referential Example 4

To a THF suspension (2.1 ml) containing copper iodide (0.228 g, 1.2 mmol) was added dropwise at −10° C. butyl lithium (2.4 mmol in 0.88 ml of 2.68M hexane solution). The reaction liquid was heated to 0° C. over 30 minutes and then given diethyl allyl(5-iodopentyl)malonate (0.40 g, 1 mmol), followed by stirring at 0° C. for 5 hours. After addition of a saturated aqueous solution of ammonium chloride, the reaction product was purified as in Referential Example 1. Thus there was obtained 0.234 g of diethyl allyl(nonyl)malonate (yields: 75%).

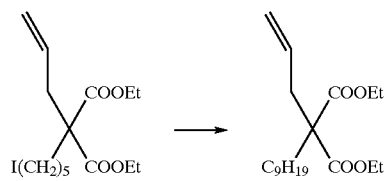

Characteristic Values of diethyl allyl(nonyl)malonate $^1$H-NMR, δ: 0.88 (t, J=7.0 Hz, 3H) 1.17–1.25 (m, 20H) 1.83–1.88 (m, 2H) 2.64 (d, J=7.4 Hz, 2H) 4.18 (q, J=7.1 Hz, 4H) 5.06–5.12 (m, 2H) 5.57–5.72 (m, 1H)

13C-NMR, δ: 14.06, 14.12, 22.66, 23.80, 29.27, 29.33, 29.81, 31.89, 32.20, 36.94, 57.51, 61.05, 118.63, 132.74, 171.40

IR (neat): 3080, 2920, 2840, 1730, 1640, 1470, 1450, 1360, 1200, 1140, 1090, 1030, 910, 850

Elemental analysis value $C_{19}H_{34}O_4$:

Calculated value (%) C,69.90; H,10.50. Found value (%) C,69.52; H,10.80.

EXAMPLE 22-3

The procedure of Example 22-1 was repeated to produce 0.142 g of diethyl nonylmalonate (yields: 92%) from diethyl allyl(nonyl)malonate (0.175 g, 0.54 mmol) by deallylating reaction.

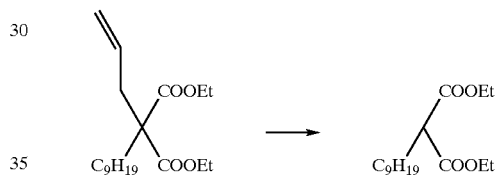

Characteristic Values of diethyl nonylmalonate $^1$H-NMR, δ: 0.87 (t, J=7.1 Hz, 3H) 1.23–1.29 (m, 20H) 1.87–1.89 (m, 2H) 3.30 (t, J=7.6 Hz, 1H) 4.19 (q, J=7.1 Hz, 4H)

$^{13}$C-NMR, δ: 14.08, 22.65, 27.33, 28.76, 29.21, 29.47, 31.86, 52.12, 61.21, 169.60

IR (neat): 2910, 2840, 1750, 1730, 1460, 1360, 1140, 1115, 1090, 1020, 850

Elemental analysis value $C_{16}H_{30}O_4$:

Calculated value (%) C,67.10; H,10.56. Found value (%) C,67.56; H,10.93.

Referential Example 5

The procedure of Referential Example 3 was repeated to produce 2.48 g (yields: 65%) of diethyl allyl(4-iodobutyl)malonate from diethyl allylmalonate (2.0 g, 10 mmol) and 1,4-diiodobutane.

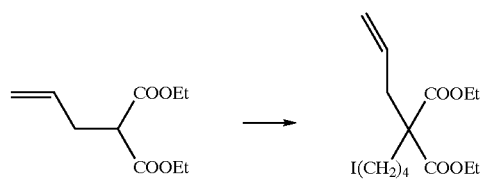

Characteristic Values of diethyl allyl(4-iodobutyl)malonate $^1$H-NMR, δ: 1.26 (t, J=7.0 Hz, 6H) 1.32–1.37 (m, 2H) 1.78–1.90 (m, 4H) 2.65 (d, J=7.4 Hz, 2H) 3.18 (t, J=6.9 Hz, 2H) 4.19 (q, J=7.1 Hz) 5.07–5.15 (m, 2H) 5.58–5.71 (m, 1H)

$^{13}$C-NMR, δ: 6.17, 14.12, 24.75, 31.04, 33.49, 36.94, 57.22, 61.22, 118.97, 132.40, 171.07

IR (neat): 3080, 2980, 2860, 1730, 1640, 1450, 1370, 1280, 1210, 1140, 1090, 1020, 920, 860

Elemental analysis value $C_{14}H_{23}O_4I$:

Calculated value (%) C,43.99; H,6.06. Found value (%) C,44.11; H,6.26.

EXAMPLE 22-4

The procedure of Example 22-1 was repeated to produce 0.412 g of diethyl (4-iodobutyl)malonate (yields: 92%) from diethyl allyl(4-iodobutyl)malonate (0.50 g, 1.31 mmol) by deallylating reaction.

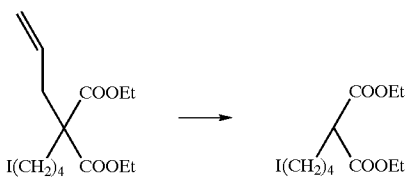

Characteristic Values of diethyl (4-iodobutyl)malonate $^1$H-NMR, δ: 1.28 (t, J=7.1 Hz, 6H) 1.39–1.52 (m, 2H) 1.80–1.96 (m, 4H) 3.19 (t, J=6.9 Hz, 2H) 3.32 (t, J=7.5 Hz, 1H) 4.21 (q, J=7.1 Hz, 4H)

$^{13}$C-NMR, δ: 5.92, 14.03, 27.54, 28.11, 32.95, 51.74, 61.30, 169.16

IR (neat): 2980, 2930, 2860, 1750, 1730, .1440, 1370, 1250, 1230, 1170, 1150, 1090, 1030, 855

Elemental analysis value $C_{11}H_{19}O_4I$:

Calculated value (%) C,38.61; H,5.60. Found value (%) C,39.07; H,5.96.

Referential Example 6

The procedure of Referential Example 3 was repeated to produce 4.52 g of diethyl allyl(2-carboaryloxyethyl)malonate (yields: 95%) from diethyl allylmalonate (3.06 g, 15.3 mmol) and allyl 3-bromopropionate (3.55 g, 18.4 mmol).

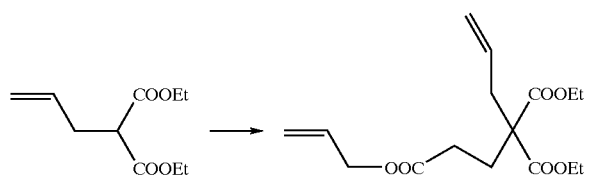

Characteristic Values of diethyl allyl(2-carboaryloxyethyl)malonate $^1$H-NMR, δ: 1.25 (t, J=7.1 Hz, 6H) 2.16–2.28 (m, 2H) 2.31–2.40 (m, 2H) 2.64 (d, J=7.5 Hz, 2H) 4.19 (q, J=7.1 Hz, 4H) 4.57 (d, J=6.0 Hz, 2H) 5.09–5.16 (m, 2H) 5.21–5.35 (m, 2H) 5.59–5.73 (m, 1H) 5.84–5.97 (m, 1H)

$^{13}$C-NMR, δ: 14.03, 26.63, 29.37, 37.62, 56.64, 61.34, 65.19, 118.18, 119.25, 132.06, 132.12, 170.68, 172.34

IR (neat): 3440, 3080, 2990, 1730, 1640, 1440, 1385, 1360, 1190, 1090, 1080, 1010, 990, 920, 850

Elemental analysis value $C_{14}H_{24}O_6$:

Calculated value (%) C,61.52; H,7.74. Found value (%) C,61.25; H,7.92.

Referential Example 7

To a THF solution (73 ml) containing $Pd_2(dba)_3 \cdot CHCl_3$ (0.207 g, 0.20 mmol), formic acid (1.31 g, 28.4 mmol), triethylamine (2.4 g, 24 mmol), and tributylphosphine (0.162 g, 0.8 mmol) was added at room temperature diethyl allyl(2-carboaryloxyethyl)malonate (2.51 g, 8 mmol). The reaction liquid was stirred at 40° C. for 2 hours. With 1N hydrochloric acid added, the reaction liquid was extracted with ether. The organic layer was washed with a saturated aqueous solution of sodium chloride and then extracted with a saturated aqueous solution of sodium hydrogen carbonate. The aqueous layer was made acid with 1N hydrochloric acid and then extracted with ether. The organic layer was dried with anhydrous magnesium sulfate and freed of solvent by vacuum distillation. Thus there was obtained 1.95 g of diethyl allyl(2-carboxyethyl)malonate (yields: 90%).

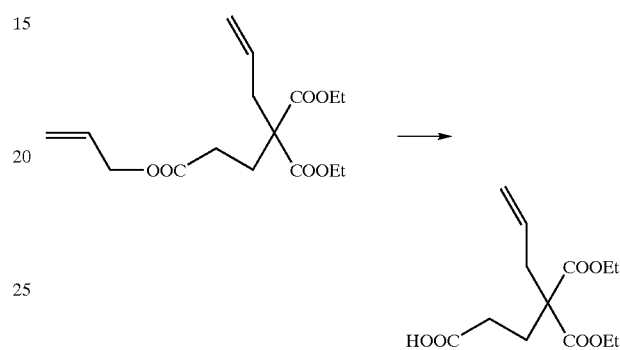

Characteristic Values of diethyl allyl(2-carboxyethyl)malonate $^1$H-NMR, δ: 1.26 (t, J=7.1 Hz, 6H) 2.19 (t, J=7.5 Hz, 2H) 2.38 (t, J=7.5 Hz, 2H) 2.66 (d, J=7.1 Hz, 2H) 4.19 (q, J=7.2 Hz, 4H) 5.10–5.17 (m, 2H) 5.59–5.73 (m, 1H)

Referential Example 8

A benzene solution (14.5 ml) containing diethyl allyl(2-carboxyethyl)malonate (1.95 g, 7.2 mmol) and oxalyl chloride (2.3 g, 18.1 mmol) was stirred at 70° C. for 1 hour. After cooling to room temperature, the reaction liquid was freed of solvent by vacuum distillation. Thus there was obtained 1.92 g of 4,4-dicarboethoxy-6-heptenic acid chloride (yields: 91%).

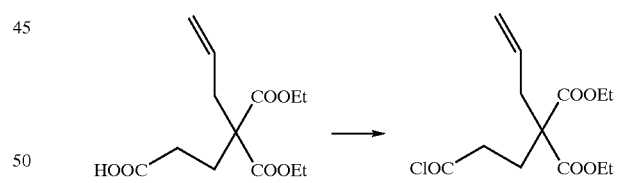

Characteristic Values of 4,4-dicarboethoxy-6-peptenic acid chloride $^1$H-NMR, δ: 1.26 (t, J=7.1 Hz, 6H) 2.22 (t, J=7.9 Hz, 2H) 2.64 (d, J=7.1 Hz, 2H) 3.00 (t, J=7.8 Hz, 2H) 4.20 (q, J=7.2 Hz, 4H) 5.11–5.16 (m, 2H) 5.57–5.71 (m, 1H)

Referential Example 9

To an ether suspension (2 ml) containing copper iodide (0.293 g, 1.2 mmol) was added dropwise at −10° C. 1.26 ml of 1.91M ether solution containing methyl lithium (2.4 mmol). After heating to 0° C. over 30 minutes, the reaction liquid was given 4,4-dicarboethoxy-6-heptenic acid chloride (0.291 g, 1.0 mmol), followed by stirring at 0° C. for 6 hours. After addition of a saturated aqueous solution of ammonium chloride, the reaction liquid was extracted with ether. The organic layer was dried with anhydrous magnesium sulfate and freed of solvent by vacuum distillation. The residues were purified by silica gel chromatography to give 0.295 g of 5,5-dicarboethoxy-7-octen-2-on (yields: 91%).

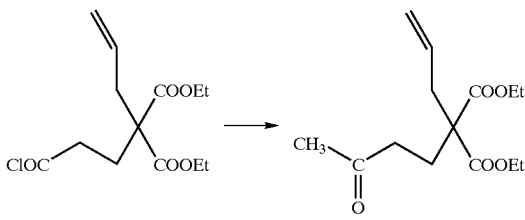

Characteristic Values of 5,5-dicarboethoxy-7-octen-2-on $^1$H-NMR, δ: 1.25 (t, J=7.1 Hz, 6H) 2.13 (t, J=8.0 Hz, 2H) 2.13 (s, 3H) 2.46 (t, J=7.9 Hz, 2H) 2.63 (d, J=6.1 Hz, 2H) 4.18 (q, J=7.0 Hz, 4H) 5.08–5.14 (m, 2H) 5.58–5.73 (m, 1H)

$^{13}$C-NMR, δ: 14.04, 26.48, 29.81, 37.94, 38.55, 56.57, 61.29, 119.14, 132.18, 170.86, 207.15

IR (neat): 3080, 2980, 1730, 1650, 1470, 1370, 1210, 1100, 1030, 930, 860

Elemental analysis value $C_{14}H_{22}O_5$:

Calculated value (%) C,62.20; H,8.20. Found value (%) C,62.31; H,8.44.

Referential Example 10

To a THF suspension (4.2 ml) containing triphenylmethylphosphonium bromide (0.536 g, 1.5 mmol) was added dropwise at 0° C. butyl lithium (1.4 mmol in 0.88 ml of 1.6M hexane solution). The reaction liquid was stirred at 0° C. for 30 minutes and then given 5,5-dicarboethoxy-7-octen-2-on (0.27 g, 1.0 mmol), followed by stirring at 0° C. for 1 hour. After treatment and purification as in Referential Example 9, there was obtained 0.239 g of diethyl allyl(3-methyl-3-butenyl)malonate (yields: 89%).

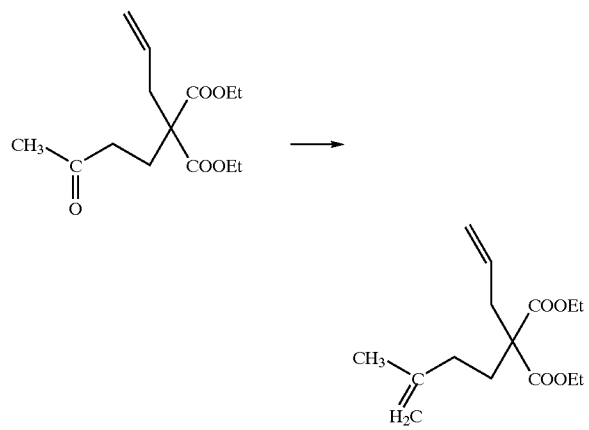

Characteristic Values of allyl(3-methyl-3-butenyl)malonate $^1$H-NMR, δ: 1.24 (t, J=7.1 Hz, 6H) 1.71 (s, 3H) 1.86–1.92 (m, 2H) 1.97–2.04 (m, 2H) 2.66 (d, J=6.6 Hz, 2H) 4.18 (q, J=7.1 Hz, 4H) 4.68 (s, 1H) 4.70 (s, 1H) 5.07–5.13 (m, 2H) 5.58–5.71 (m, 1H)

$^{13}$C-NMR, δ: 14.11, 22.39, 30.63, 32.09, 36.95, 57.21, 61.15, 110.33, 118.86, 132.49, 144.93, 171.15

IR (neat): 3080, 2980, 1730, 1640, 1450, 1370, 1275, 1220, 1200, 1180, 1090, 1030, 920, 890, 860

Elemental analysis value $C_{15}H_{20}O_4$:

Calculated value (%) C,67.14; H,9.01. Found value (%) C,66.99; H,9.31.

EXAMPLE 22-5

The procedure of Example 22-1 was repeated to produce 0.103 g of diethyl (3-methyl-3-butenyl)malonate (yields: 90%) from diethyl allyl(3-methyl-3-butenyl)malonate (0.134 g, 0.5 mmol) by deallylating reaction.

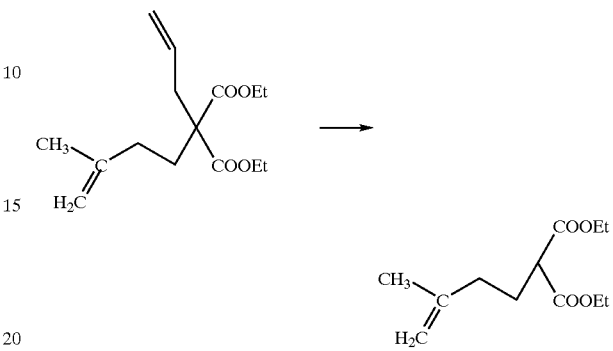

Characteristic Values of diethyl (3-methyl-3-butenyl)malonate $^1$H-NMR, δ: 1.27 (t, J=7.1 Hz, 6H) 1.73 (s, 3H) 2.05 (m, 4H) 3.31–3.38 (m, 1H) 4.20 (q, J=7.1 Hz, 4H) 4.70 (s, 1H) 4.76 (s, 1H)

$^{13}$C-NMR, δ: 14.01, 22.09, 26.61, 35.19, 51.30, 61.22, 111.11, 144.02, 169.38

IR (neat): 3080, 2980, 2940, 1750, 1730, 1650, 1450, 1370, 1150, 1100, 1030, 890, 860

Elemental analysis value $C_{12}H_{20}O_4$:

Calculated value (%) C,63.14; H,8.83. Found value (%) C,62.87; H,9.00.

Referential Example 11

To an ethanol solution (10.4 ml) containing sodium hydride (0.049 g, 1.13 mmol, 55% in oil) were added diethyl allylmalonate (3.0 g, 15 mmol) and methyl vinyl ketone (1.39 g, 19.9 mmol). The reaction liquid was stirred at room temperature for 22 hours. After treatment and purification as in Referential Example 1, there was obtained 3.56 g of 5,5-dicarboethoxy-7-octen-2-on (yields: 88%).

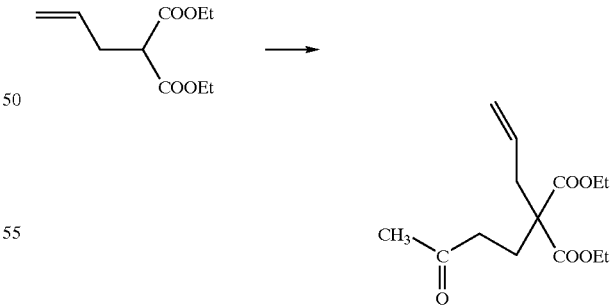

Comparative Referential Example 1

The procedure of Referential Example 3 was repeated to produce 0.20 g of diethyl (5-iodopentyl)malonate (yields: 57%) and 0.09 g of diethyl cyclohexane-1,1-dimalonate (yields: 40%) from diethyl malonate (0.16 g, 1.0 mmol) and 1,5-diiodopentane (0.65 g, 2.0 mmol).

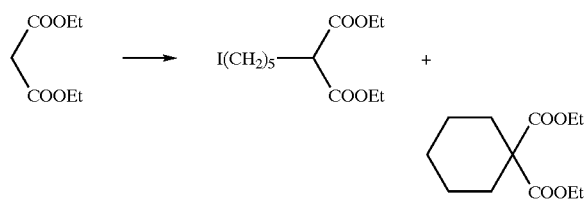

Characteristic Values of diethyl (5-iodopentyl)malonate $^1$H-NMR, δ: 1.27 (t, J=7.1 Hz, 6H) 1.22–1.49 (m, 4H) 1.79–1.88 (m, 4H) 3.18 (t, J=6.9 Hz, 2H) 3.32 (t, J=7.5 Hz, 1H) 4.20 (q, J=7.1 Hz, 4H)

$^{13}$C-NMR, δ: 6.63, 14.07, 26.20, 28.46, 30.05, 33.07, 51.92, 61.30, 169.37

IR (neat): 3000, 2940, 2860, 1740, 1470, 1460, 1380, 1250, 1230, 1160, 1100, 1030, 870, 760

Elemental analysis value $C_{12}H_{21}O_4I$:

Calculated value (%) C,40.46; H,5.94. Found value (%) C,41.11; H,6.20.

Characteristic Values of diethyl cyclohexane-1,1-dimalonate $^1$H-NMR, δ: 1.27 (t, J=7.1 Hz, 6H) 1.33–1.48 (m, 2H) 1.48–1.56 (m, 4H) 1.96 (m, 4H) 4.19 (q, J=7.1 Hz, 4H)

Comparative Referential Example 2

The procedure of Referential Example 4 was repeated to produce a mixture of diethyl nonylmalonate (yields: 10%) and diethyl cyclohexane-1,1-dimalonate (yields: 90%) from diethyl (5-iodopentyl)malonate (0.065 g, 0.18 mmol).

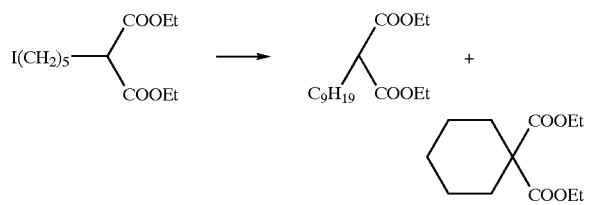

Comparative Referential Example 3

The procedure of Referential Example 5 was repeated to produce 0.135 g of diethyl cyclopentane-1,1-dimalonate only (yields: 62%) from diethyl malonate (0.16 g, 1.0 mmol) and 1,4-diiodobutane.

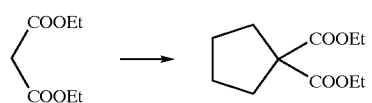

Characteristic Values of diethyl cyclopentane-1,1-dimalonate $^1$H-NMR, δ: 1.26 (t, J=7.1 Hz, 6H) 1.65–1.70 (m, 4H) 2.16–2.19 (m, 4H) 4.18 (q, J=7.1 Hz, 4H)

Comparative Referential Example 4

The procedure of Referential Example 6 was repeated to produce 0.751 g of diethyl (2-carboallylethyl)malonate (yields: 75%) from diethyl malonate (0.589 g, 3.68 mmol) and allyl 3-bromopropionate.

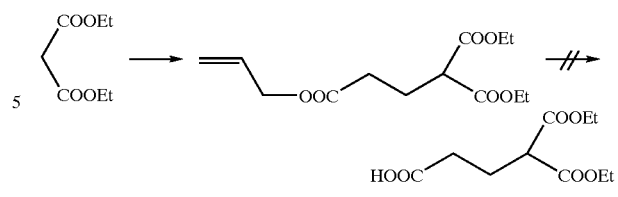

Characteristic Values of diethyl (2-carboallylethyl)malonate $^1$H-NMR, δ: 1.27 (t, J=7.3 Hz, 6H) 2.23 (dt, $J_1$=6.5 Hz, $J_2$=7.7 Hz, 2H) 2.43 (t, J=7.7 Hz, 2H) 3.45 (t, J=6.5 Hz, 1H) 4.20 (q, J=7.3 Hz, 4H) 4.57 (d, J=6.1 Hz, 2H) 5.21–5.33 (m, 2H) 5.83–5.98 (m, 1H)

This compound did not give the desired carboxylic acid by the same reaction as in Referential Example 7.

Comparative Referential Example 5

The procedure of Referential Example 11 was repeated to produce 1.68 g of diethyl (3-oxobutyl)malonate (yields: 64%) from diethyl malonate (2.0 g, 12.5 mmol) and methyl vinyl ketone.

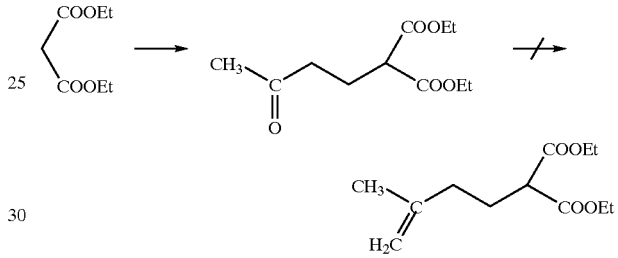

Characteristic Values of diethyl (3-oxobutyl)malonate $^1$H-NMR, δ: 1.27 (t, J=7.1 Hz, 6H) 2.15 (s, 3H) 2.11–2.26 (m, 2H) 2.55 (t, J=7.2 Hz, 2H) 3.39 (t, J=7.3 Hz, 1H), 4.20 (q, J=7.1 Hz, 4H)

This product (0.23 g, 1.0 mmol) in combination with Ph3P=CH$_2$ gave the desired diethyl (3-methyl-3-butenyl)malonate in an amount of only 0.045 g (yields: 20%).

What is claimed is:

1. A process for an addition reaction which comprises performing an addition reaction of a reactant compound having an electrophilic functional group or an electrophilic reagent, and a reagent made from a titanium compound represented by formula (I) below $$TiX^1X^2X^3X^4 \qquad (1)$$

(where $X^1$, $X^2$, $X^3$, and $X^4$ denote independently a halogen atom, $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring), a Grignard reagent represented by the formula (2) below in a molar amount 1–10 times as much as the titanium compound $$R^1MgX^5 \qquad (2)$$

(where $R^1$ denotes a $C_{2-10}$ alkyl group having a hydrogen atom at the β position and $X^5$ denotes a halogen atom), and a compound having a carbon-carbon unsaturated bond at a temperature in a range of −78° C. to 0° C., wherein the compound having a carbon-carbon unsaturated bond is not styrene; and wherein the addition reaction is not a polymerization reaction.

2. The process as defined in claim 1, wherein the reaction between a compound having an electrophilic functional group and a compound having a carbon-carbon unsaturated bond is followed by further addition of a compound having an electrophilic functional group.

3. The process as defined in claim 1 or 2, wherein the reaction between a compound having an electrophilic functional group and a compound having a carbon-carbon unsaturated bond is followed by addition of a electrophilic reagent.

4. The process for addition reaction as defined in claim 1, wherein the compound having a carbon-carbon unsaturated bond and the compound having an electrophilic functional group are replaced by a compound having both a carbon-carbon unsaturated bond and an electrophilic functional group in the same molecule for intramolecular addition reaction.

5. The process as defined in claim 4, wherein the intramolecular addition reaction for a compound having a carbon-carbon unsaturated bond and an electrophilic functional group is followed by further addition of a compound having an electrophilic functional group.

6. The process as defined in claim 4 or 5, wherein the intramolecular addition reaction for a compound having a carbon-carbon unsaturated bond and an electrophilic functional group is followed by addition of an electrophilic reagent.

7. The process defined in claim 1, wherein the titanium compound is one which has an asymmetric ligand.

8. The process defined in claim 1, wherein the compound having a carbon-carbon unsaturated bond is any of olefin compounds, acetylene compounds, or allene compounds.

9. The process defined in claim 1, wherein the electrophilic functional group is an aldehyde group, ketone group, imino group, hydrazone group, aliphatic double bond, aliphatic triple bond, acyl group, ester group, or carbonate group.

10. The process defined in claim 1, wherein the electrophilic reagent is water, heavy water, chlorine, bromine, iodine, N-bromosuccimide, oxygen, carbon dioxide gas, or carbon monoxide.

11. A process which comprises:

reacting a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring) and a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom) thereby forming a titanium catalyst; and deallylating in the presence of the titanium catalyst an allyl-substituted malonate ester derivative represented by the formula (3) below $$R^2R^3C=CR^4CH_2C(Ra)(COORb)_2 \quad (3)$$

(where $R^2$, $R^3$, and $R^4$ denote independently a hydrogen atom or $C_{1-10}$ alkyl group, Ra denotes a $C_{1-20}$ substituted or unsubstituted alkyl group, alkenyl group, or aralkyl group, and Rb denotes a $C_{1-10}$ alkyl group or aralkyl group), thereby giving a malonate ester derivative represented by the formula (4) below $$RaCH(COORb)_2 \quad (4)$$

(where Ra and Rb are defined as above).

12. A process which comprises alkylating an allylmalonate ester represented by the formula (5) below $$R^2R^3C=CR^4CH_2CH(COORb)_2 \quad (5)$$

(where $R^2$, $R^3$, and $R^4$ denote independently a hydrogen atom or $C_{1-10}$ alkyl group, and Rb denotes a $C_{1-10}$ alkyl group or aralkyl group), thereby giving an allyl-substituted malonate ester derivative represented by the formula (3) below $$R^2R^3C=CR^4CH_2C(Ra)(COORb)_2 \quad (3)$$

(where $R^2$, $R^3$, $R^4$, and Rb are defined as above, and Ra denotes a $C_{1-20}$ substituted or unsubstituted alkyl group, alkenyl group, or aralkyl group), reacting this derivative with a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring) and a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom), thereby forming a titanium catalyst, and performing deallylating reaction in the presence of the titanium catalyst, thereby giving a malonate ester derivative represented by the formula (4) below $$RaCH(COORb)_2 \quad (4)$$

(where Ra and Rb are defined as above).

13. The process as defined in claim 11 or 12, wherein $R^2$, $R^3$, and $R^4$ each denote a hydrogen atom.

14. A titanium catalyst for reaction between a compound having a carbon-carbon unsaturated bond and a compound having an electrophilic functional group or an electrophilic reagent, said titanium catalyst being composed of a titanium compound represented by the formula (1) below $$TiX^1X^2X^3X^4 \quad (1)$$

(where $X^1$, $X^2$, $X^3$, and $X^4$ denote independently a halogen atom, $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring) and a Grignard reagent represented by the formula (2) below in a molar amount 1–10 times as much as the titanium compound, $$R^1MgX^5 \quad (2)$$

(where $R^1$ denotes a $C_{2-10}$ alkyl group having a hydrogen atom at the β position and $X^5$ denotes a halogen atom);

wherein when the compound having a carbon-carbon unsaturated bond is an olefin, the olefin is selected from the group consisting of a substituted or unsubstituted halogenated allyl and a substituted or unsubstituted allyl alcohol derivative; and wherein the $C_{2-10}$ alkyl group of $R^1$ does not act as a nucleophile in the reaction; and wherein the reaction between a compound having a carbon-carbon unsaturated bond and a compound having an electrophilic functional group or an electrophilic reagent is not a polymerization reaction.

15. An organotitanium reacting reagent which is composed of a titanium compound represented by the formula (1) below $$TiX^1X^2X^3X^4 \qquad (1)$$

(where $X^1$, $X^2$, $X^3$, and $X^4$ denote independently a halogen atom, $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring) and a Grignard reagent represented by the formula (2) below in a molar amount 1–10 times as much as the titanium compound, $$R^1MgX^5 \qquad (2)$$

(where $R^1$ denotes a $C_{2-10}$ alkyl group having a hydrogen atom at the β position and $X^5$ denotes a halogen atom), and a compound having a carbon-carbon unsaturated bond;

wherein when the compound having a carbon-carbon unsaturated bond is an olefin, the olefin is selected from the group consisting of a substituted or unsubstituted halogenated allyl and a substituted or unsubstituted allyl alcohol derivative; and wherein the $C_{2-10}$ alkyl group of $R^1$ does not act as a nucleophile in the reaction; and wherein the organotitanium reacting reagent is not used in a polymerization reaction.

16. A process for producing an organotitanium reacting reagent, said process comprising reacting together a titanium compound represented by the formula (1) below $$TiX^1X^2X^3X^4 \qquad (1)$$

(where $X^1$, $X^2$, $X^3$, and $X^4$ denote independently a halogen atom), $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring) and a Grignard reagent represented by the formula (2) below in a molar amount 1–10 times as much as the titanium compound, $$R^1MgX^5 \qquad (2)$$

(where $R^1$ denotes a $C_{2-10}$ alkyl group having a hydrogen atom at the β position and $X^5$ denotes a halogen atom), and a compound having a carbon-carbon unsaturated bond;

wherein when the compound having a carbon-carbon unsaturated bond is an olefin, the olefin is selected from the group consisting of a substituted or unsubstituted halogenated allyl and a substituted or unsubstituted allyl alcohol derivative; and wherein the organotitanium reacting reagent is not used in a polymerization reaction.

17. A process for an addition reaction which comprises combining a compound having a carbon-carbon unsaturated bond and a compound having an electrophilic functional group or an electrophilic reagent, in the presence of a titanium compound represented by the formula (1) below $$TiX^1X^2X^3X^4 \qquad (1)$$

(where $X^1$, $X^2$, $X^3$, and $X^4$ denote independently a halogen atom, $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring) and a Grignard reagent represented by the formula (2) below in a molar amount 1–10 times as much as the titanium compound, $$R^1MgX^5 \qquad (2)$$

(where $R^1$ denotes a $C_{2-10}$ alkyl group having a hydrogen atom at the β position and $X^5$ denotes a halogen atom);

wherein when the compound having a carbon-carbon unsaturated bond is an olefin, the olefin is selected from the group consisting of a substituted or unsubstituted halogenated allyl and a substituted or unsubstituted allyl alcohol derivative; and wherein the addition reaction is not a polymerization reaction.

18. A process for an addition reaction which comprises adding to an organotitanium reacting reagent comprising:

a titanium compound represented by formula (I) below $$TiX^1X^2X^3X^4 \qquad (1)$$

(where $X^1$, $X^2$, $X^3$, and $X^4$ denote independently a halogen atom, $C_{1-20}$ alkoxy group, aralkyloxy group, aryloxy group, or —NRxRy group (where Rx and Ry denote independently a $C_{1-20}$ alkyl group or aralkyl group), and any two of $X^1$, $X^2$, $X^3$, and $X^4$ may form a ring) and a Grignard reagent represented by the formula (2) below in a molar amount 1–10 times as much as the titanium compound, $$R^1MgX^5 \qquad (2)$$

(where $R^1$ denotes a $C_{2-10}$ alkyl group having a hydrogen atom at the β position and $X^5$ denotes a halogen atom), and a compound having a carbon-carbon unsaturated bond, a compound having an electrophilic functional group or an electrophilic reagent, thereby performing an addition reaction on the compound having a carbon-carbon unsaturated bond in the presence of said organotitanium reacting reagent, wherein when the compound having a carbon-carbon unsaturated bond is an olefin, the olefin is selected from the group consisting of a substituted or unsubstituted halogenated allyl and a substituted or unsubstituted allyl alcohol derivative; and wherein the addition reaction is not a polymerization reaction.

19. The process as defined in claim 1, wherein the addition reaction is an intramolecular or dimerization reaction.

20. The titanium catalyst as defined in claim 14, wherein the reaction between a compound having a carbon-carbon unsaturated bond and a compound having an electrophilic functional group or an electrophilic reagent is an intramolecular or dimerization reaction.

21. The organotitanium reacting reagent as defined in claim 15, wherein the organotitanium reacting reagent is used in an intramolecular or dimerization reaction.

22. The process for producing an organotitanium reacting reagent as defined in claim 16, wherein the organotitanium reacting reagent is used in an intramolecular or dimerization reaction.

23. The process as defined in claim 17, wherein the addition reaction is an intramolecular or dimerization reaction.

24. The process as defined in claim 18, wherein the addition reaction is an intramolecular or dimerization reaction.

* * * * *